United States Patent
Mao et al.

(10) Patent No.: US 11,235,071 B2
(45) Date of Patent: Feb. 1, 2022

(54) COMPOSITIONS OF NUCLEIC ACID-CONTAINING NANOPARTICLES FOR IN VIVO DELIVERY

(71) Applicant: THE JOHNS HOPKINS UNIVERSITY, Baltimore, MD (US)

(72) Inventors: Hai-Quan Mao, Baltimore, MD (US); John Michael Williford, Chicago, IL (US); Maani Archang, Baltimore, MD (US); Il Minn, Ellicott City, MD (US); Yong Ren, Baltimore, MD (US); Jose Luis Santos, Rockville, MD (US); Martin G. Pomper, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 74 days.

(21) Appl. No.: 15/890,771

(22) Filed: Feb. 7, 2018

(65) Prior Publication Data
US 2018/0177892 A1   Jun. 28, 2018

Related U.S. Application Data

(63) Continuation of application No. 15/154,143, filed on May 13, 2016, now abandoned.

(60) Provisional application No. 62/161,546, filed on May 14, 2015.

(51) Int. Cl.
| | | |
|---|---|---|
| A61K 48/00 | (2006.01) | |
| A61K 45/06 | (2006.01) | |
| C12N 15/88 | (2006.01) | |
| A61K 47/62 | (2017.01) | |
| A61K 47/69 | (2017.01) | |
| A61K 47/64 | (2017.01) | |
| A61K 47/60 | (2017.01) | |
| A61K 47/68 | (2017.01) | |
| A61K 47/59 | (2017.01) | |

(52) U.S. Cl.
CPC .......... *A61K 48/0041* (2013.01); *A61K 45/06* (2013.01); *A61K 47/59* (2017.08); *A61K 47/60* (2017.08); *A61K 47/62* (2017.08); *A61K 47/64* (2017.08); *A61K 47/6803* (2017.08); *A61K 47/6935* (2017.08); *C12N 15/88* (2013.01); *C12N 2810/855* (2013.01); *C12N 2810/856* (2013.01)

(58) Field of Classification Search
None
See application file for complete search history.

(56) References Cited

U.S. PATENT DOCUMENTS

2009/0011004 A1   1/2009   Lutz et al.

OTHER PUBLICATIONS

Choi et al., Effect of Polyethylene glycol) Grafting on Polyethylenimine as a Gene Transfer Vector in vitro. Bull. Korean Chem. Soc. 2001, vol. 22, No. 1 (Year: 2001).*
Vinogradov et al., Polyion Complex Micelles with Protein-Modified Corona for Receptor-Mediated Delivery of Oligonucleotides into Cells. Bioconjugate Chem. 1999, 10, 851-860 (Year: 1999).*
Judge et al. Role for IkBa, but not c-Rel, in skeletal muscle atrophy. Am J Physiol Cell Physiol 292: C372-C382, 2007. (Year: 2007).*
Vinogradov et al., Self-Assembly of Polyamine-Poly(ethylene glycol) Copolymers with Phosphorothioate Oligonucleotides (Bioconjug Chem, 1998, 9:805-812) (Year: 1998).*
Ke et al., Subtle changes in surface-tethered groups on PEGylated DNA nanoparticles significantly influence gene transfection and cellular uptake. Nanomedicine: Nanotechnology, Biology, and Medicine 19 (2019) 126-135 (Year: 2019).*
Sherman et al., Role of the Methoxy Group in Immune Responses to mPEG-Protein Conjugates. Bioconjug Chem. Mar. 21, 2012; 23(3): 485-499. (Year: 2012).*
International Search Report and the Written Opinion dated Sep. 30, 2016 for a corresponding International Application No. PCT/US2016/032364.
Sung, S.-J. et al., Effect of polyethylene glycol on gene delivery of polyethylenimine. Biological and Pharmaceutical Bulletin, 2003, vol. 26, No. 4, pp. 492-500.
Petersen, H. et al., Polyethylenimine-graft-poly (ethylene glycol) copolymers: influence of copolymer block structure on DNA complexation and biological activities as gene delivery system. Bioconjugate Chemistry, 2002, vol. 13, No. 4, pp. 845-854.

(Continued)

*Primary Examiner* — Arthur S Leonard
(74) *Attorney, Agent, or Firm* — Casimir Jones, S.C.; Jeffrey W. Childers

(57) ABSTRACT

Compositions comprising a polymeric micellar nanoparticle composition comprising a block or graft copolymer comprising at least one polycationic polymer and at least one polyethylene glycol (PEG) polymer having an average molecular weight less than 1 kDa, and at least one nucleic acid, wherein the graft or block copolymer and at least one nucleic acid are complexed and condensed into a shaped micellar nanoparticle that is stable in biological media are disclosed. The presently disclosed subject matter also provides a method for preparing the presently disclosed polymeric micellar nanoparticle compositions, a method for targeting at least one metastatic cancer cell in a subject, and a method for treating a disease or condition using the presently disclosed polymeric micellar nanoparticle compositions.

24 Claims, 38 Drawing Sheets
(33 of 38 Drawing Sheet(s) Filed in Color)
Specification includes a Sequence Listing.

(56) References Cited

OTHER PUBLICATIONS

Choi, Y. H. et al., Polyethylene glycol-grafted poly-L-lysine as polymeric gene carrier. Journal of Controlled Release, 1998, vol. 54, pp. 39-48.

Luo, X. et al., Stability of poly (ethylene glycol)-graft-polyethylenimine copolymer/DNA complexes: influences of PEG molecular weight and PEGylation degree. Journal of Materials Science: Materials in Medicine, 2010, vol. 21, pp. 597-607.

Albanese A, Tang PS, Chan WC. 2012. The effect of nanoparticle size, shape, and surface chemistry on biological systems. Annual Review of Biomedical Engineering 14:1-16.

Alexis, F.; Pridgen, E.; Molnar, L. K.; Farokhzad, O. C. Factors affecting the clearance and biodistribution of polymeric nanoparticles. Molecular pharmaceutics, 2008, 5, 505-15.

Bae, Y. H.; Park, K. Targeted drug delivery to tumors: myths, reality and possibility. Journal of controlled release : official journal of the Controlled Release Society, 2011, 153, 198-205.

Banerjee, S. R. et al., Sequential SPECT and optical imaging of experimental models of prostate cancer with a dual modality inhibitor of the prostate-specific membrane antigen. Angewandte Chemie-International Edition 50, 9167-9170, 2011. PMC3192196.

Barua, S et al., Particle shape enhances specificity of antibody-displaying nanoparticles. Proc. Natl. Acad. Sci. U.S.A., 2013, 110, 3270-5.

Baum, C.; Kustikova, O.; Modlich, U.; Li, Z.; Fehse, B. Mutagenesis and oncogenesis by chromosomal insertion of gene transfer vectors. Human gene therapy, 2006, 17, 253-63.

Bertrand, N.; Wu, J.; Xu, X.; Kamaly, N.; Farokhzad, O. C. Cancer nanotechnology: the impact of passive and active targeting in the era of modern cancer biology. Advanced Drug Delivery Reviews, 2014, 66, 2-25.

Bessis, N.; GarciaCozar, F. J.; Boissier, M. C. Immune responses to gene therapy vectors: influence on vector function and effector mechanisms. Gene therapy, 2004, 11 Suppl 1, S10-7.

Bhang, H.-e. C., Gabrielson, K. L., Laterra, J., Fisher, P. B., Pomper, M. G. Tumor-specific imaging through progression elevated gene-3 promoter-driven gene expression. Nature Medicine 17, 123-129 (2011). PMC3057477.

Blessing, T.; Kursa, M.; Holzhauser, R.; Kircheis, R.; Wagner, E. Different strategies for formation of pegylated EGF-conjugated PEI/DNA complexes for targeted gene delivery. Bioconjugate chemistry, 2001, 12, 529-37.

Bonnet, M.-E.; Erbacher, P.; Bolcato-Bellemin, A.-L. Systemic delivery of DNA or siRNA dediated by linear polyethylenimine (L-PEI) does not induce an inflammatory response. Pharmaceutical Research, 2008, 25, 2972-2982.

Bouard, D.; Alazard-Dany, D.; Cosset, F. L. Viral vectors: from virology to transgene expression. British journal of pharmacology, 2009, 157, 153-65.

Brissault, B.; Leborgne, C.; Guis, C.; Danos, O.; Cheradame, H.; Kichler, A. Linear topology confers in vivo gene transfer activity to polyethylenimines. Bioconjugate chemistry, 2006, 17, 759-765.

Carlsson, J.; Drevin, H.; Axen, R. Protein thiolation and reversible protein-protein conjugation. N-Succinimidyl 3-(2-pyridyldithio)propionate, a new heterobifunctional reagent. The Biochemical journal, 1978, 173, 723-37.

Chauhan, V. P.; Jain, R. K. Strategies for advancing cancer nanomedicine. Nature Materials, 2013, 12, 958-62.

Chauhan, V. P.; Popovic, Z.; Chen, O.; Cui, J.; Fukumura, D.; Bawendi, M. G.; Jain, R. K. Fluorescent nanorods and nanospheres for real-time in vivo probing of nanoparticle shape-dependent tumor penetration. Angewandte Chemie-International Edition, 2011, 50, 11417-11420.

Cho, S. Y. et al., Biodistribution, tumor detection, and radiation dosimetry of 18F-DCFBC, a low-molecular-weight inhibitor of prostate-specific membrane antigen, in patients with metastatic prostate cancer. Journal of Nuclear Medicine 53, 1883-1891 (2012).

Davis, M. E. Non-viral gene delivery systems. Current opinion in biotechnology, 2002, 13, 128-31.

Dedhar, S.; Saulnier, R.; Nagle, R.; Overall, C. M. Specific Alterations in the Expression of Alpha-3-Beta-1 and Alpha-6-Beta-4 Integrins in Highly Invasive and Metastatic Variants of Human Prostate Carcinoma-Cells Selected by in-Vitro Invasion through Reconstituted Basement-Membrane. Clin Exp Metastas, 1993, 11, 391-400.

Erbacher, P.; Bellinger, T.; Belguise-Valladier, P.; Zou, S. M.; Coll, J. L.; Behr, J. P.; Remy, J. S. Transfection and physical properties of various saccharide, poly(ethylene glycol), and antibody-derivatized polyethylenimines (PEI). Journal of Gene Medicine, 1999, 1, 210-222.

Ge, Z. S.; Chen, Q. X.; Osada, K.; Liu, X. Y.; Tockary, T. A.; Uchida, S.; Dirisala, A.; Ishii, T.; Nomoto, T.; Toh, K.; Matsumoto, Y.; Oba, M.; Kano, M. R.; Itaka, K.; Kataoka, K. Targeted gene delivery by polyplex micelles with crowded PEG palisade and cRGD moiety for systemic treatment of pancreatic tumors. Biomaterials, 2014, 35, 3416-3426.

Geng, Y.; Dalhaimer, P.; Cai, S.; Tsai, R.; Tewari, M.; Minko, T.; Discher, D. E. Shape effects of filaments versus spherical particles in flow and drug delivery. Nature Nanotechnology, 2007, 2, 249-55.

Ginn, S. L.; Alexander, I. E.; Edelstein, M. L.; Abedi, M. R.; Wixon, J. Gene therapy clinical trials worldwide to 2012—an update. The journal of gene medicine, 2013, 15, 65-77.

Goula, D.; Benoist, C.; Mantero, S.; Merlo, G.; Levi, G.; Demeneix, B. A. Polyethylenimine-based intravenous delivery of transgenes to mouse lung. Gene therapy, 1998, 5, 1291-5.

Gratton, S. E. A.; Ropp, P. A.; Pohlhaus, P. D.; Luft, J. C.; Madden, V. J.; Napier, M. E.; DeSimone, J. M. The effect of particle design on cellular internalization pathways. Proceedings of the National Academy of Sciences of the United States of America, 2008, 105, 11613-11618.

Harada-Shiba, M.; Yamauchi, K.; Harada, A.; Takamisawa, I.; Shimokado, K.; Kataoka, K. Polyion complex micelles as vectors in gene therapy—pharmacokinetics and in vivo gene transfer. Gene therapy, 2002, 9, 407-14.

Hashida, M.; Nishikawa, M.; Yamashita, F.; Takakura, Y. Cell-specific delivery of genes with glycosylated carriers. Advanced Drug Delivery Reviews, 2001, 52, 187-196.

Hatakeyama, H.; Akita, H.; Harashima, H. A multifunctional envelope type nano device (MEND) for gene delivery to tumours based on the EPR effect: a strategy for overcoming the PEG dilemma. Adv Drug Deliv Rev, 2011, 63, 152-60.

Hine, C. M.; Seluanov, A.; Gorbunova, V. Rad51 promoter-targeted gene therapy is effective for in vivo visualization and treatment of cancer. Molecular therapy : the journal of the American Society of Gene Therapy, 2012, 20, 347-55.

Hsu, C. Y.; Uludag, H. Nucleic-acid based gene therapeutics: delivery challenges and modular design of nonviral gene carriers and expression cassettes to overcome intracellular barriers for sustained targeted expression. Journal of drug targeting, 2012, 20, 301-28.

Itaka, K.; Kataoka, K. Progress and prospects of polyplex nanomicelles for plasmid DNA delivery. Current gene therapy, 2011, 11, 457-65.

Jere, D.; Jiang, H. L.; Arote, R.; Kim, Y. K.; Choi, Y. J.; Cho, M. H.; Akaike, T.; Cho, C. S. Degradable polyethylenimines as DNA and small interfering RNA carriers. Expert Opinion on Drug Delivery, 2009, 6, 827-34.

Jiang X. et al, Pharm. Res. 2011, 28:1317. String-like Micellar Nanoparticles Formed by Complexation of PEG-b-PPA and Plasmid DNA and Their Transfection Efficiency.

Jiang, X., Dai, H., Ke, C. Y., Mo, X., Torbenson, M. S., Li, Z. P., Mao, H. Q. PEG-b-PPA/DNA micelles improve transgene expression in rat liver through intrabiliary infusion. Journal of Controlled Release 122, 297-304 (2007). PMC2035949.

Jiang, X., Qu, W., Pan, D., Ren, Y., Williford, J.-M., Cui, H., Luijten, E., Mao, H.-Q. Plasmid-templated shape control of condensed DNA-block copolymer nanoparticles. Advanced Materials 25, 227-232 (2013). PMC3918481.

Jiang, X., Zheng, Y., Chen, H. H., Leong, K. W., Wang, T. H., Mao, H. Q. Dual-sensitive micellar nanoparticles regulate DNA unpacking and enhance gene-delivery efficiency. Advanced Materials 22, 2556-2560 (2010). PMC3000804.

(56) References Cited

OTHER PUBLICATIONS

Jones, C. H.; Chen, C. K.; Ravikrishnan, A.; Rane, S.; Pfeifer, B. A. Overcoming nonviral gene delivery barriers: perspective and future. Molecular pharmaceutics, 2013, 10, 4082-98.

Kang, Y.; Zhang, X.; Jiang, W.; Wu, C.; Chen, C.; Zheng, Y.; Gu, J.; Xu, C. Tumor-directed gene therapy in mice using a composite nonviral gene delivery system consisting of the piggyBac transposon and polyethylenimine. BMC cancer, 2009, 9, 126.

King, T. E.; Pawar, S. C.; Majuta, L.; Sroka, I. C.; Wynn, D.; Demetriou, M. C.; Nagle, R. B.; Porreca, F.; Cress, A. E. The Role of Alpha 6 Integrin in Prostate Cancer Migration and Bone Pain in a Novel Xenograft Model. Plos One, 2008, 3.

Kishimoto, H., Kojima, T., Watanabe, Y., Kagawa, S., Fujiwara, T., Uno, F., Teraishi, F., Kyo, S., Mizuguchi, H., Hashimoto, Y., Urata, Y., Tanaka, N., Fujiwara, T. In vivo imaging of lymph node metastasis with telomerase-specific replication-selective adenovirus. Nature Medicine 12, 1213-1219 (2006).

Klutz, K. et al., Epidermal growth factor receptor-targeted (131)I-therapy of liver cancer following systemic delivery of the sodium iodide symporter gene. Molecular therapy : the journal of the American Society of Gene Therapy, 2011, 19, 676-85.

Knorr, V.; Allmendinger, L.; Walker, G. F.; Paintner, F. F.; Wagner, E. An acetal-based PEGylation reagent for pH-sensitive shielding of DNA polyplexes. Bioconjugate chemistry, 2007, 18, 1218-25.

Kolhar, P.; Anselmo, A. C.; Gupta, V.; Pant, K.; Prabhakarpandian, B.; Ruoslahti, E.; Mitragotri, S. Using shape effects to target antibody-coated nanoparticles to lung and brain endothelium. Proc. Natl. Acad. Sci. U.S.A., 2013, 110, 10753-8.

Lavergne, E.; Combadiere, C.; Iga, M.; Boissonnas, A.; Bonduelle, O.; Maho, M.; Debre, P.; Combadiere, B. Intratumoral CC chemokine ligand 5 overexpression delays tumor growth and increases tumor cell infiltration. Journal of immunology, 2004, 173, 3755-62.

Lee M, Kim SW. 2005. Polyethylene glycol-conjugated copolymers for plasmid DNA delivery. Pharmaceutical Research 22:1-10.

Li SD, Huang L. 2010. Stealth nanoparticles: high density but sheddable PEG is a key for tumor targeting. Journal of Controlled Release 145:178-81.

Li, X.; Liu, X.; Josey, B.; Chou, C. J.; Tan, Y.; Zhang, N.; Wen, X. Short laminin peptide for improved neural stem cell growth. Stem cells translational medicine, 2014, 3, 662-70.

Li, Y.; Kroger, M.; Liu, W. K. Endocytosis of PEGylated nanoparticles accompanied by structural and free energy changes of the grafted polyethylene glycol. Biomaterials, 2014, 35, 8467-8478.

Mishra, S.; Webster, P.; Davis, M. E. PEGylation significantly affects cellular uptake and intracellular trafficking of non-viral gene delivery particles. Eur J Cell Biol, 2004, 83, 97-111.

Morille, M.; Passirani, C.; Vonarbourg, A.; Clavreul, A.; Benoit, J. P. Progress in developing cationic vectors for non-viral systemic gene therapy against cancer. Biomaterials, 2008, 29, 3477-96.

Mura, S.; Nicolas, J.; Couvreur, P. Stimuli-responsive nanocarriers for drug delivery. Nature Materials, 2013, 12, 991-1003.

Nagle R. B.; Hao J. S.; Knox, J. D.; Dalkin, B. L.; Clark, V.; Cress, A. E. Expression of Hemidesmosomal and Extracellular-Matrix Proteins by Normal and Malignant Human Prostate Tissue. Am J Pathol, 1995, 146, 1498-1507.

Namgung, R.; Kim, J.; Singha, K.; Kim, C. H.; Kim, W. J. Synergistic effect of low cytotoxic linear polyethylenimine and multiarm polyethylene glycol: study of physicochemical properties and in vitro gene transfection. Molecular pharmaceutics, 2009, 6, 1826-35.

Nomoto, T. et al., In situ quantitative monitoring of polyplexes and polyplex micelles in the blood circulation using intravital real-time confocal laser scanning microscopy. Journal of controlled release : official journal of the Controlled Release Society, 2011, 151, 104-109.

Oe, Y. et al., Actively-targeted polyion complex micelles stabilized by cholesterol and disulfide cross-linking for systemic delivery of siRNA to solid tumors. Biomaterials 35, 7887-7895 (2014).

Osada, K. Development of functional polyplex micelles for systemic gene therapy. Polym J, 2014, 46, 469-475.

Pack DW, Hoffman AS, Pun S, Stayton PS. 2005. Design and development of polymers for gene delivery. Nature Reviews Drug Discovery 4:581-93.

Park, K. Facing the truth about nanotechnology in drug delivery. ACS Nano, 2013, 7, 7442-7.

Patnaik, S.; Gupta, K. C. Novel polyethylenimine-derived nanoparticles for in vivo gene delivery. Expert Opinion on Drug Delivery, 2013, 10, 215-228.

Peer, D.; Karp, J. M.; Hong, S.; FaroKhzad, O. C.; Margalit, R.; Langer, R. Nanocarriers as an emerging plafform for cancer therapy. Nature Nanotechnology, 2007, 2, 751-760.

Pozzi, D. et al., Effect of polyethyleneglycol (PEG) chain length on the bio-nano-interactions between PEGylated lipid nanoparticles and biological fluids: from nanostructure to uptake in cancer cells. Nanoscale, 2014, 6, 2782-2792.

Ren, Y.; Jiang, X. A.; Pan, D.; Mao, H. Q. Charge Density and Molecular Weight of Polyphosphoramidate Gene Carrier Are Key Parameters Influencing Its DNA Compaction Ability and Transfection Efficiency. Biomacromolecules, 2010, 11, 3432-3439.

Rodl, W.; Schaffert, D.; Wagner, E.; Ogris, M. Synthesis of polyethylenimine-based nanocarriers for systemic tumor targeting of nucleic acids. Methods in molecular biology, 2013, 948, 105-20.

Schaffert, D.; Wagner, E. Gene therapy progress and prospects: synthetic polymer-based systems. Gene therapy, 2008, 15, 1131-8.

Shallal, H. M.; Minn, I.; Banerjee, S. R.; Lisok, A.; Mease, R. C.; Pomper, M. G. Heterobivalent agents targeting PSMA and integrin-alphavbeta3. Bioconjugate chemistry, 2014, 25, 393-405.

Shi J, Choi JL, Chou B, Johnson RN, Schellinger JG, Pun SH. 2013. Effect of polyplex morphology on cellular uptake, intracellular trafficking, and transgene expression. ACS Nano 7:10612-20.

Stefanick, J. F.; Ashley, J. D.; Kiziltepe, T.; Bilgicer, B. A systematic analysis of peptide linker length and liposomal polyethylene glycol coating on cellular uptake of peptide-targeted liposomes. ACS Nano, 2013, 7, 2935-47.

Thomas, C. E.; Ehrhardt, A.; Kay, M. A. Progress and problems with the use of viral vectors for gene therapy. Nature reviews. Genetics, 2003, 4, 346-58.

Thomas, M.; Klibanov, A. M. Non-viral gene therapy: polycation-mediated DNA delivery. Applied microbiology and biotechnology, 2003, 62, 27-34.

Tockary TA, Osada K, Chen Q, Machitani K, Dirisala A, et al. 2013. Tethered PEG crowdedness determining shape and blood circulation profile of polyplex micelle gene carriers. Macromolecules 46:6585-92.

Wei, Z.; Ren, Y.; Williford, J.-M.; Qu, W.; Huang, K.; Ng, S.; Mao, H.-Q.; Luijten, E. Simulation and Experimental Assembly of DNA-Graft Copolymer Micelles with Controlled Morphology. ACS Biomaterials Science & Engineering, 2015.

Wiethoff, C. M.; Middaugh, C. R. Barriers to nonviral gene delivery. Journal of pharmaceutical sciences, 2003, 92, 203-17.

Williford, J. M.; Ren, Y.; Huang, K.; Pan, D.; Mao, H. Q. Shape Transformation Following Reduction-Sensitive PEG Cleavage of Polymer/DNA Nanoparticles. Journal of materials chemistry. B, Materials for biology and medicine, 2014, 2, 8106-8109.

Williford, J.-M.; Santos, J. L; Shyam, R.; Mao, H.-Q. Shape control in engineering of polymeric nanoparticles for therapeutic delivery. Biomaterials Science, 2015.

Wong SY, Pelet JM, Putnam D. 2007. Polymer systems for gene delivery-past, present, and future. Progress in Polymer Science 32:799-837.

Yang, J.; Hendricks, W.; Liu, G. S.; McCaffery, J. M.; Kinzler, K. W.; Huso, D. L.; Vogelstein, B.; Zhou, S. B. A nanoparticle formulation that selectively transfects metastatic tumors in mice. Proceedings of the National Academy of Sciences of the United States of America, 2013, 110, 14717-14722.

Yin, H.; Kanasty, R. L.; Eltoukhy, A. A.; Vegas, A. J.; Dorkin, J. R.; Anderson, D. G. Non-viral vectors for gene-based therapy. Nature reviews. Genetics, 2014, 15, 541-55.

Young, L. S.; Murray, P. G. Epstein-Barr virus and oncogenesis: from latent genes to tumours. Oncogene 22, 5108-5121 (2003).

Zhang Y, Satterlee A, Huang L. 2012. In vivo gene delivery by nonviral vectors: overcoming hurdles Molecular Therapy 20:1298-304.

(56) References Cited

OTHER PUBLICATIONS

Zhong, Y.; Meng, F.; Deng, C.; Zhong, Z. Ligand-directed active tumor-targeting polymeric nanoparticles for cancer chemotherapy. Biomacromolecules, 2014, 15, 1955-69.

* cited by examiner

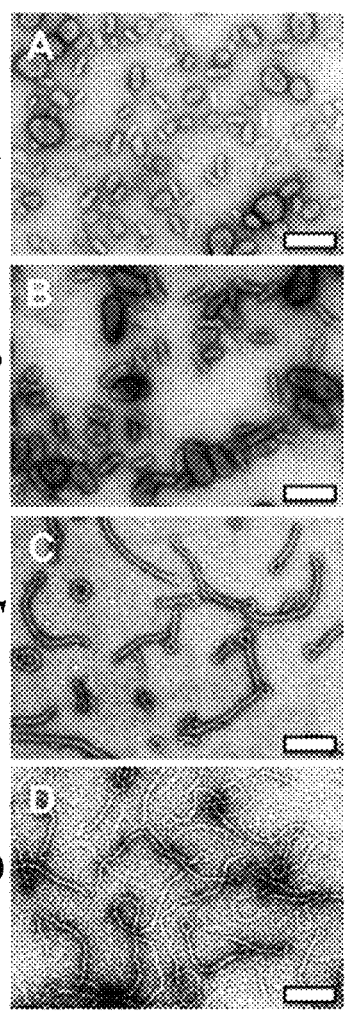
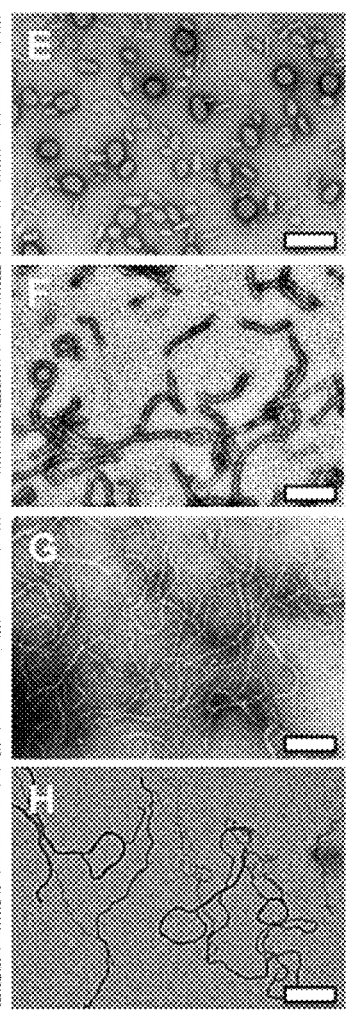
FIG. 7A  FIG. 7E
FIG. 7B  FIG. 7F
FIG. 7C  FIG. 7G
FIG. 7D  FIG. 7H

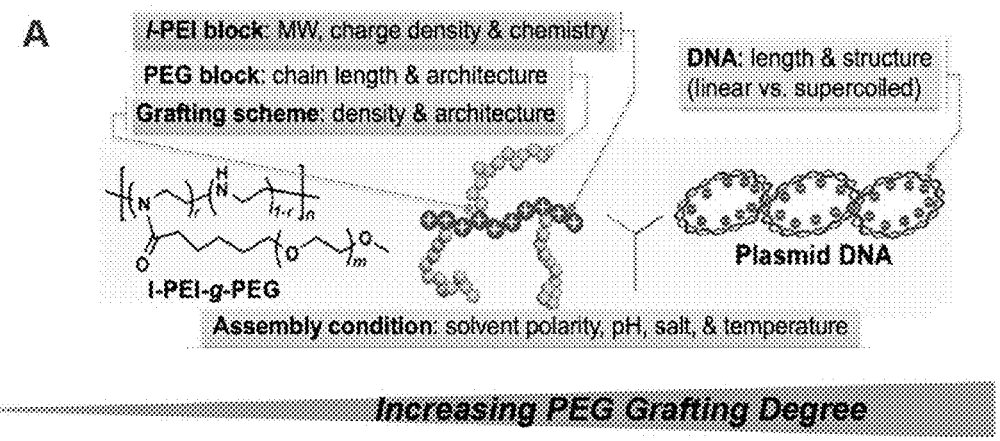
*FIG. 16A*
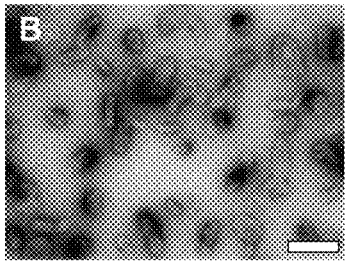
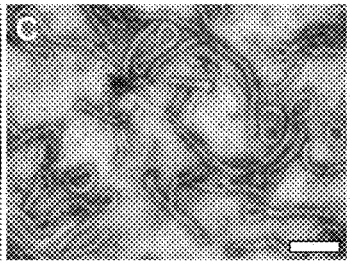
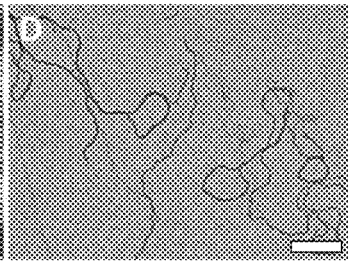
*FIG. 16B*  *FIG. 16C*  *FIG. 16D*
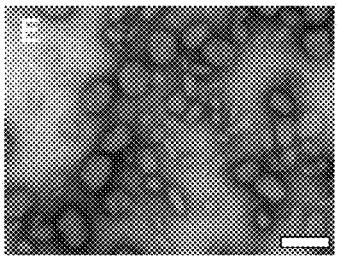
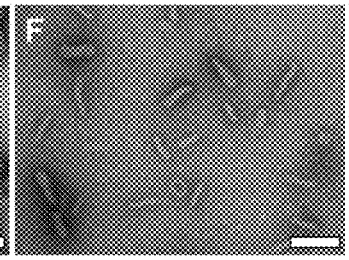
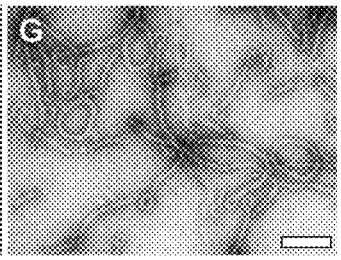
*FIG. 16E*  *FIG. 16F*  *FIG. 16G*

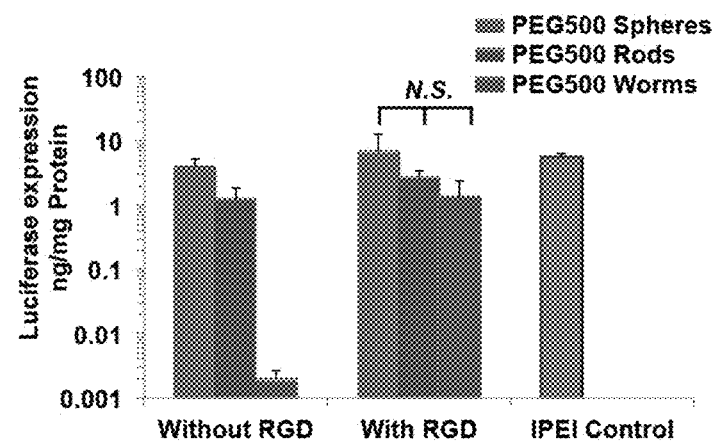
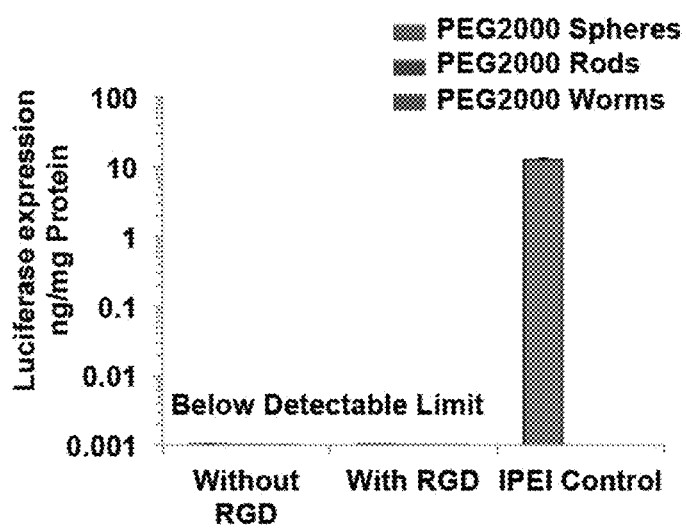
FIG. 19B

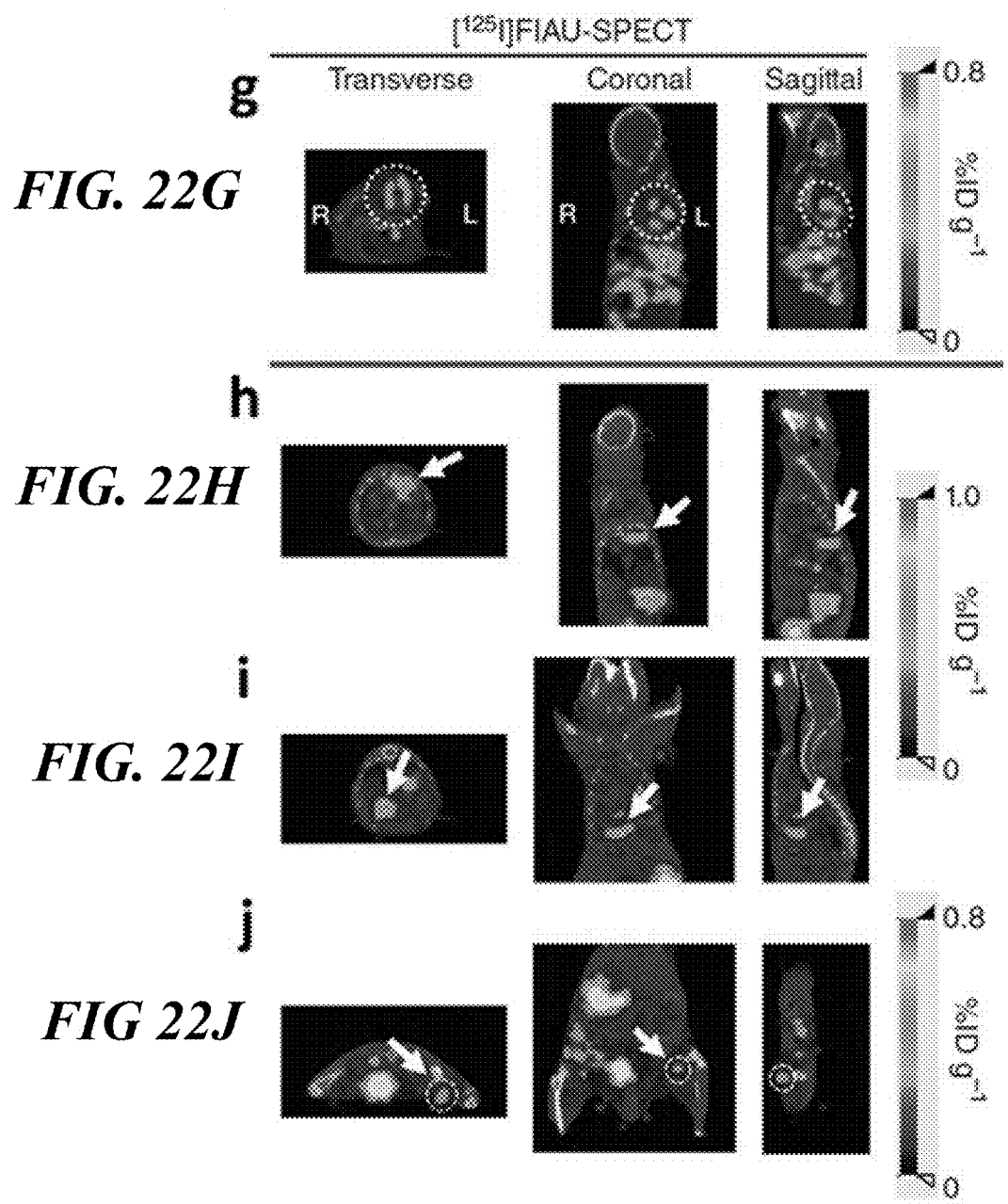

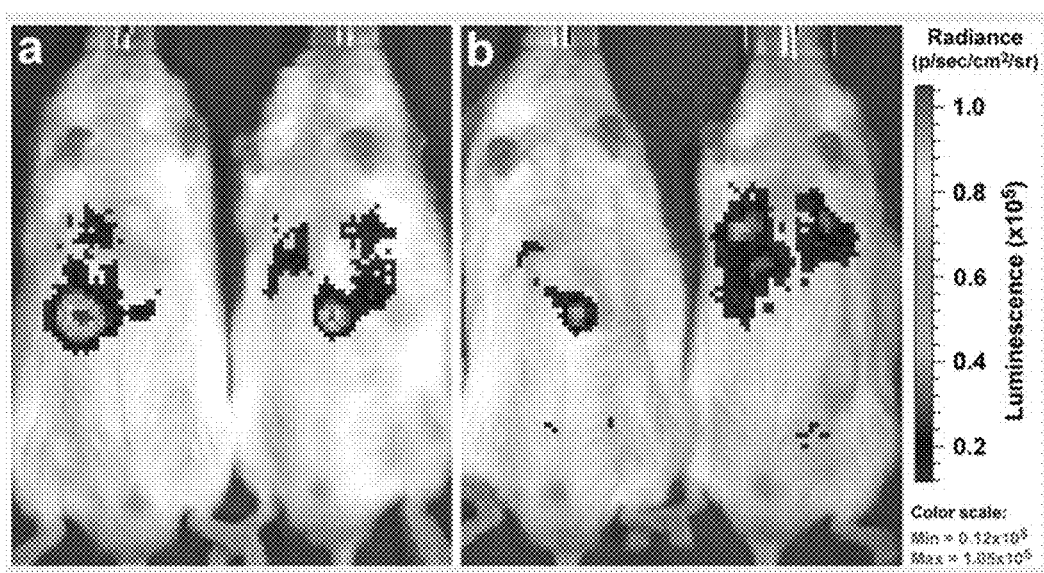
*FIG. 23A*   *FIG. 23B*

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Full sequence of laminin-derived peptide
<220> FEATURE:
<221> NAME/KEY: MOD_RES
<222> LOCATION: (1)..(1)
<223> OTHER INFORMATION: ACETYLATION

<400> SEQUENCE: 1

Cys Cys Arg Arg Tyr Val Val Leu Pro Arg Trp Leu Cys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Partial sequence of laminin-derived peptide

<400> SEQUENCE: 2

Arg Tyr Val Val Leu Pro Arg
1               5

<210> SEQ ID NO 3
<211> LENGTH: 5
<212> TYPE: PRT
```

```
<213> ORGANISM: Artificial Sequence
<220> FEATURE:
<223> OTHER INFORMATION: cell adhesion peptide YIGSR

<400> SEQUENCE: 3

Tyr Ile Gly Ser Arg
1               5
```

COMPOSITIONS OF NUCLEIC ACID-CONTAINING NANOPARTICLES FOR IN VIVO DELIVERY

CROSS-REFERENCE TO RELATED APPLICATIONS

This application is a continuation of U.S. Utility application Ser. No. 15/154,143 filed May 13, 2016, which claims the benefit of U.S. Provisional Application No. 62/161,546, filed May 14, 2015, the contents of which are incorporated herein by reference in their entirety.

FEDERALLY SPONSORED RESEARCH OR DEVELOPMENT

This invention was made with government support under U54CA151838, R01GM073937, and R21EB013274 awarded by the National Institutes of Health (NIH). The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00517_ST25.txt". The sequence listing is 1,059 bytes in size, and was created on Apr. 29, 2016. It is hereby incorporated by reference in its entirety.

BACKGROUND

Gene therapy remains an exciting strategy for therapeutic delivery in a number of disease applications, including cancer, metabolic disorders, and immune deficiencies (Ginn et al. (2013) *J. Gene Medicine* 15, 65-77; Hashida et al. (2001) *Advanced Drug Delivery Reviews* 52, 187-196; Pack et al. (2005) *Nature Reviews Drug Discovery* 4, 581-593; Peer et al. (2007) *Nature Nanotechnology* 2, 751-760). While viral-based methods have been the major gene carrier for these applications, evident by their use in approximately 70% of gene therapy clinical trials to date (Ginn et al. (2013) *J. Gene Medicine* 15, 65-77), safety concerns motivate the need to engineer alternative gene delivery systems (Yin et al. (2014) *Nature Reviews. Genetics* 15, 541-55).

Non-viral gene delivery strategies have been developed to overcome these significant limitations posed by viral vectors, namely the potential for immune responses, carcinogenesis, limited DNA payload size, and difficulty of large-scale vector production (Yin et al. (2014) *Nature Reviews. Genetics* 15, 541-55; Baum et al. (2006) *Human gene therapy* 17, 253-63; Bessis et al. (2004) *Gene Therapy* 11 Suppl 1, S10-7; Bouard et al. (2009) *British Journal of Pharmacology* 157, 153-65; Thomas et al. (2003) *Nature Reviews. Genetics* 4, 346-58). Nonviral vectors include naked DNA, liposome/DNA complexes, and polymer/DNA nanoparticles (Pack et al. (2005) *Nature Reviews Drug Discovery* 4:581-93; Wong et al. (2007) *Progress in Polymer Science* 32:799-837; Zhang et al. (2012) *Molecular Therapy* 20:1298-304). However, low transfection efficiency, particularly in vivo, limits the effectiveness of non-viral gene carriers (Zhang et al. (2012) *Molecular Therapy* 20:1298-304).

Nanoparticles comprise the main class of non-viral carriers, because of their ability to protect the DNA from degradation, target specific cells and tissues, and improve intracellular delivery of the payload (Pack et al. (2005) *Nature Reviews Drug Discovery* (2005) 4, 581-593; Bae and Park (2011) *J. of Controlled Release: Official Journal of the Controlled Release Society* 153, 198-205; Bertrand et al. (2014) *Advanced Drug Delivery Reviews* 66, 2-25; Chauhan and Jain (2013) *Nature Materials* 12, 958-62; Mura et al. (2013) *Nature Materials* 12, 991-1003; Park (2013) *ACS Nano* 7, 7442-7).

Cationic polymers are commonly used to condense plasmid DNA into nanoparticles through electrostatic interactions (Pack et al. (2005) *Nature Reviews Drug Discovery* 4, 581-593; Harada-Shiba et al. (2002) *Gene Therapy* 9, 407-14; Schaffert and Wagner (2008) *Gene Therapy* 15, 1131-8; Thomas and Klibanov (2003) *Applied Microbiology and Biotechnology* 62, 27-34). Polymeric nanoparticles effectively deliver genetic material in vitro, although their performance in vivo has demonstrated varying degrees of efficacy following intravenous administration, often showing transgene expression primarily in the lung (Davis (2002) *Current Opinion in Biotechnology* 13, 128-31; Goula et al. (1998) *Gene Therapy* 5, 1291-5). These mixed results are likely due to the interaction between cationic nanoparticles and serum components, leading to rapid aggregation, entrapment in capillary beds, and/or capture and clearance by the mononuclear phagocytic system (MPS) (Hsu and Uludag (2012) *J. of Drug Targeting* 20, 301-28; Jones et al. (2013) *Molecular Pharmaceutics*, 10, 4082-98; Morille et al. (2008) *Biomaterials* 29, 3477-96; Wiethoff et al. (2003) *J. of Pharm. Sci.* 92, 203-17). Of the numerous polymers developed for gene therapy applications, linear polyethylenimine (lPEI) remains one of the most popular due to its demonstrated efficiency in both cell culture and various animal models (Bonnet et al. (2008) *Pharm. Res.* 25, 2972-2982; Brissault et al. (2006) *Bioconjugate Chemistry*, 17, 759-765) particularly following local administration (Kang et al. (2009) *BMC Cancer* 9, 126; Lavergne et al. (2004) *J. of Immunology* 173, 3755-62; Hine et al. (2012) *Mol. Therapy: the Journal of the American Society of Gene Therapy* 20, 347-55), although it still suffers from aggregation issues in physiological media (Jere et al. (2009) *Expert Opinion on Drug Delivery* 6, 827-34; Patnaik and Gupta (2013) *Expert Opinion on Drug Delivery* 10, 215-228).

Surface coating of polymer/DNA nanoparticles has been widely used to improve their stability in biological environments, such as those encountered following systemic administration. One popular surface coating strategy has been PEGylation, typically through the use of block or graft copolymers comprised of a polycation chain and a polyethylene glycol (PEG) chain to form a core-shell, polyelectrolyte complex micelle assembly (Harada-Shiba et al. (2002) *Gene Therapy* 9, 407-14; Itaka and Kataoka (2011) *Current Gene Therapy* 11, 457-65). PEGylated nanoparticles demonstrate enhanced stability in serum, reducing aggregation, increasing circulation time, and decreasing MPS clearance after intravenous injection (Nomoto et al. (2011) *Journal of Controlled Release: Official Journal of the Controlled Release Society* 151, 104-109; Alexis et al. (2008) *Molecular Pharmaceutics* 5, 505-15; Petersen et al. (2002) Bioconjugate Chemistry 13, 845-54).

In addition to the stability improvements conferred by PEGylation, recent work has highlighted the importance PEG in the ability to control the shape of polymer/DNA nanoparticles for gene therapy applications. For example, using a PEG-polyphosphoramidate (PPA) block copolymer, DNA nanoparticle shape can be controlled through variation of solvent polarity during nanoparticle formation, ranging from spherical to rod-like and worm-like shapes (Jiang et al. (2013) *Advanced Materials* 25, 227-232). Experimental studies and molecular dynamics simulations highlighted the important role of PEG in shape formation, as particles prepared without the PEG block did not demonstrate an ability to tune the shape of polymer/DNA micelles. Similar results have been recently observed for PEG-polycation graft copolymers, including PPA and lPEI, where increasing the PEG grafting degree led to shape variation from more condensed spherical and short rod shapes to longer rod and worm-like shapes (Williford et al. (2014) *Journal of Materials Chemistry* 2, 8106-8109; Wei et al. (2015) *ACS Biomaterials Science & Engineering*).

While PEGylation provides significant benefits during circulation and transport of nanoparticle delivery systems, several drawbacks exist for successful gene delivery both in vitro and in vivo. The dense PEG layer and accompanying near-neutral surface charge significantly decreases interaction with the target cells of interest (Pozzi et al. (2014) *Nanoscale* 6, 2782-2792; Hatakeyama et al. (2011) *Adv. Drug Deliv. Rev.* 63, 152-60; Ge et al. (2014) *Biomaterials* 35, 3416-3426). Because of the lowered cell uptake, transgene expression mediated by PEGylated nanoparticles has been observed to drop by several orders of magnitude (Hatakeyama et al. (2011) *Adv. Drug Deliv. Rev.* 63, 152-60).

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: ncbi.nlm.nih.gov/omim/ and in Online Mendelian Inheritance in Animals (OMIA), a database of genes, inherited disorders and traits in animal species (other than human and mouse), at world wide web omia.angis.org.au/contact-.shtml. The Kinetochore, Springer, 2009. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In one aspect, the presently disclosed subject matter provides a polymeric micellar nanoparticle composition, comprising: (a) a block or graft copolymer comprising at least one polycationic polymer and at least one polyethylene glycol (PEG) polymer having an average molecular weight less than 1 kDa; and (b) at least one nucleic acid; wherein the graft or block copolymer and the at least one nucleic acid are complexed and condensed into a shaped micellar nanoparticle that is stable in biological media.

In some embodiments, (i) the at least one PEG polymer has a molecular weight ranging from about 400 Da to about 1 kDa; or (ii) the at least one PEG polymer has a molecular weight ranging from about 500 Da to about 700 Da; or (iii) the copolymer is a graft copolymer and the at least one PEG polymer has a graft density ranging from about 0.25 mol % to about 10 mol %; or (iv) the at least one PEG polymer is terminated with a functional group selected from the group consisting of a terminal acrylate group, a terminal alkoxy group, a terminal amino group, terminal carboxyl group, a terminal hydroxyl group, a terminal maleimide group, a terminal methacrylate group, a terminal methoxy group, a terminal 2-pyridyldithio (SPDP) group, a terminal thiol group, a negatively charged terminal group, or amphoteric group, or combinations thereof.

In some embodiments, the shaped micellar nanoparticle is selected from the group consisting of a spherically-shaped micellar nanoparticle, a rod-shaped micellar nanoparticle, and a worm-shaped micellar nanoparticle.

In some embodiments, the composition further comprises a ligand conjugated to the at least one PEG polymer and/or the functional group. In some embodiments, (i) the ligand is selected from the group consisting of a diagnostic agent, an imaging agent, a targeting agent, a theranostic agent, a therapeutic agent, and combinations thereof; or (ii) the ligand is selected from the group consisting of a DNA, RNA, polypeptide, antibody, antibody fragment, antigen, carbohydrate, protein, peptide, enzyme, amino acid, hormone, steroid, vitamin, drug, virus, polysaccharide, lipid, lipopolysaccharide, glycoprotein, lipoprotein, nucleoprotein, oligonucleotide, immunoglobulin, albumin, hemoglobin, coagulation factor, peptide hormone, protein hormone, non-peptide hormone, interleukin, interferon, cytokine, peptides comprising a tumor-specific epitope, cell, cell-surface molecule, cell adhesion peptide, cell-binding peptide, cell receptor ligand, small organic molecule, small organometallic molecule, nucleic acid, oligonucleotide, transferrin, metabolites thereof, and antibodies or agents that bind to any of the above substances; or (iii) the ligand is detectable using an imaging modality selected from the group consisting of bioluminescence imaging, fluorescence imaging, magnetic resonance imaging (MRI), positron emission tomography (PET), x-ray computed tomography (CT), single-photon emission computed tomography (SPECT), and combinations thereof; or (iv) the ligand comprises a peptide comprising the amino acid sequence Ac-CCRRYVVLPRWLC (SEQ ID NO: 1), cyclic RGD-thiol peptide (cRGD), or a peptide comprising the amino acid sequence YIGSR (SEQ ID NO: 3); or (v) the ligand comprises a moiety that binds to a tumor-specific antigen; or (vi) the ligand comprises a prostate-specific membrane antigen (PSMA)-binding moiety.

In some embodiments, (i) the at least one polycationic polymer is selected from the group consisting of linear polyethylenimine (LPEI), poly-lysine, poly-arginine, poly-histidine, chitosan, branched PEI, a poly (beta-aminoester), a polyphosphoester (PPE), and polyphosphoramidate (PPA); or (ii) the at least one polycationic polymer is LPEI; or (iii) the at least one polycationic polymer is not branched PEI; or (iv) the graft copolymer is not a branched PEI(25 kDa)-g-linear PEG(550 Da)$_n$ copolymer, wherein n is the average number of PEG blocks per one PEI macromolecule and n is equal to 35.

In some embodiments, (i) the LPEI has a molecular weight ranging from about 2 kDa to about 50 kDa; or (ii) the LPEI has a molecular weight of about 22 kDa.

In some embodiments, (i) the at least one nucleic acid has a length ranging from about 10 bases to about 10 kilobases (kb); or (ii) the at least one nucleic acid is selected from the group consisting of an antisense oligonucleotide, cDNA, genomic DNA, guide RNA, plasmid DNA, vector DNA, mRNA, miRNA, piRNA, shRNA, and siRNA; or (iii) the at least one nucleic acid comprises an expression vector encoding at least one reporter gene operably linked to a promoter; or (iv) the at least one nucleic acid comprises an expression vector encoding at least one antigen epitope operably linked to a promoter.

In some embodiments, (i) the reporter gene is selected from the group consisting of a bioluminescent reporter gene, a fluorescent reporter gene, a PET reporter gene, and combinations thereof; or (ii) the promoter is selected from the group consisting of a constitutively active promoter, an inducible promoter, a tissue-specific promoter, and a tumor-specific promoter; or (iii) the expression vector further comprises a therapeutic gene; or (iv) the expression vector further comprises an antigen gene. In some embodiments, (i) the therapeutic gene is selected from the group consisting of a cytotoxic gene, an immunomodulator gene, a suicide gene, and a tumor suppressor gene; or (ii) the antigen gene encodes at least one antigen against infectious diseases, allergens, or cancer cells.

In some embodiments, the composition further comprises a therapeutic agent or a chemotherapeutic agent.

In some embodiments, the micellar nanoparticle composition targets at least one target cancer cell. In some embodiments, (i) the cancer cell comprises a metastatic cancer cell; or (ii) the cancer cell is selected from the group consisting of a breast cancer cell, a cervical cancer cell, a melanoma cancer cell, and a prostate cancer cell.

In some embodiments, the micellar nanoparticle composition exhibits a transfection efficiency of the at least one target cancer cell of between 10-fold and 100-fold greater than a micellar nanoparticle composition comprising a PEG polymer having an average molecular weight greater than 1 kDa.

In certain aspects, the presently disclosed subject matter provides a method for preparing a polymeric micellar nanoparticle composition comprising a block or graft copolymer comprising at least one polycationic polymer and at least one polyethylene glycol (PEG) polymer having an average molecular weight less than 1 kDa; and at least one nucleic acid; wherein the graft or block copolymer and the at least one nucleic acid are complexed and condensed into a shaped micellar nanoparticle that is stable in biological media, the method comprising: (a) mixing a first solution comprising the block or graft copolymer together with a second solution comprising the at least one nucleic acid to form a third solution comprising the block or graft copolymer and the at least one nucleic acid; and (b) allowing the block or graft copolymer and the at least one nucleic acid to self-assemble into the polymeric micellar nanoparticle.

In some embodiments, the presently disclosed subject matter provides a transfection agent for transfecting a cell with at least one nucleic acid, the transfection agent comprising a polymeric micellar nanoparticle composition comprising a block or graft copolymer comprising at least one polycationic polymer and at least one polyethylene glycol (PEG) polymer having an average molecular weight less than 1 kDa; and at least one nucleic acid; wherein the graft or block copolymer and the at least one nucleic acid are complexed and condensed into a shaped micellar nanoparticle that is stable in biological media, wherein the polymeric micellar nanoparticle composition is prepared by the method comprising: (a) mixing a first solution comprising the block or graft copolymer together with a second solution comprising the at least one nucleic acid to form a third solution comprising the block or graft copolymer and the at least one nucleic acid; and (b) allowing the block or graft copolymer and the at least one nucleic acid to self-assemble into the polymeric micellar nanoparticle. In some embodiments, the transfection agent modulates expression of at least one gene in a cell, tissue, or subject.

In some embodiments, the method for targeting at least one metastatic cancer cell in a subject comprises administering the transfection agent to a subject, wherein the polymeric micellar nanoparticle composition comprises a ligand that binds to a tumor-specific antigen on the surface of the at least one metastatic cancer cell, and wherein the ligand binds to the tumor-specific antigen on the surface of the at least one metastatic cancer cell after administration of the transfection agent to the subject, thereby targeting the at least one metastatic cancer cell in the subject. In some embodiments, (i) targeting the at least one metastatic cancer cell comprises treating a metastatic cancer in the subject; or (ii) targeting the at least one metastatic cancer cell comprises detecting, diagnosing, and/or imaging a metastatic cancer in the subject.

In some embodiments, the polymeric micellar nanoparticle composition further comprises a chemotherapeutic agent and/or at least one nucleic acid encoding a therapeutic gene that inhibits the growth, proliferation and/or survival of the at least one metastatic cancer cell. In some embodiments, the polymeric micellar nanoparticle composition further comprises an imaging agent and/or at least one nucleic acid encoding a reporter gene operably linked to a tumor-specific promoter. In some embodiments, the reporter gene is selected from the group consisting of a bioluminescent reporter gene, a fluorescent reporter gene, a CT reporter gene, an MRI reporter gene, a PET reporter gene, a SPECT reporter gene, and combinations thereof.

In some embodiments, targeting at least one metastatic cancer cell in a subject further comprises imaging the subject after administering the transfection agent using an imaging modality selected from the group consisting of bioluminescent imaging, fluorescent imaging, CT, MRI, PET, SPECT, X-ray, and combinations thereof.

In other aspects, the presently disclosed subject matter provides a method for treating a disease or condition, the method comprising administering to a subject in need of treatment thereof, a polymeric micellar nanoparticle composition comprising a block or graft copolymer comprising at least one polycationic polymer and at least one polyethylene glycol (PEG) polymer having an average molecular weight less than 1 kDa; and at least one nucleic acid; wherein the graft or block copolymer and the at least one nucleic acid are complexed and condensed into a shaped micellar nanoparticle that is stable in biological media, or a pharmaceutical composition thereof, in an amount effective for treating the disease or condition.

In some aspects, the presently disclosed subject matter provides a method for preventing a disease or condition, the method comprising administering to a subject in need of prophylactic treatment thereof, a polymeric micellar nanoparticle composition comprising a block or graft copolymer comprising at least one polycationic polymer and at least one polyethylene glycol (PEG) polymer having an average molecular weight less than 1 kDa; and at least one nucleic acid; wherein the graft or block copolymer and the at least one nucleic acid are complexed and condensed into a shaped micellar nanoparticle that is stable in biological media, or a pharmaceutical composition thereof, in an amount effective for preventing the disease or condition.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
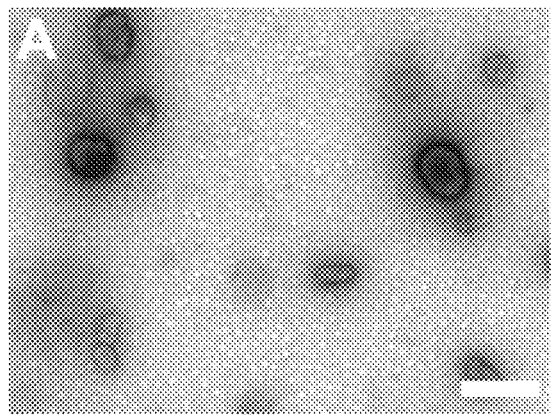
Figure 1B:
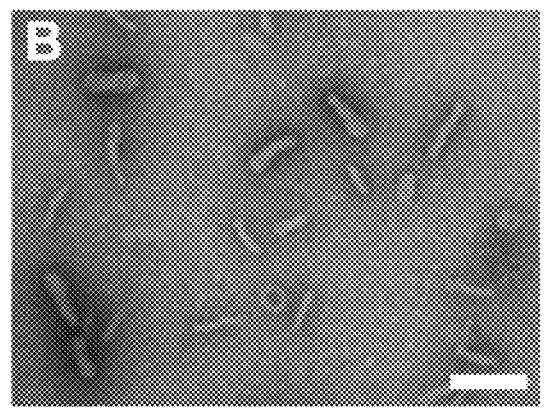
Figure 1C:
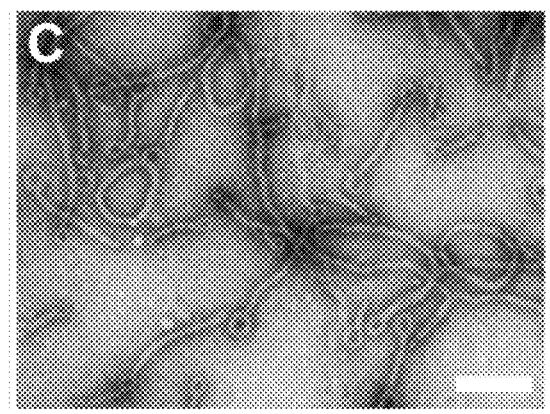
Figure 2:
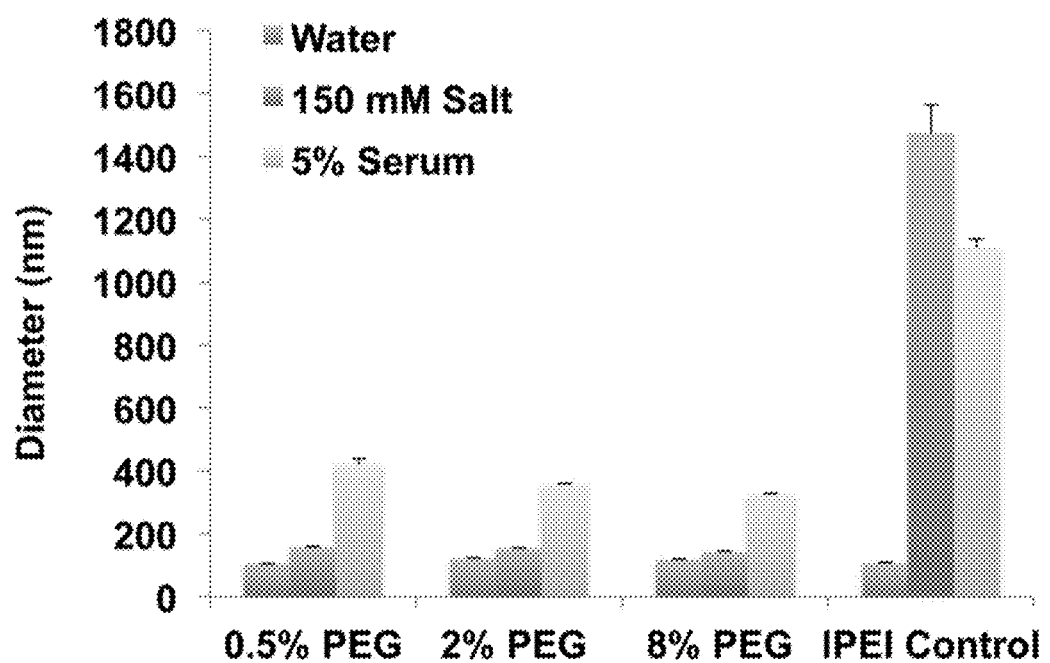
Figure 3:
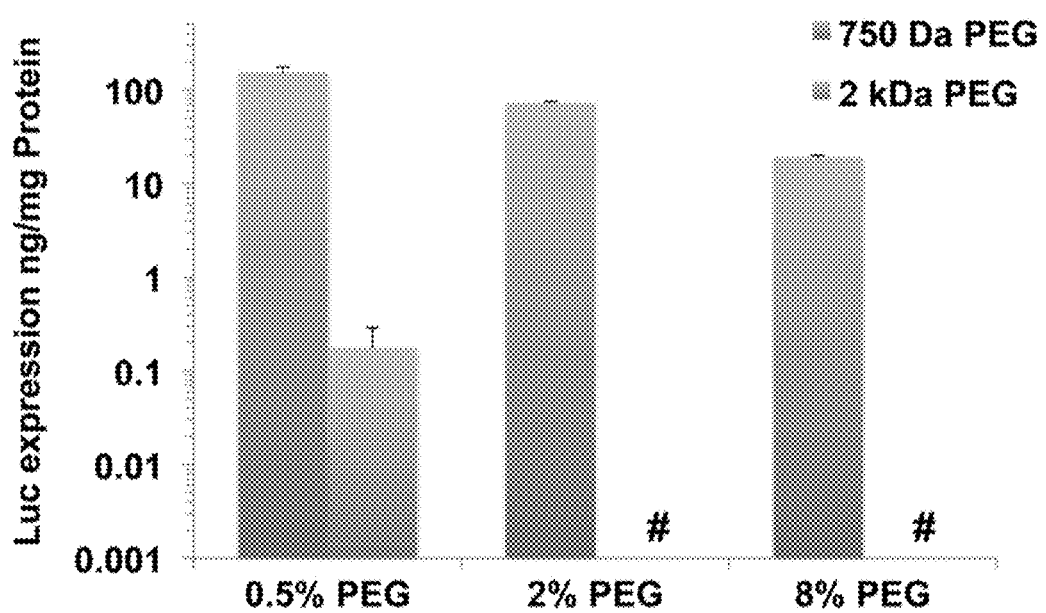
Figure 4:
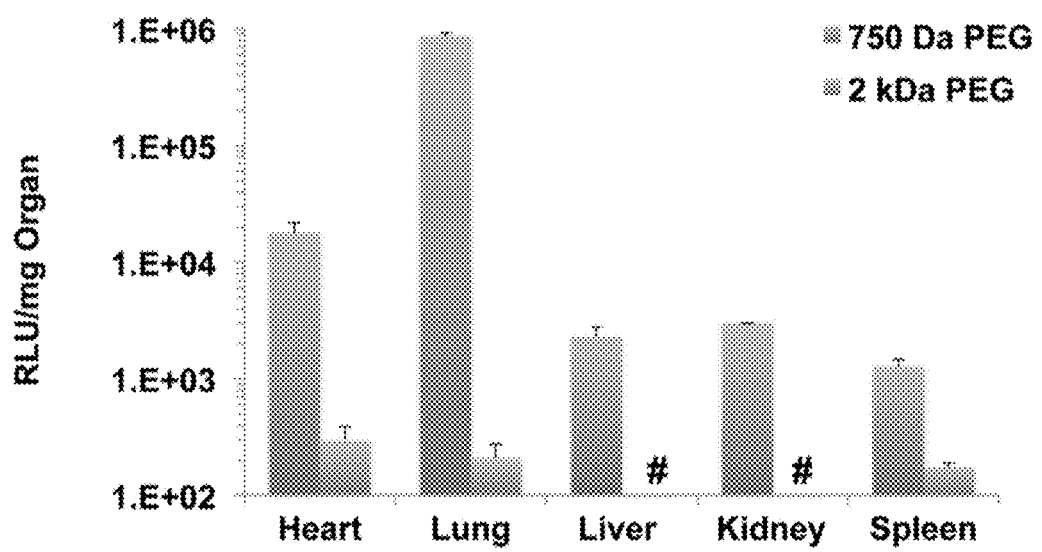
Figure 5A:
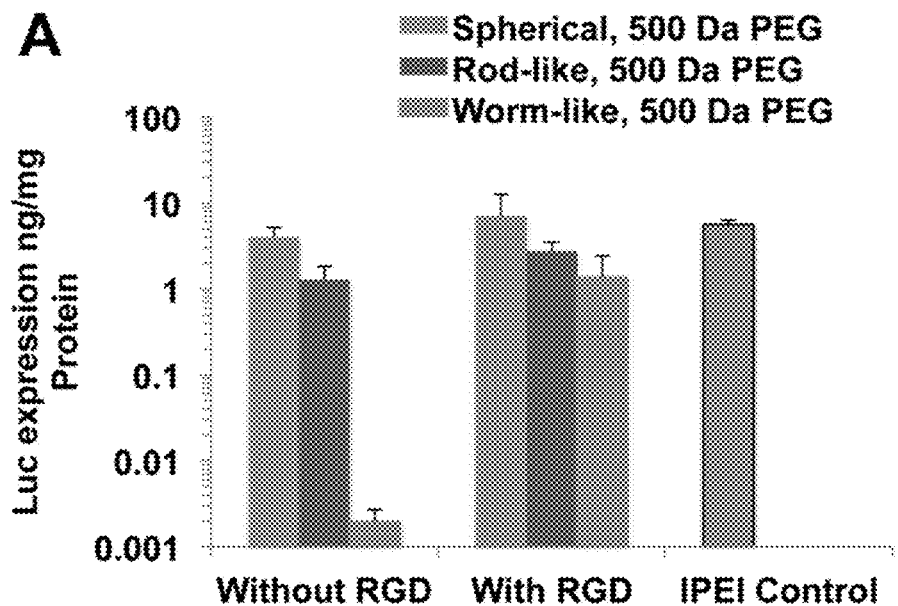
Figure 5B:
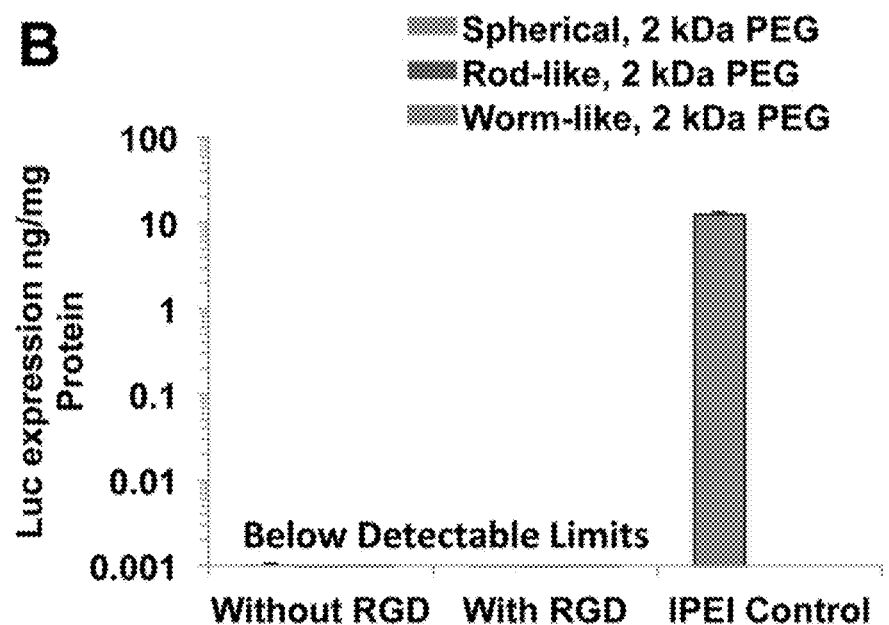
Figure 6A:
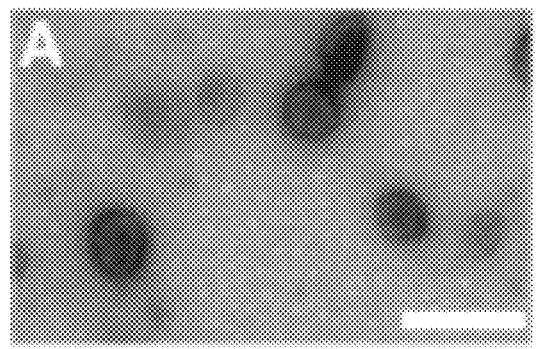
Figure 6B:
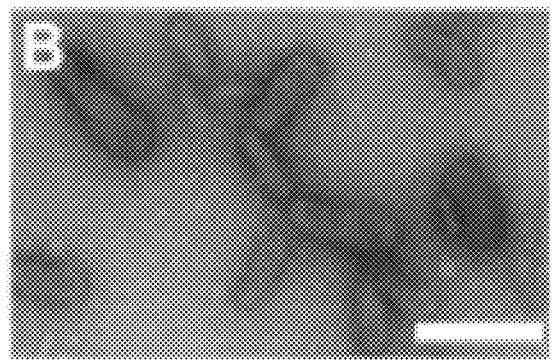
Figure 6C:
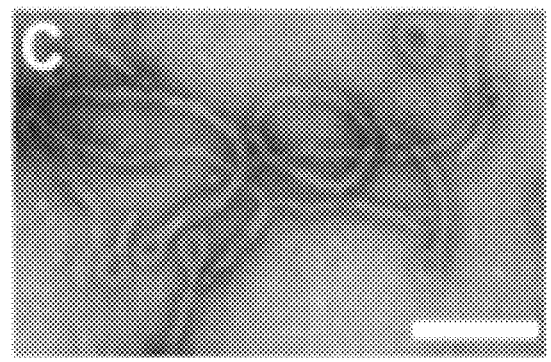
Figure 6D:
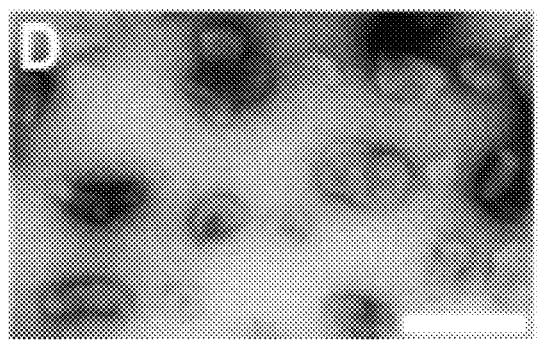
Figure 6E:
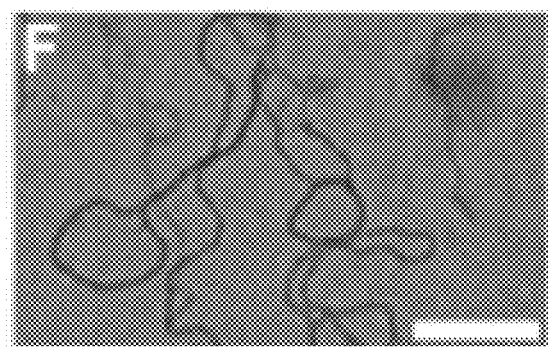
Figure 6F:
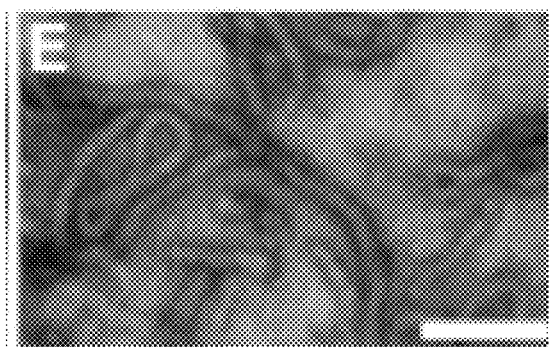
Figure 6G:
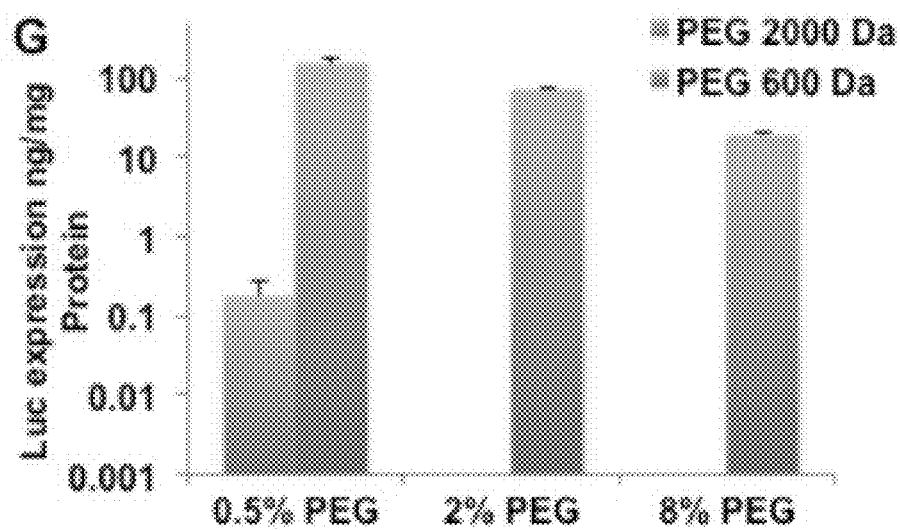
Figure 6H:
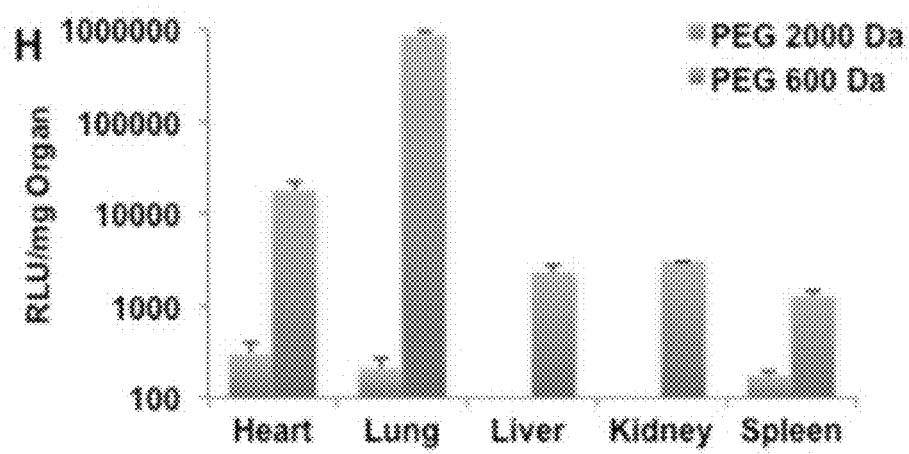
Figure 8A:
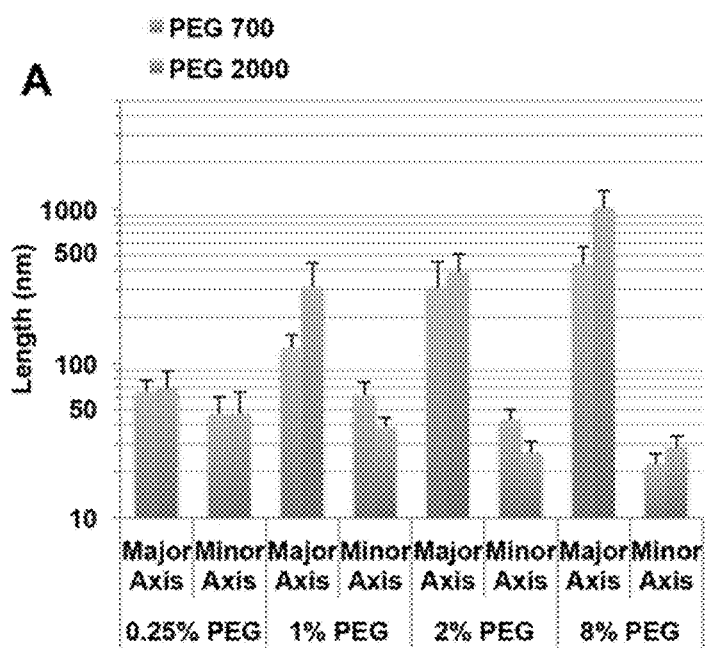
Figure 8B:
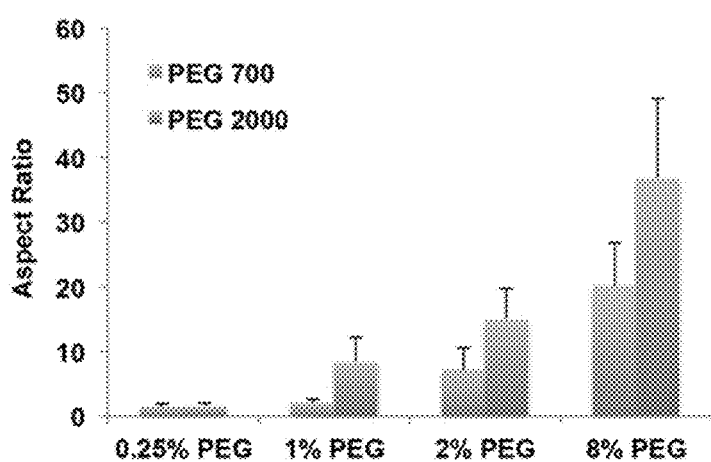
Figure 10A:
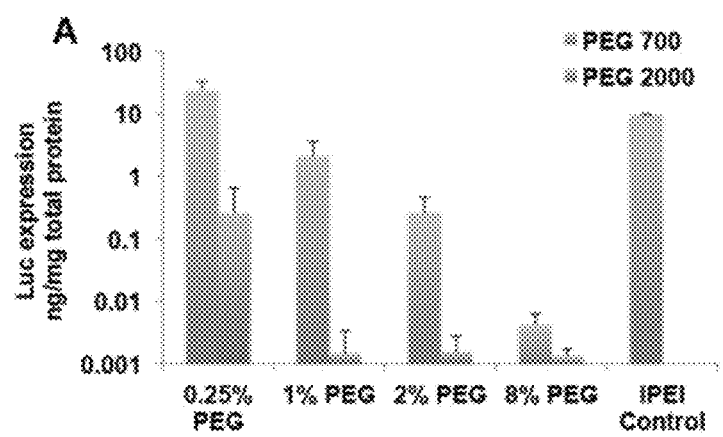
Figure 10B:
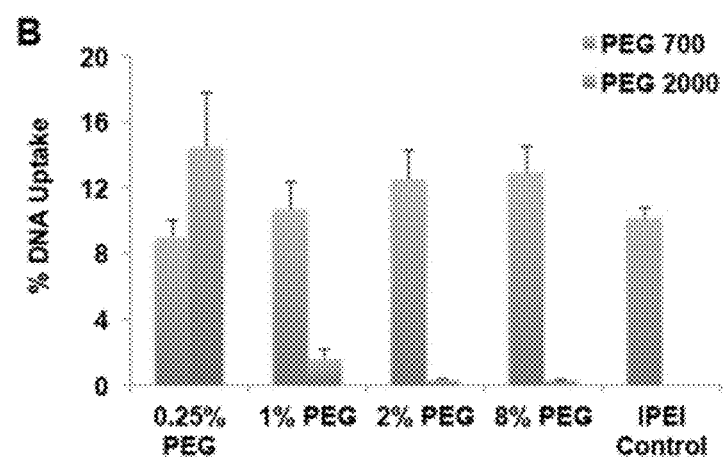
Figure 11A:
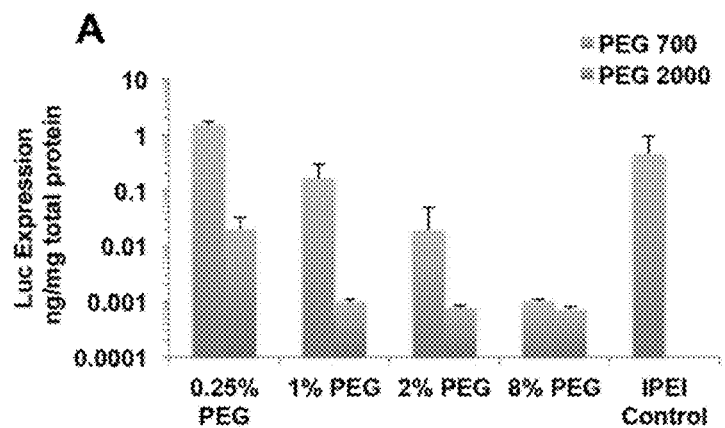
Figure 11B:
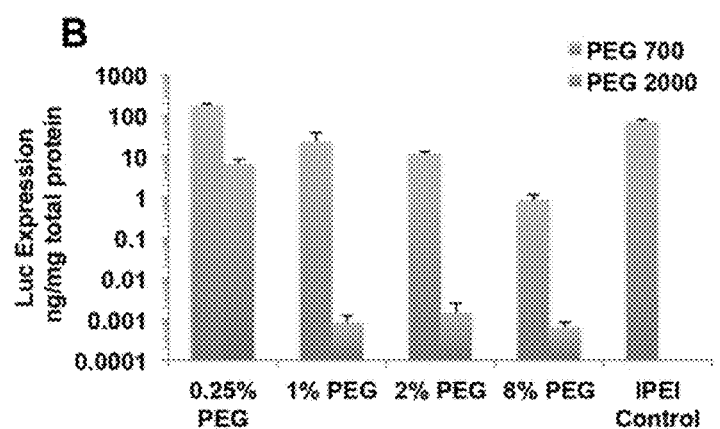
Figure 12A:
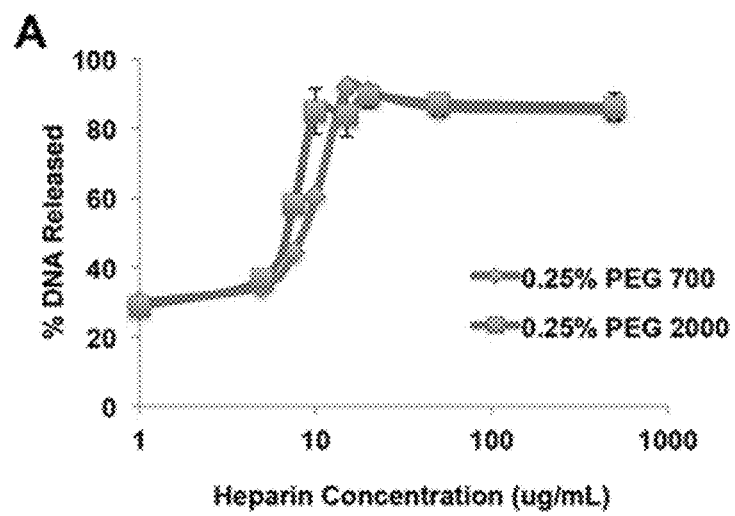
Figure 12B:
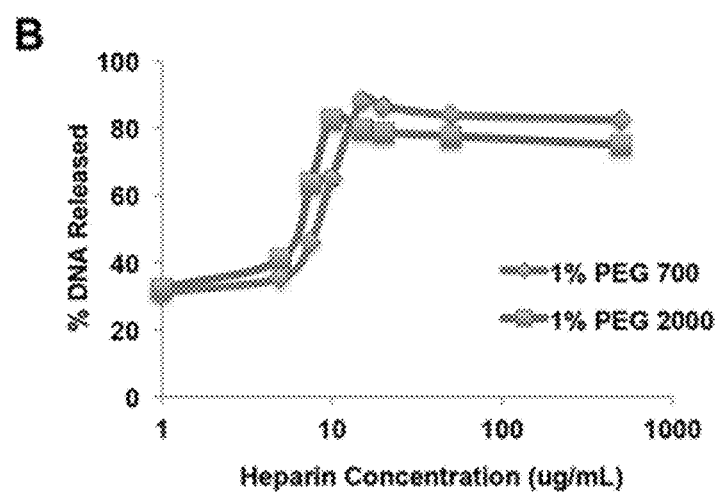
Figure 12C:
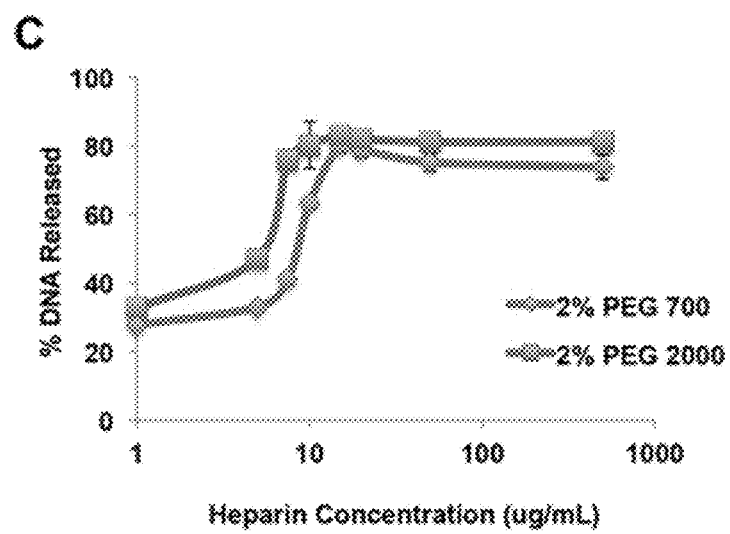
Figure 12D:
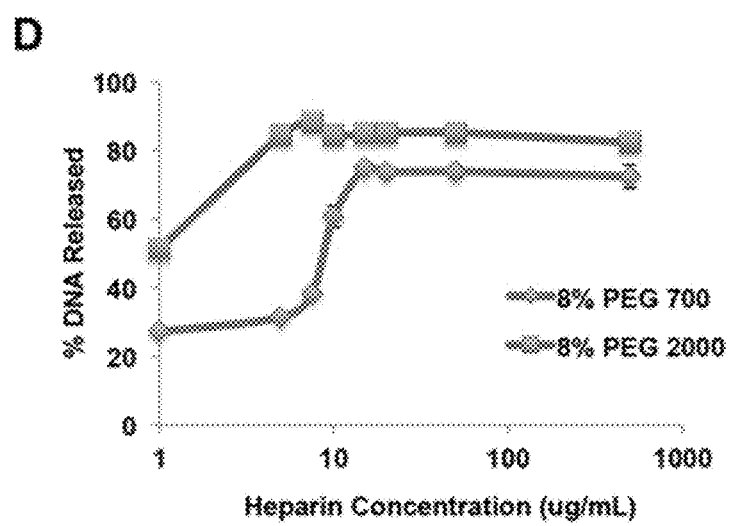
Figure 13:
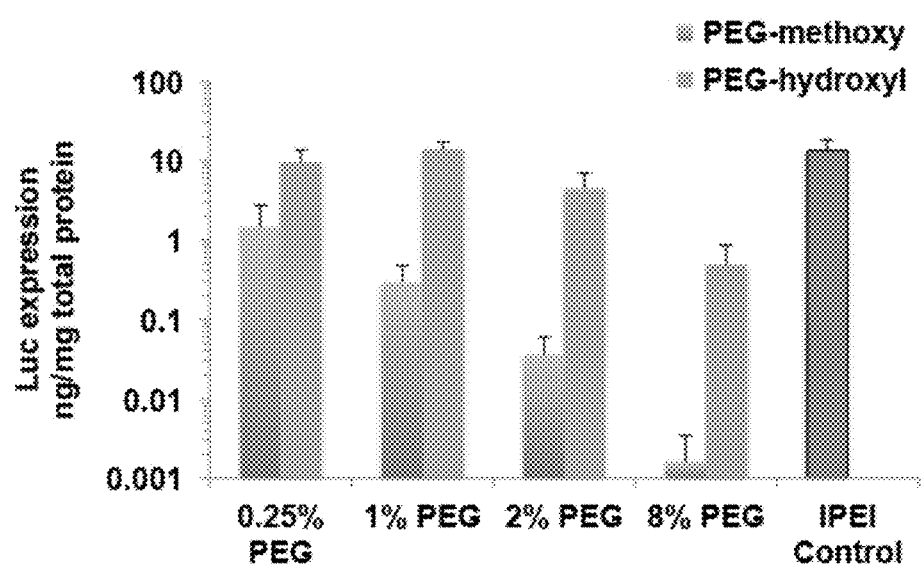
Figure 14A:
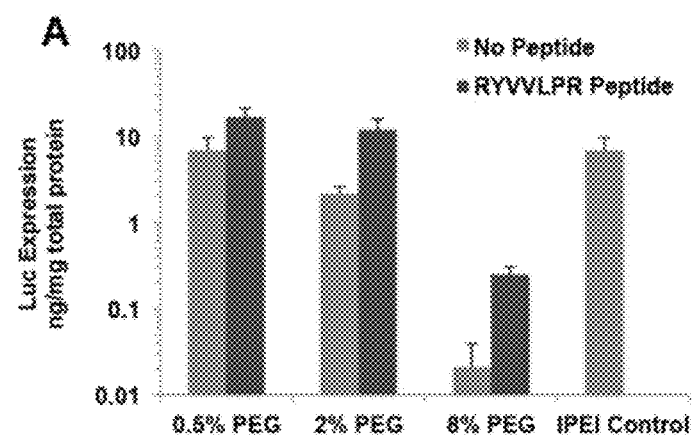
Figure 14B:
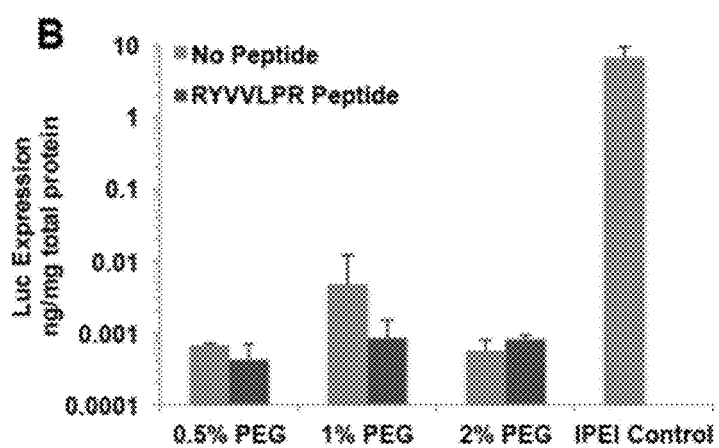
Figure 15A:
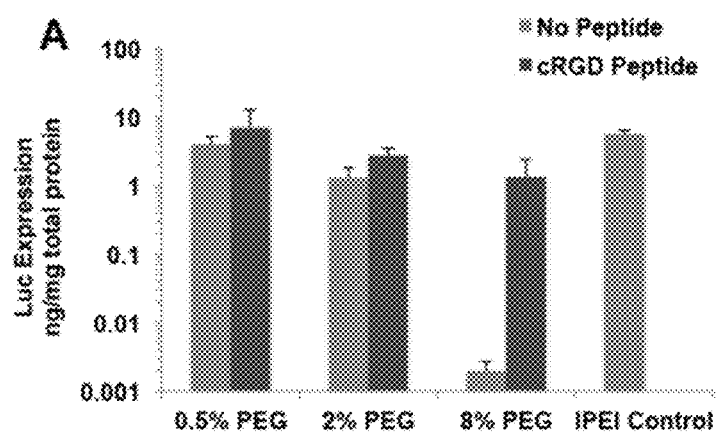
Figure 15B:
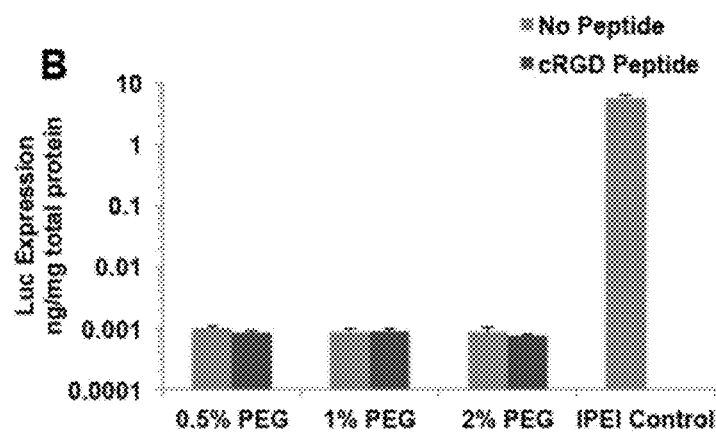

Having thus described the presently disclosed subject matter in general terms, reference will now be made to the accompanying Figures, which are not necessarily drawn to scale, and wherein:

FIG. 1A, FIG. 1B, and FIG. 1C show TEM images of $lPEI_{22k}$-g-$PEG_{600}$/DNA micelles prepared with 0.5% $PEG_{600}$ (FIG. 1A), 2% $PEG_{600}$ (FIG. 1B), and 8% $PEG_{600}$ (FIG. 1C). All scale bars represent 200 nm;

FIG. 2 shows the stability of $lPEI_{22k}$-g-$PEG_{600}$/DNA micelles with different PEG grafting degrees following 30 minute incubation in 150 mM salt or 5% (volume/volume) FBS, as compared to $lPEI_{22k}$/DNA control nanoparticles;

FIG. 3 shows in vitro transfection of HeLa cells 48 hours following treatment of $lPEI_{22k}$-g-$PEG_{750}$/DNA nanoparticles and of $lPEI_{22k}$-g-$PEG_{2000}$/DNA nanoparticles at different PEG grafting degrees. # indicates that expression was below detectable limit of the assay;

FIG. 4 shows in vivo transfection of Balb/c mice in major organs 2 days following treatment of $lPEI_{22k}$-g-$PEG_{750}$/DNA nanoparticles and of $lPEI_{22k}$-g-$PEG_{2000}$/DNA nanoparticles prepared with 0.25% PEG grafting degree. # indicates that expression was below detectable limit of the assay;

FIG. 5A and FIG. 5B show in vitro transfection of MDA-MB-231 cells overexpressing αvβ3 integrin 48 hours following treatment of $lPEI_{22k}$-g-PEG500/DNA nanoparticles (FIG. 5A) and $lPEI_{22k}$-g-$PEG_{2000}$/DNA nanoparticles (FIG. 5B) with different shapes with and without conjugation of cyclic RGD cell adhesion peptide;

FIG. 6A, FIG. 6B, FIG. 6C, FIG. 6D, FIG. 6E, FIG. 6F, FIG. 6G, and FIG. 6H show TEM images of lPEI-g-$PEG_{600}$/DNA nanoparticles (FIG. 6A, FIG. 6B, and FIG. 6C) and lPEI-g-$PEG_{2000}$/DNA nanoparticles (FIG. 6D, FIG. 6E, and FIG. 6F) with 0.5% (FIG. 6A and FIG. 6D), 2% (FIG. 6B and FIG. 6E), and 8% (FIG. 6C and FIG. 6F) PEG grafting degrees. All scale bars represent 200 nm. In vitro transfection efficiency of lPEI-g-PEG/DNA nanoparticles with varying PEG molecular weight and grafting degrees (FIG. 6G); In vivo transfection efficiency of lPEI-g-PEG (0.5%)/DNA nanoparticles in Balb/c mice (FIG. 6H);

FIG. 7A, FIG. 7B, FIG. 7C, FIG. 7D, FIG. 7E, FIG. 7F, FIG. 7G, and FIG. 7H show TEM images of $lPEI$-g-$PEG_{7H}$/DNA nanoparticles (FIG. 7A, FIG. 7B, FIG. 7C and FIG. 7D) and $lPEI$-g-$PEG_{2K}$/DNA nanoparticles (FIG. 7E, FIG. 7F, FIG. 7G and FIG. 7H) prepared with 0.25% PEG grafting degree (FIG. 7A and FIG. 7E), 1% PEG grafting degree (FIG. 7B and FIG. 7F), 2% PEG grafting degree (FIG. 7C and FIG. 7G), and 8% PEG grafting degree (FIG. 7D and FIG. 7H). All scale bars=200 nm;

FIG. 8A and FIG. 8B show average major and minor axis lengths (FIG. 8A) and aspect ratios (FIG. 8B) of $lPEI$-g-$PEG_{7H}$/DNA nanoparticles and $lPEI$-g-$PEG_{2K}$/DNA nanoparticles prepared with different grafting degrees. Each bar represents mean±standard division (n>100 particles);

FIG. 9A, FIG. 9B, FIG. 9C, and FIG. 9D show zeta potential of $lPEI$-g-$PEG_{7H}$/DNA (FIG. 9A) and $lPEI$-g-$PEG_{2K}$/DNA nanoparticles (FIG. 9B) in DI water and 150 mM NaCl solution. Each bar represents mean±standard division (n=3). Size of $lPEI$-g-$PEG_{7H}$/DNA (FIG. 9C) and $lPEI$-g-$PEG_{2K}$/DNA (FIG. 9D) nanoparticles after 15 min incubation in DI water, 150 mM NaCl, and 5% serum, respectively. Each bar represents mean±standard division (n=3);

FIG. 10A and FIG. 10B show transfection efficiency (FIG. 10A) and cellular uptake efficiency (FIG. 10B) of $lPEI$-g-$PEG_{7H}$/DNA and $lPEI$-g-$PEG_{2K}$/DNA nanoparticles in PC3 cells. Each bar represents mean±standard division (n=3);

FIG. 11A and FIG. 11B show the transfection efficiency of $lPEI$-g-$PEG_{7H}$/DNA and $lPEI$-g-$PEG_{2K}$/DNA nanoparticles in MDA-MB-231 cells (FIG. 11A) and HeLa cells (FIG. 11B). Each bar represents mean±standard division (n=3);

FIG. 12A, FIG. 12B, FIG. 12C, and FIG. 12D show DNA release from $lPEI$-g-$PEG_{7H}$/DNA and $lPEI$-g-$PEG_{2K}$/DNA nanoparticles prepared with 0.25% PEG grafting degree (FIG. 12A), 1% PEG grafting degree (FIG. 12B), 2% PEG grafting degree (FIG. 12C), and 8% PEG grafting degree (FIG. 12D) after treatment with increasing concentrations of heparin sulfate in 150 mM NaCl solution for 15 min. Each point represents mean±standard division (n=3);

FIG. 13 shows the transfection efficiency of lPEI-g-PEG/DNA nanoparticles bearing methoxy-terminated or hydroxyl-terminated $PEG_{6H}$ corona in PC3 cells. Each bar represents mean±standard division (n=3);

FIG. 14A and FIG. 14B show the transfection efficiency in PC3 cells mediated by $lPEI$-g-$PEG_{5H}$/DNA (FIG. 14A) and $lPEI$-g-$PEG_{2K}$/DNA (FIG. 14B) nanoparticles with and without surface-conjugated cell binding peptide RYVVLPR (SEQ ID NO:2). Each bar represents mean±standard division (n=3);

FIG. 15A and FIG. 15B show the transfection efficiency of $lPEI$-g-$PEG_{5H}$/DNA (FIG. 15A) and $lPEI$-g-$PEG_{2K}$/DNA (FIG. 15B) nanoparticles in MDA-MB-231-$\alpha_v\beta_3^+$ cells comparing nanoparticles with and without conjugation of cell binding peptide cRGD. Each bar represents mean±standard division (n=3);

FIG. 16A, FIG. 16B, FIG. 16C, FIG. 16D, FIG. 16E, FIG. 16F, and FIG. 16G show a schematic illustration of the critical factors for shape control in lPEI-g-PEG/DNA micelle assembly (FIG. 16A) and TEM images showing the shape variations at 0.5% PEG grafting degree (FIG. 16B and FIG. 16E), 2% PEG grafting degree (FIG. 16C and FIG.

Figure 17A:
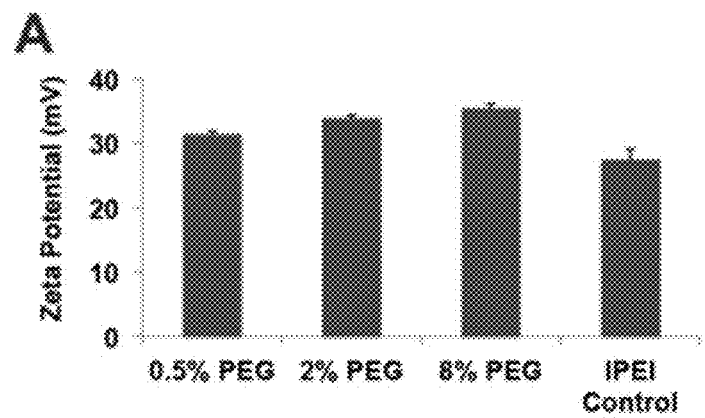
Figure 17B:
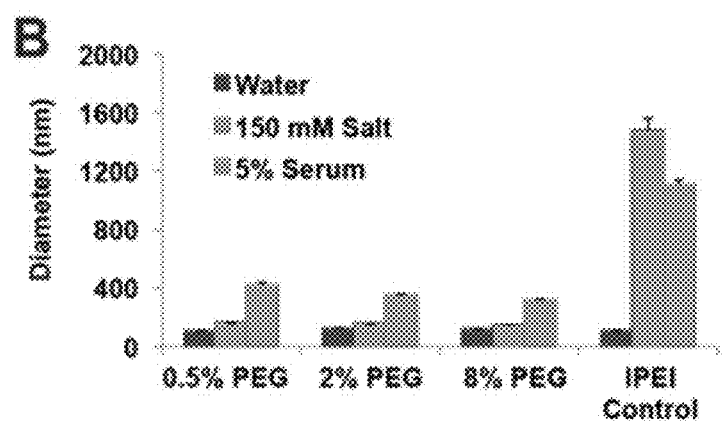
Figure 18A:
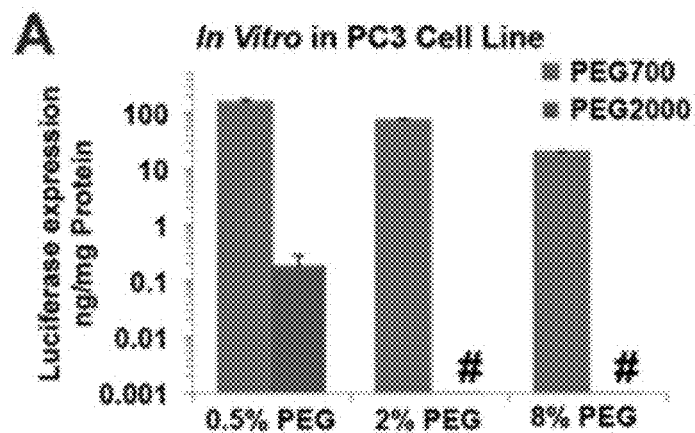
Figure 18B:
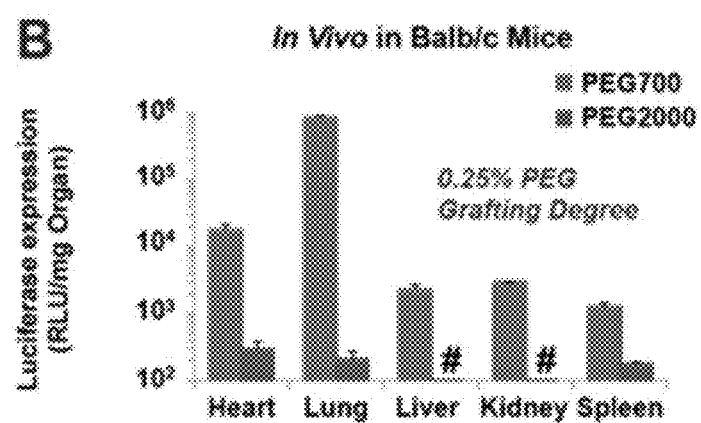
Figure 19A:
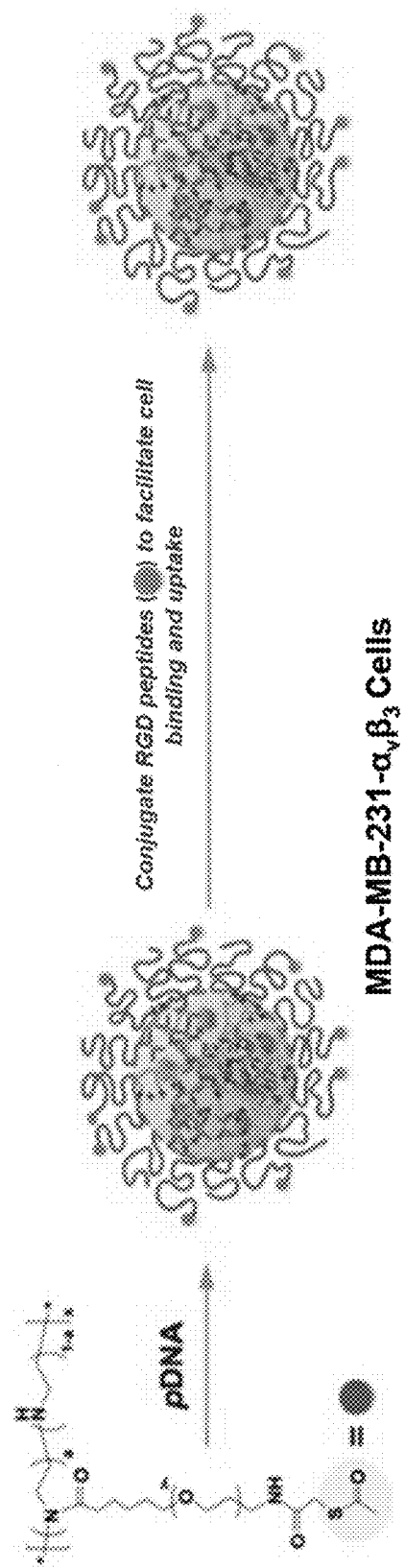
Figure 20A:
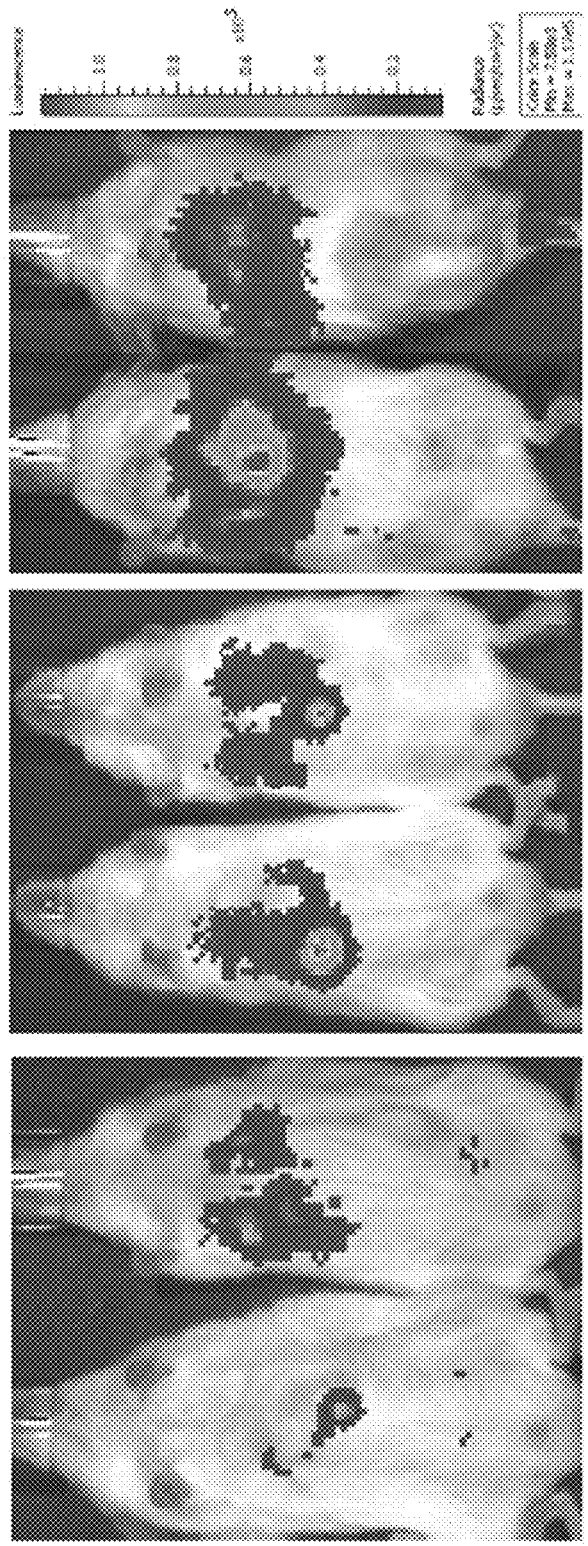
Figure 20B:
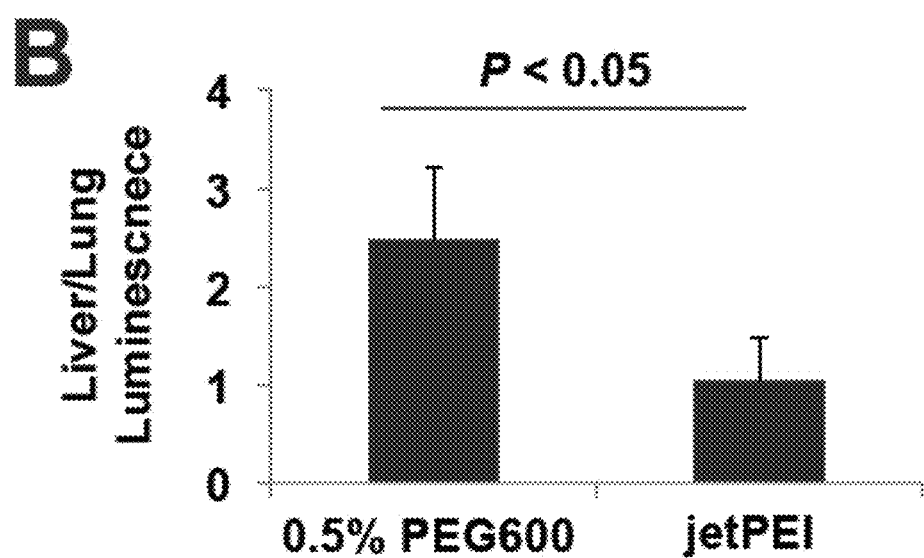
Figure 20C:
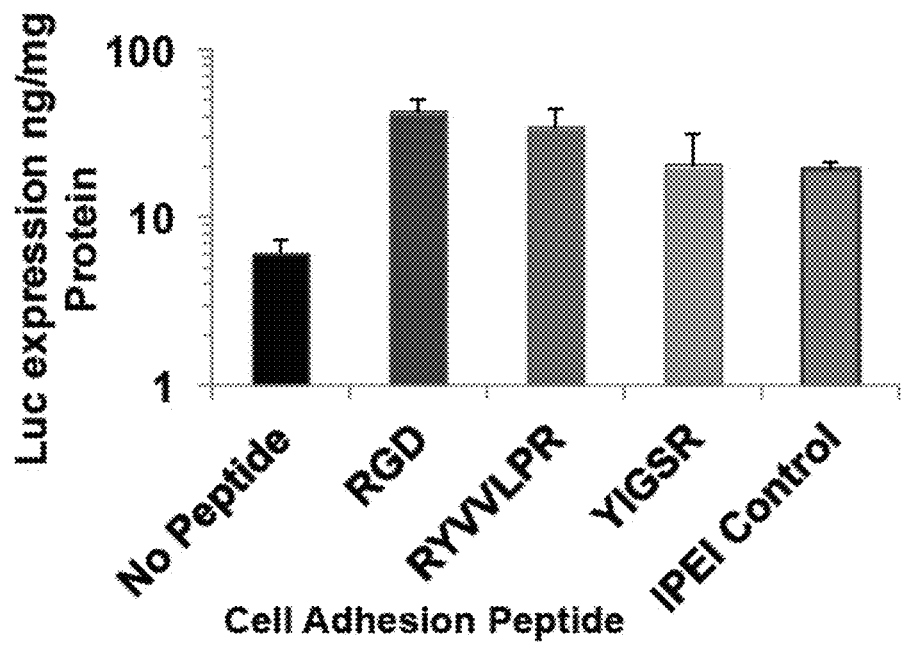
Figure 20D:
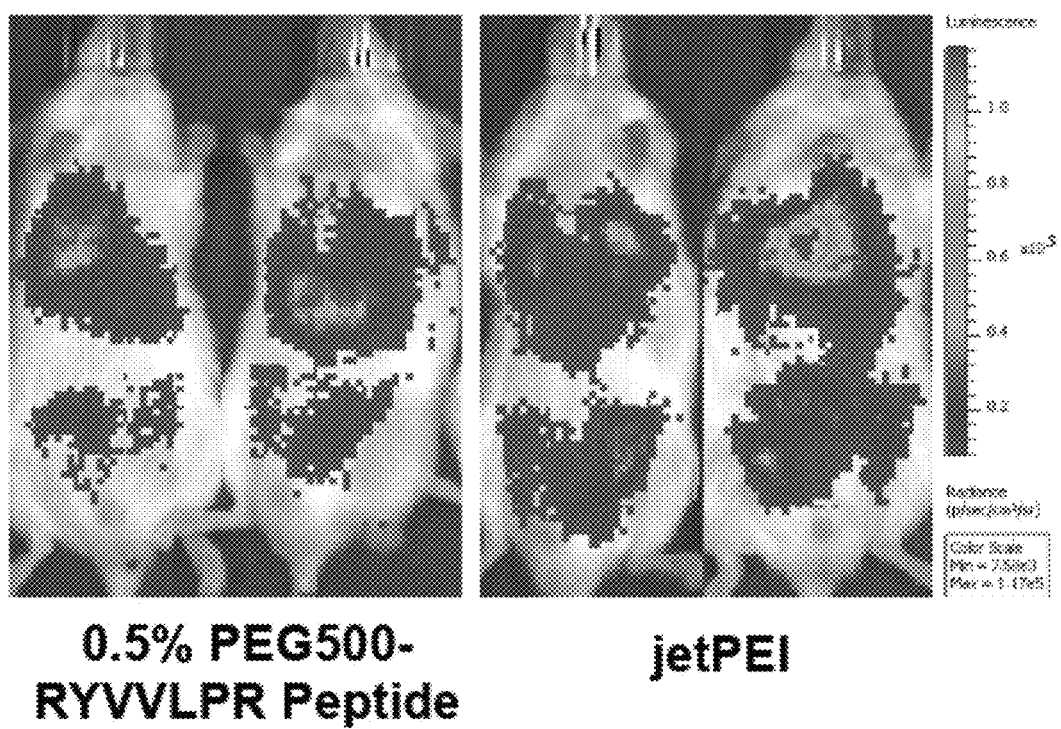
Figure 21:
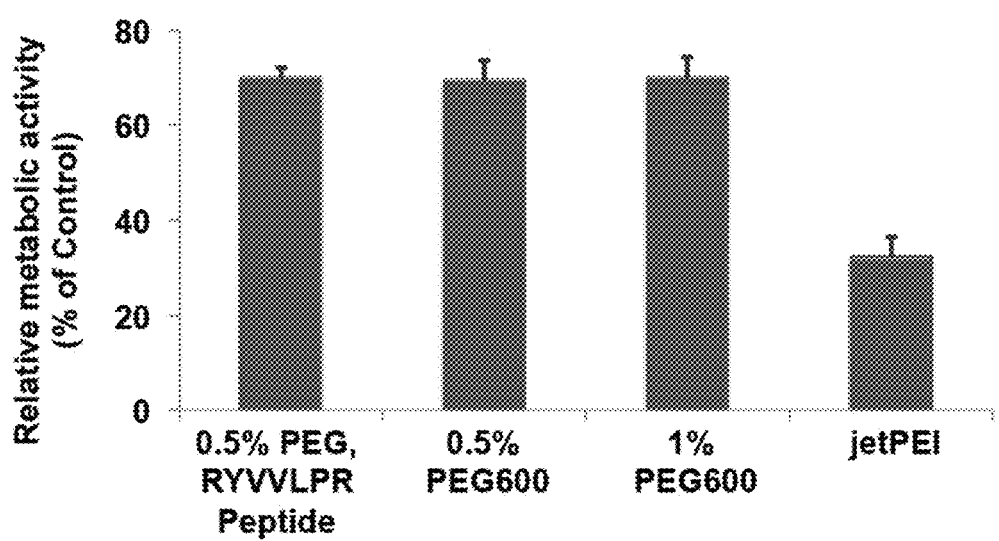
Figure 22A:
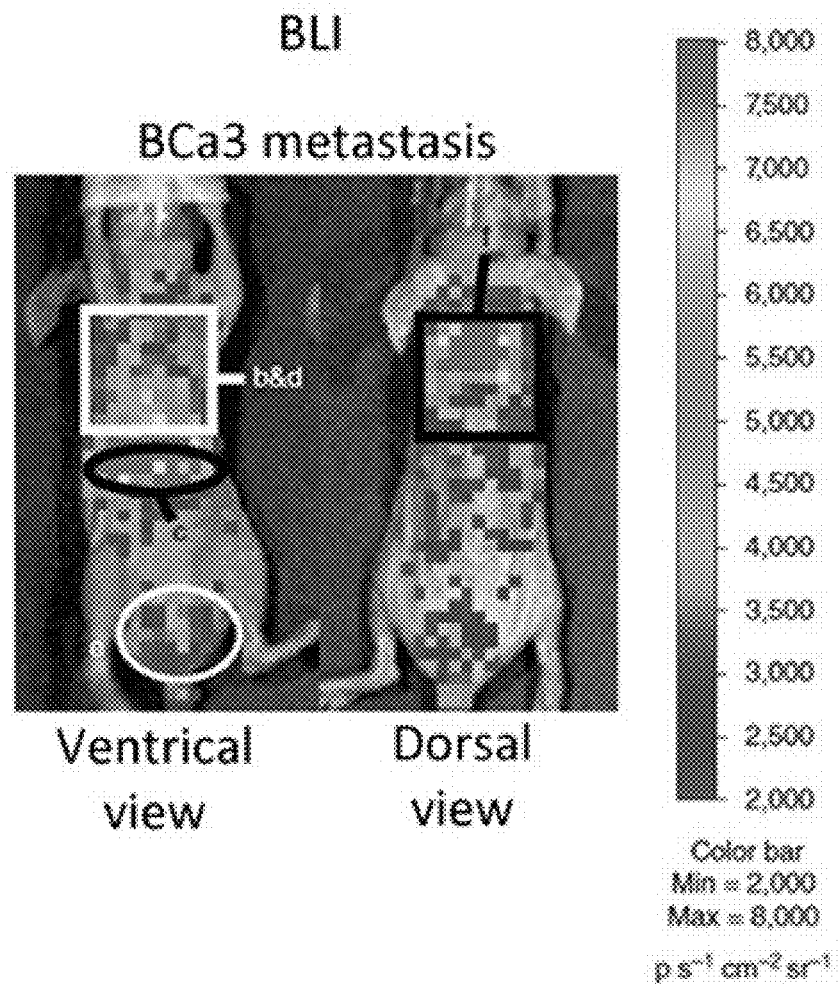
Figure 22B:
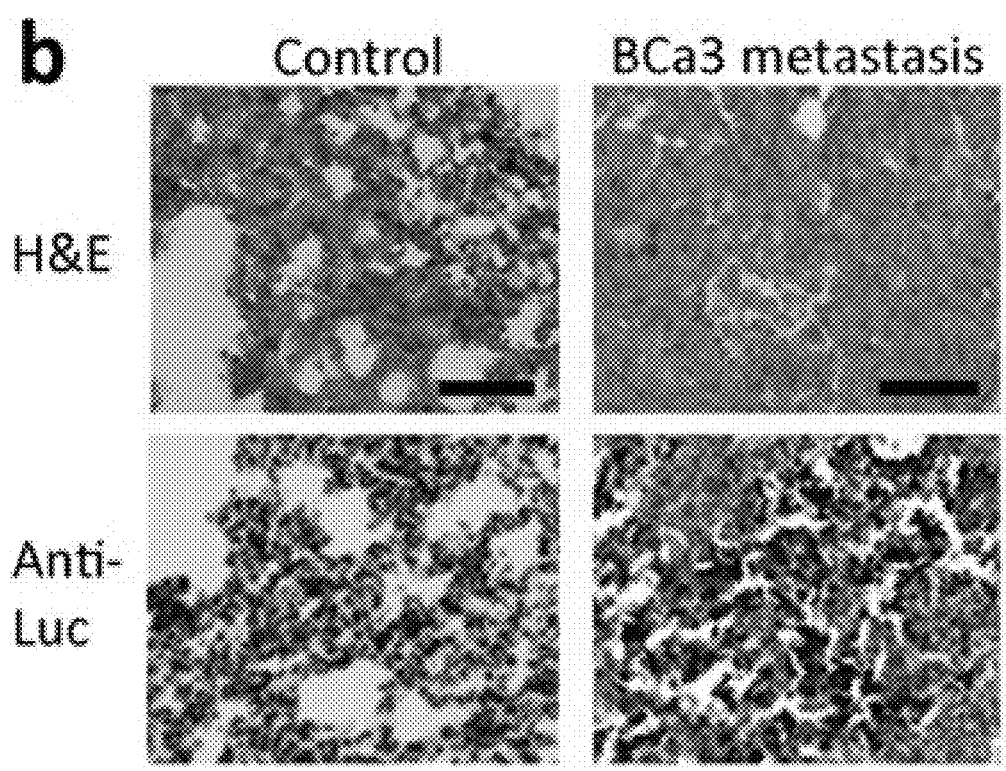
Figure 22C:
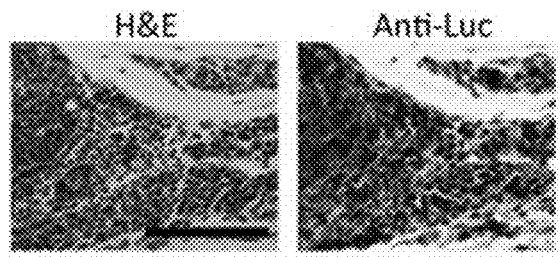
Figure 22D:
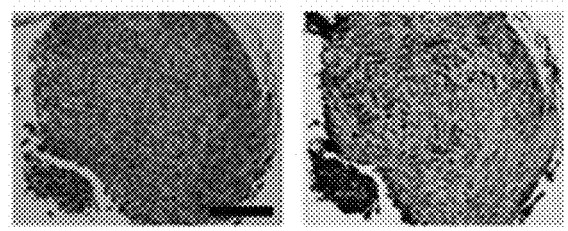
Figure 22E:
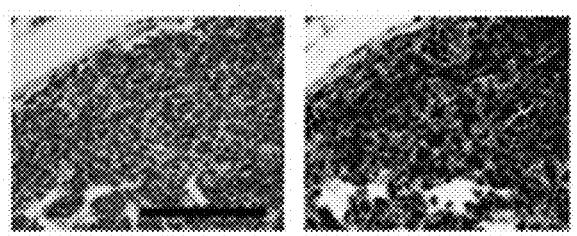
Figure 22F:
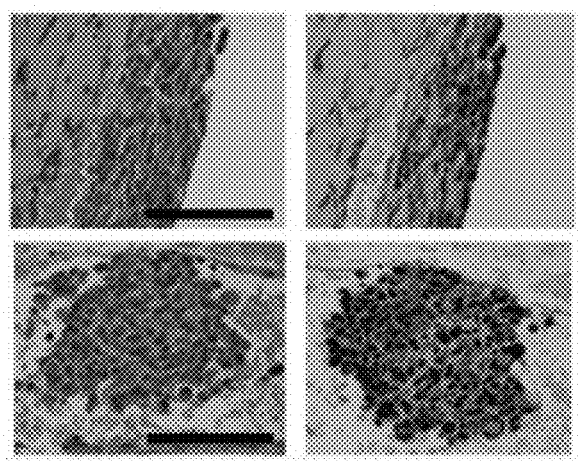
Figure 22K:
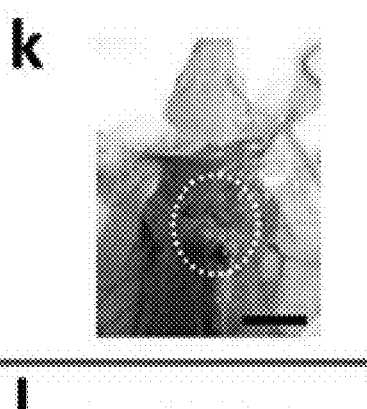
Figure 22L:
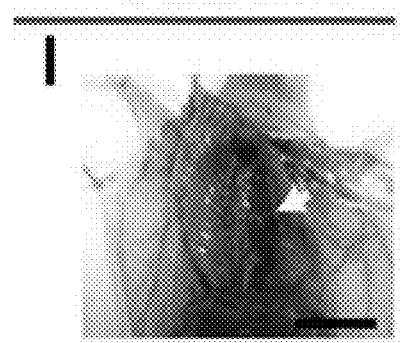
Figure 22M:
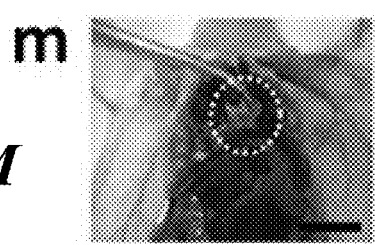
Figure 22N:
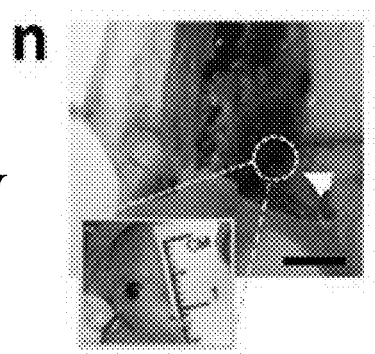
Figure 24:
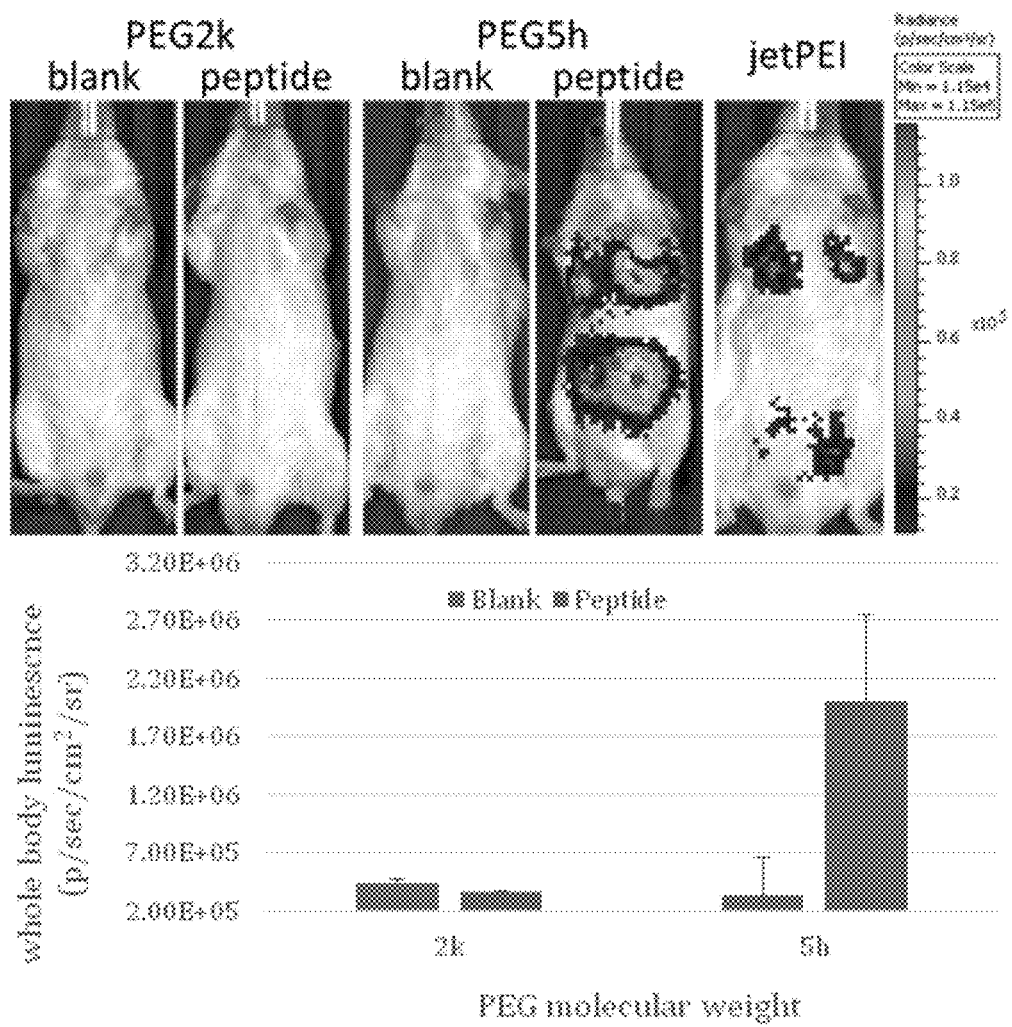
Figure 25A:
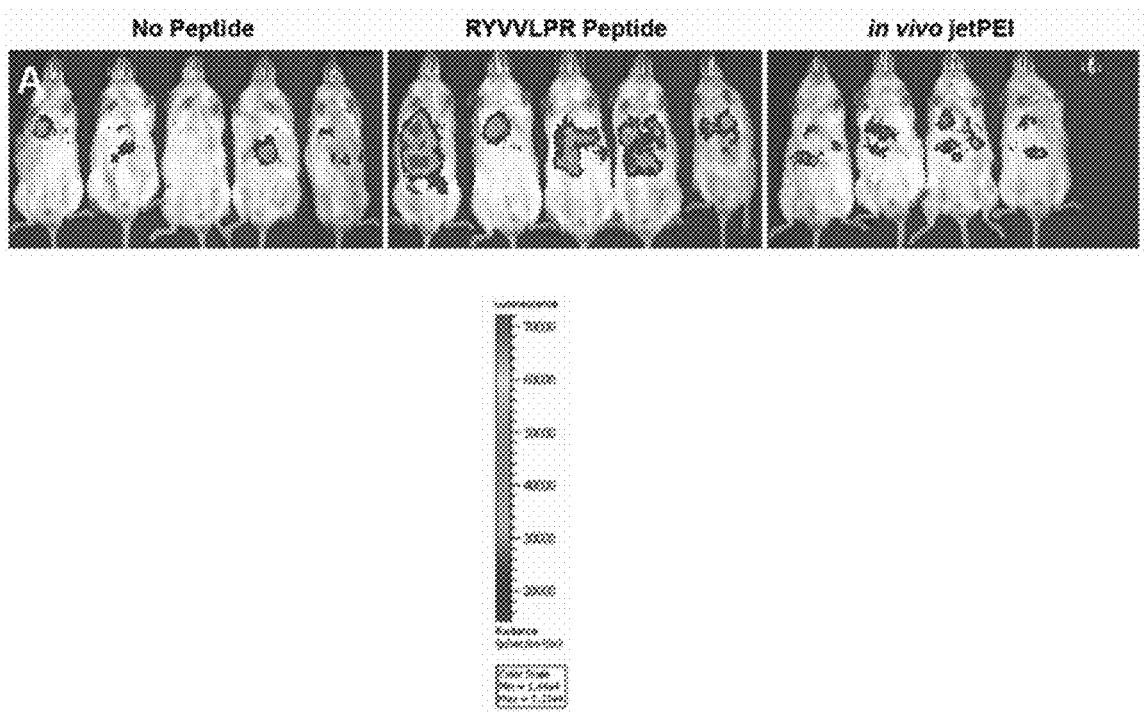
Figure 25B:
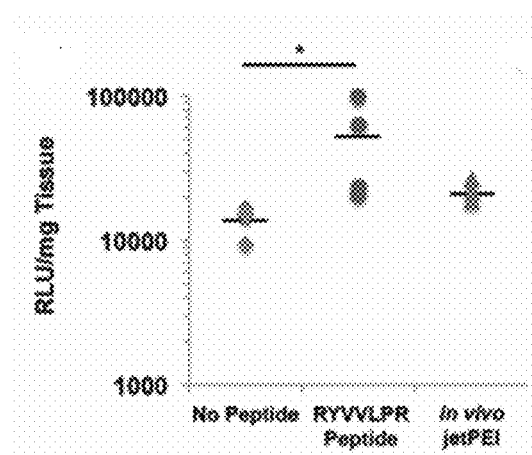
Figure 25C:
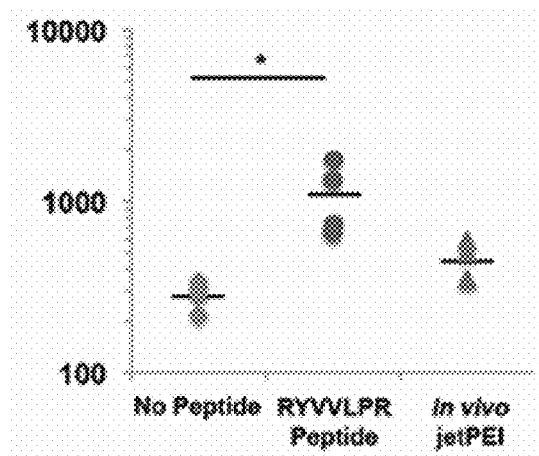
Figure 25D:
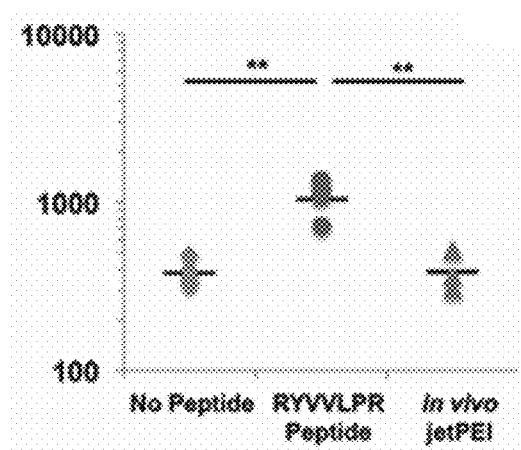
Figure 26A:
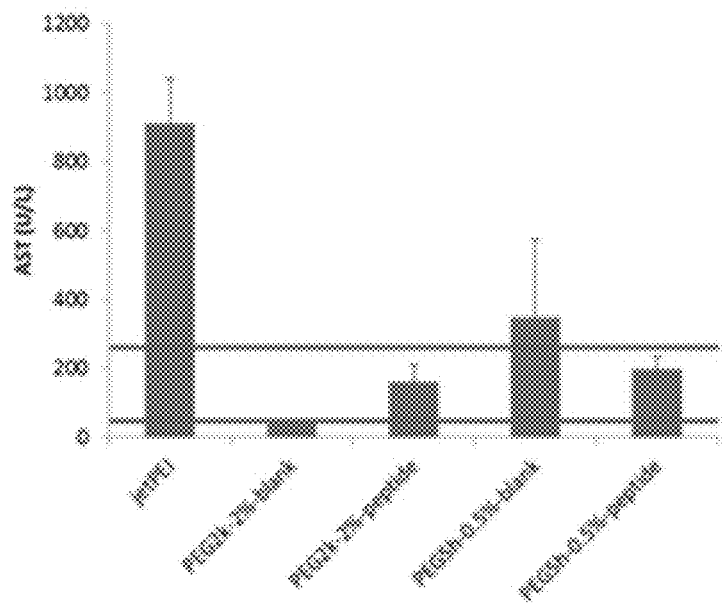
Figure 26B:
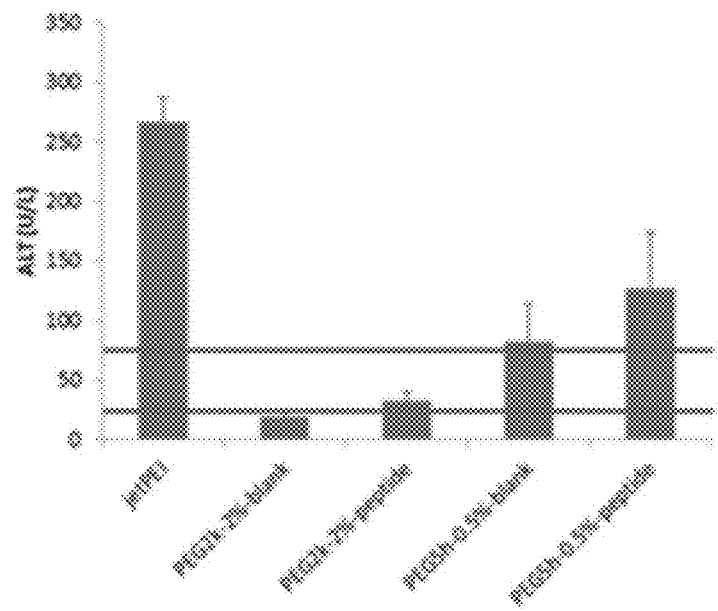

16F), and 8% PEG grafting degree (FIG. 16D and FIG. 16G) for PEG2000 and PEG700, respectively. All scale bars=200 nm;

FIG. 17A and FIG. 17B show the surface charge of lPEI-g-PEG$_{700}$/DNA micelles prepared with different PEG grafting degrees (FIG. 17A) and colloidal stability of lPEI-g-PEG$_{700}$/DNA nanoparticles as measured by dynamic light scattering after 15 min incubation in 150 mM salt and 5% (vol/vol) serum conditions (FIG. 17B);

FIG. 18A and FIG. 18B show transgene expression in PC3 prostate cancer cells following transfection with lPEI-g-PEG/DNA micelles prepared with PEG700 and PEG2000 at different grafting degrees (FIG. 18A) and in vivo transfection in different organs of Balb/c mice following i.v. injection of spherical lPEI-g-PEG/DNA micelles equivalent to 40 µg of plasmid DNA (FIG. 18B). PEG grafting degree was fixed at 0.25%. # indicates no detectable gene expression levels;

FIG. 19A and FIG. 19B show a schematic of ligand conjugation to copolymer/DNA micelles (FIG. 19A) and in vitro transfection efficiency of lPEI-g-PEG/DNA micelles in MDA-MB-231-αvβ3 cells at 48 hours after transfection (FIG. 19B). Micelles were prepared using lPEI-g-PEG with PEG$_{500}$ and PEG$_{2000}$ at different grafting degrees to yield different shapes, and with or without RGD ligands conjugated to PEG terminal;

FIGS. 20A, 20B, 20C, and 20D show in vivo bioluminescence images of PC3 metastatic prostate cancer (PCa)-bearing mice following i.v. injection of jetPEI/DNA and lPEI-g-PEG$_{600}$/DNA micelles containing firefly luciferase-expressing plasmid under the control of tumor-specific promoter (Bhang, *Nat. Med.* 2011; 17:123-129) (FIG. 20A); quantitative comparison of bioluminescence signal in liver and lung for lPEI-g-PEG$_{600}$/DNA micelles and jetPEI/DNA nanoparticles (FIG. 20B); in vitro transfection of PC3 cells following treatment with lPEI-g-PEG$_{500}$/DNA micelles conjugated with cell adhesion peptides (FIG. 20C); and bioluminescence imaging of PCa-bearing mice following i.v. injection of jetPEI/DNA nanoparticles and peptide-conjugated lPEI-g-PEG500/DNA micelles under the control of tumor-specific promoter (FIG. 20D);

FIG. 21 shows the relative metabolic activity in PC3 cells comparing peptide-conjugated lPEI-g-PEG500/DNA micelles, lPEI-g-PEG600/DNA micelles, and jetPEI/DNA nanoparticles;

FIG. 22A, FIG. 22B, FIG. 22C, FIG. 22D, FIG. 22E, FIG. 22F, FIG. 22G, FIG. 22H, FIG. 22I, FIG. 22J, FIG. 22K, FIG. 22L, FIG. 22M, and FIG. 22N show bioluminescence imaging (BLI) of a representative mouse, BCa3 from the group, 24 h after the systemic delivery of fLuc vector ((FIG. 22A; Bhang, *Nat. Med.* 2011; 17: 123). The organs associated with the expression of luciferase from (FIG. 22A) (black or white circles and rectangles) were collected for histological correlation (FIG. 22B, FIG. 22C, FIG. 22D, FIG. 22E and FIG. 22F). FIG. 22B shows H&E and luciferase staining on cryosections of the lung from BCa3, correlating with BLI light output shown in the white rectangle in FIG. 22A; stained lung cryosections of a control mouse (control) are shown for comparison. FIG. 22C, FIG. 22D, FIG. 22E and FIG. 22F show luciferase and H&E staining of the formalin-fixed, paraffin-embedded tissue sections collected from BCa3 confirms metastatic lesions observed with BLI. Scale bars, 100 µm. FIG. 22G, FIG. 22H, FIG. 22I, FIG. 22J, FIG. 22K, FIG. 22L, FIG. 22M and FIG. 22N show detection and localization of metastatic masses by whole body SPECT-CT imaging after the systemic administration of HSV1-tk vector. Images obtained from two representative mice, Mel-2 (FIG. 22G and FIG. 22H) and Mel-3 (FIG. 22I, FIG. 22J, FIG. 22K, FIG. 22L, FIG. 22M and FIG. 22N) at 24 h after [$^{125}$I]FIAU injection are shown here. Scale bars, 10 mm;

FIG. 23A and FIG. 23B show whole-body BLI monitoring firefly luciferase expression in a PC3/ML prostate cancer model. Two animals from each group are shown here as representation, that were imaged from the ventral view. Peak expression was observed at 48 h after administering a spherical I-PEI-g-PEG/DNA micelles (FIG. 23A) and the jet-PEI control (FIG. 23B);

FIG. 24 shows in vivo transfection efficiency in Balb/c mice at 2 days following i.v. injection of lPEI$_{22k}$-g-PEG$_{500}$/DNA nanoparticles and of lPEI$_{22k}$-g-PEG$_{2000}$/DNA nanoparticles prepared from copolymers with 2% PEG grafting degree with and without cell adhesion peptide (n=3);

FIG. 25A, FIG. 25B, FIG. 25C, and FIG. 25D show that ligand-conjugated DNA nanoparticles with short PEG5H grafts effectively detect metastatic prostate cancer lesions in vivo. FIG. 25A show in vivo bioluminescence imaging of PC3-ML tumor-bearing mice at 48 h following systemic injection of lPEI-g-PEG/DNA nanoparticles with or without RYVVLPR ligands compared to the positive control, in vivo jetPEI/DNA nanoparticles (n=4-5 per group). All bioluminescence images were adjusted to the same scale for comparison. FIG. 25B, FIG. 25C and FIG. 25D show a comparison of luciferase expression in the lung (FIG. 25B), liver (FIG. 25C), and kidney (FIG. 25D) tissue homogenate of the same PC3-ML tumor-bearing mice at 48 h following systemic injection of nanoparticle formulations (n=3-4 per group). Horizontal bar denotes the mean level of transgene expression. Plasmid DNA encoding firefly luciferase driven by the tumor-specific peg-promoter was used for all experiments. * p<0.05, ** p<0.01; and FIG. 26A and FIG. 26B show the level of liver enzymes (FIG. 26A) aspartate transaminase (AST) and (FIG. 26B) alanine transaminase (ALT) following infusion of nanoparticles as a measure of hepatocellular toxicity in Balb/c mice. Enzyme levels were measured at 2 days following i.v. injection of lPEI$_{22k}$-g-PEG$_{500}$/DNA nanoparticles or lPEI$_{22k}$-g-PEG2000/DNA nanoparticles prepared with 0.5% and 2% PEG grafting degree with and without cell adhesion peptide. Green lines indicate the normal range of enzymes.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides compositions of nucleic acid-containing polymeric nanoparticles for delivery of therapeutic nucleic acids and the methods of preparing and using the same. The presently disclosed polymer nanoparticle gene delivery system comprising poly(ethylene glycol) PEG can effectively control the shape of nucleic acid-containing nanoparticles while maintaining the beneficial properties of improved stability in biological media and still exhibiting high gene delivery efficiency.

It has been identified for the first time that, in some embodiments, organic, complex core nanoparticles with PEG corona are only effective in transfecting cells in vivo when the molecular weight (MW) of PEG is less than or about 1,000 Da. The consensus in the current state of the art is that the minimal MW of PEG is 2,000 Da to achieve significant stability. Further, in some embodiments, it has been found that the terminal group of the PEG significantly influences transfection efficiency only when PEG is smaller than 1,000 Da. The ligand-enhanced transfection is also only effective when PEG linkage is less than or equal to about 1,000 Da. In addition, it has been found for the first time that shape control of nucleic acid-containing nanoparticles is possible using PEG of less than or about 1,000 Da. The presently disclosed nanoparticles exhibit high level of transfections without noticeable toxicity.

In some embodiments, the presently disclosed methods involve the self-assembly of a nucleic acid, such as DNA, with one or more copolymers of polycations and poly(ethylene glycol) with an average molecular weight of less than 1,000 Da, forming complex core micellar nanoparticles with controlled shapes. The DNA-containing nanoparticles have improved stability in biological media compared to non-PEGylated versions and exhibit high in vitro and in vivo delivery efficiency. Furthermore, conjugation of targeting ligands and binding peptides to the terminal end of PEG allows for an enhancement of nucleic acid delivery.

I. Compositions of Nucleic Acid-Containing Nanoparticles for In Vivo Delivery

In some embodiments, the presently disclosed subject matter provides a polymeric micellar nanoparticle composition, comprising: (a) a block or graft copolymer comprising at least one polycationic polymer and at least one polyethylene glycol (PEG) polymer having an average molecular weight less than 1 kDa; and (b) at least one nucleic acid; wherein the graft or block copolymer and the at least one nucleic acid are complexed and condensed into a shaped micellar nanoparticle that is stable in biological media.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 300, 400, 500, 600, 700, 800, 900 and 1000 nm and all integers and fractional integers in between). In some embodiments, the size of the nanoparticle ranges from about 10 to about 500 nm in at least one dimension. In some embodiments, the nanoparticle has at least one dimension, e.g., a diameter, of about 100 nm. In some embodiments, the nanoparticle has a diameter of about 200 nm. In some embodiments, the nanoparticle has a diameter of about 300 nm. In some embodiments, the nanoparticle has a diameter of about 400 nm. In other embodiments, the nanoparticle has a diameter of about 500 nm. In yet other embodiments, the nanoparticle has a diameter of about 1000 nm (1 µm). In such embodiments, the particle also can be referred to as a "microparticle. Thus, the term "microparticle" includes particles having at least one dimension in the range of about one micrometer (µm), i.e., $1\times10^{-6}$ meters, to about 1000 µm. The term "particle" as used herein is meant to include nanoparticles and microparticles.

It will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes.

As used herein, a "polymer" is a molecule of high relative molecule mass, the structure of which essentially comprises the multiple repetition of unit derived from molecules of low relative molecular mass, i.e., a monomer. As used herein, a "block copolymer" is a copolymer that comprises two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively. As used herein, a "graft copolymer" is a branched copolymer in which the side chains are structurally, either constitutionally or configurationally, distinct from the main chain. As used herein, a polymer is a molecule that is made of small molecules that are arranged in a repeating structure to form a larger molecule. As used herein, a "polycationic polymer" is a polymer that has at least one positive charge. In some embodiments, in order to form an effective complex with DNA, the polymer is positively charged and comprises amino groups in the polymer backbone or grafted onto polymer side chains.

As used interchangeably herein, the terms "nucleic acids," "oligonucleotides," and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one of the following modifications: (a) an alternative linking group, (b) an analogous form of purine, (c) an analogous form of pyrimidine, or (d) an analogous sugar. For examples of analogous linking groups, purine, pyrimidines, and sugars, see for example PCT Patent App. Pub. No. WO 95/04064. The polynucleotide sequences of the presently disclosed subject matter may be prepared by any known method, including synthetic, recombinant, ex vivo generation, or a combination thereof, as well as utilizing any purification methods known in the art.

PEG can be included in the polymer backbone of the block copolymers or on the side chain in graft copolymers. In some embodiments, attaching PEG to the polymer is useful because PEG assists in the self-assembly process and influences the shape of polymer nanoparticles prepared with nucleic acids. In some embodiments, the graft or block polymer and nucleic acid form a micellar nanoparticle structure after mixing. With the PEGylated polymer, the micelle is configured such that the PEG chains, which are strongly hydrophilic, are arranged on the outer surface of the micelle to form a corona or shield around the surface of the nanoparticle, while the polycation segment complexes with the negatively charged nucleic acid through electrostatic interactions to form the micelle core. The corona around the surface of the nanoparticle may reduce protein adsorption to the nanoparticle surface, which in turn can reduce or prevent nanoparticle aggregation. If the nanoparticles aggregate, they may be too large for target cells to internalize and are more likely to be cleared from the body by macrophages and other mechanisms. Therefore, without wishing to be bound to any one particular theory, it is believed that the inclusion of PEG, particularly PEG with a molecular weight of less than or about 1,000 Da, into the presently disclosed nanoparticles, improves the nanoparticle stability in biological media.

As used herein, a "shaped micellar nanoparticle" is a micellar particle that has had its shape controlled by varying the grafting degree of PEG on the copolymer surface. For polymer/DNA nanoparticles, at low grafting degrees, nanoparticles primarily form spherical particles. At intermediate grafting degrees, nanoparticles are primarily rod-shaped. At high grafting degrees, worm-like shapes predominate. As used herein the term "spherical particle" refers to a particle having an aspect ratio of about 1, the term "rod-shaped particle" refers to a particle having an aspect ratio of between about 2 and about 5, and the term "worm-shaped particle" refers to a particle having an aspect ratio greater than about 10. In some embodiments, the size of the nanoparticles can range from about 10 nm to about 1000 nm in at least one dimension.

In some embodiments, the nanoparticle shape can also be controlled by varying the polarity of the solvent during nanoparticle formation. In these cases, water is combined with a water-miscible solvent of lower polarity to dissolve the polymer and nucleic acid. Examples of low polarity solvents include, but are not limited to, dimethyl sulfoxide, dimethylformamide, and p-dioxane. In addition, in some embodiments, adding salts, lowering the pH of the solutions, and changing the temperature can be used to change the shape of the nanoparticle. In some embodiments, the shaped micellar nanoparticle is a spherically-shaped micellar nanoparticle. In some embodiments, the shaped micellar nanoparticle is a rod-shaped micellar nanoparticle. In some embodiments, the shaped micellar nanoparticle is a worm-shaped micellar nanoparticle.

As used herein, the term "complexed" means the joining of two or more molecules covalently or noncovalently (e.g., via electrostatic interactions). As used herein, the term "condensed" refers to making a structure denser. For example, the presently disclosed copolymer can be complexed and condensed with at least one nucleic acid to form a presently disclosed shaped micellar nanoparticle that is stable or unlikely to come apart in biological media. As used herein, the terms "biological media" or "physiological media" refer to solutions that are compatible with solutions found in the body of a subject. In some embodiments, the conditions in the biological media may be similar to physiological conditions found in a part of the body of a subject. In some embodiments, the conditions in the biological media may be different from the physiological conditions found in a part of the body of a subject but the conditions in the biological media may still allow the presently disclosed nanoparticles to be stable. Thus, in some embodiments, the presently disclosed polymeric micellar nanoparticle compositions are in aqueous media and/or under physiological conditions when administered to a subject. In some embodiments, the biological or physiogical media comprises a serum-containing media. In some embodiments, the biological or physiological media comprises a salt-containing media.

In some embodiments, at least one PEG polymer of the presently disclosed composition has a molecular weight that is about or less than 1 kDa. In some embodiments, at least one PEG polymer has a molecular weight ranging from about 400 Da to about 1 kDa. In some embodiments, at least one PEG polymer has a molecular weight ranging from about 500 Da to about 700 Da. In some embodiments, at least one PEG polymer has a molecular weight of about 425 Da. In some embodiments, at least one PEG polymer has a molecular weight of about 450 Da. In some embodiments, at least one PEG polymer has a molecular weight of about 475 Da. In some embodiments, at least one PEG polymer has a molecular weight of about 500 Da. In some embodiments, at least one PEG polymer has a molecular weight of about 525 Da. In some embodiments, at least one PEG polymer has a molecular weight of about 550 Da. In some embodiments, at least one PEG polymer has a molecular weight of about 575 Da. In some embodiments, at least one PEG polymer has a molecular weight of about 600 Da. In some embodiments, at least one PEG polymer has a molecular weight of about 625 Da. In some embodiments, at least one PEG polymer has a molecular weight of about 650 Da. In some embodiments, at least one PEG polymer has a molecular weight of about 675 Da. In some embodiments, at least one PEG polymer has a molecular weight of about 700 Da. In some embodiments, at least one PEG polymer has a molecular weight of about 725 Da. In some embodiments, at least one PEG polymer has a molecular weight of about 750 Da. In some embodiments, at least one PEG polymer has a molecular weight of about 775 Da. In some embodiments, at least one PEG polymer has a molecular weight of about 800 Da. In some embodiments, at least one PEG polymer has a molecular weight of about 825 Da. In some embodiments, at least one PEG polymer has a molecular weight of about 850 Da. In some embodiments, at least one PEG polymer has a molecular weight of about 875 Da. In some embodiments, at least one PEG polymer has a molecular weight of about 900 Da. In some embodiments, at least one PEG polymer has a molecular weight of about 925 Da. In some embodiments, at least one PEG polymer has a molecular weight of about 950 Da. In some In some embodiments, at least one PEG polymer has a molecular weight of about 450 Da. embodiments, at least one PEG polymer has a molecular weight of about 100 Da.

In some embodiments, at least one PEG polymer has a graft density or graft degree ranging from about 0.25 mol % to about 10 mol %, wherein mol % refers to the fraction of functional side groups grafted with PEG. In some embodiments, at least one PEG polymer has a graft density or graft degree of 0.25 mol %. In some embodiments, at least one PEG polymer has a graft density or graft degree of 0.50 mol %. In some embodiments, at least one PEG polymer has a graft density or graft degree of 0.75 mol %. In some embodiments, at least one PEG polymer has a graft density or graft degree of 1 mol %. In some embodiments, at least one PEG polymer has a graft density or graft degree of 2 mol %. In some embodiments, at least one PEG polymer has a graft density or graft degree of 3 mol %. In some embodiments, at least one PEG polymer has a graft density or graft degree of 4 mol %. In some embodiments, at least one PEG polymer has a graft density or graft degree of 5 mol %. In some embodiments, at least one PEG polymer has a graft density or graft degree of 6 mol %. In some embodiments, at least one PEG polymer has a graft density or graft degree of 7 mol %. In some embodiments, at least one PEG polymer has a graft density or graft degree of 8 mol %. In some embodiments, at least one PEG polymer has a graft density or graft degree of 9 mol %. In some embodiments, at least one PEG polymer has a graft density or graft degree of 10 mol %.

In some embodiments, at least one PEG polymer of the presently disclosed composition is terminated with a functional group, such as a terminal acrylate group, a terminal alkoxy group, a terminal amino group, terminal carboxyl group, a terminal hydroxyl group, a terminal maleimide group, a terminal methacrylate group, a terminal methoxy group, a terminal 2-pyridyldithio (SPDP) group, a terminal thiol group, a negatively charged terminal group, or amphoteric group, or combinations thereof. In some embodiments, a ligand is conjugated to at least one PEG polymer and/or the functional group. In some embodiments, an amino group can also be used to crosslink the polymer. As used herein, the term "conjugated" means to form a stable covalent link between two molecules.

In some embodiments, the ligand conjugated to at least one PEG polymer and/or functional group is a diagnostic agent (an agent that can be used to diagnose a disease or condition) an imaging agent (an agent that can be used to reveal and/or define the localization of a disease or condition), a targeting agent (an agent that can target a specific kind of cell or tissue, such as a cancer cell), a theranostic agent (an agent that can diagnose and also treat a disease or condition), a therapeutic agent (an agent that can treat a disease or condition), and the like, as well as combinations thereof. In some embodiments, the ligand is a DNA, RNA, polypeptide, antibody, antibody fragment, antigen, carbohydrate, protein, peptide, enzyme, amino acid, hormone, steroid, vitamin, drug, virus, polysaccharide, lipid, lipopolysaccharide, glycoprotein, lipoprotein, nucleoprotein, oligonucleotide, immunoglobulin, albumin, hemoglobin, coagulation factor, peptide hormone, protein hormone, non-peptide hormone, interleukin, interferon, cytokine, peptides comprising a tumor-specific epitope, cell, cell-surface molecule, cell adhesion peptide, cell-binding peptide, cell receptor ligand, small organic molecule, small organometallic molecule, nucleic acid, oligonucleotide, transferrin, metabolites thereof, and antibodies or agents that bind to any of the above substances. In some embodiments, ligands, such as targeting ligands or cell binding peptides, are conjugated to the terminal end of the PEG to enhance cell binding. In some embodiments, attaching a cell-targeting ligand can enhance uptake to a particular cell.

As used herein, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

In some embodiments, the ligand is detectable using an imaging modality selected from the group consisting of bioluminescence imaging, fluorescence imaging, magnetic resonance imaging (MRI), positron emission tomography (PET), x-ray computed tomography (CT), single-photon emission computed tomography (SPECT), or combinations thereof.

In some embodiments, the ligand conjugated to at least one PEG polymer and/or functional group comprises a peptide comprising the amino acid sequence Ac-CCR-RYVVLPRWLC (SEQ ID NO: 1). In some embodiments, the ligand conjugated to at least one PEG polymer and/or functional group comprises a peptide comprising the amino acid sequence YIGSR (SEQ ID NO: 3). In some embodiments, the ligand comprises a cyclic RGD-thiol peptide (cRGD). In some embodiments, the peptide is present in a 1:1 molar ratio of thiol in the peptide to SPDP terminal groups on the nanoparticle surface. In some embodiments, the peptide is present in a 10:1 ratio, a 9:1 ratio, a 8:1 ratio, a 7:1 ratio, a 6:1 ratio, a 5:1 ratio, a 4:1 ratio, a 3:1 ratio, a 2:1 ratio, a 1:2 ratio, a 1:3 ratio, a 1:4 ratio, a 1:5 ratio, a 1:6 ratio, a 1:7 ratio, a 1:8 ratio, a 1:9 ratio, or a 1:10 molar ratio of thiol in the peptide to the terminal group (e.g., SPDP terminal group) on the nanoparticle surface. In some embodiments, the ligand comprises a moiety that binds to a tumor-specific antigen, an antigenic substance produced in tumor cells that can be used as a tumor marker. In some embodiments, the ligand comprises a prostate-specific membrane antigen (PSMA)-binding moiety.

In some embodiments, at least one polycationic polymer of the presently disclosed composition is linear polyethylenimine (LPEI), poly-lysine, poly-arginine, poly-histidine, chitosan, branched PEI, a poly (beta-aminoester), a polyphosphoester (PPE), polyphosphoramidate (PPA), and the like. In some embodiments, the molecular weight of the polycation ranges from about 1 kDa to about 50 kDa. In some embodiments, at least one polycationic polymer is LPEI. In some embodiments, the LPEI has a molecular weight ranging from about 2 kDa to about 50 kDa. In some embodiments, the LPEI has a molecular weight of about 22 kDa. In some embodiments, at least one polycationic polymer is not branched PEI. In some embodiments, the graft copolymer is not a branched PEI(25 kDa)-g-linear PEG(550 Da)$_n$ copolymer, wherein n is the average number of PEG blocks per one PEI macromolecule and n is equal to 35. As used herein, a "branched copolymer" consists of a single main chain with one or more polymeric side chains.

In some embodiments, the presently disclosed composition comprises at least one nucleic acid having a length ranging from about 10 bases to about 10 kilobases (kb). In some embodiments, the at least one nucleic acid has a length of 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31 bases 32 bases, 33 bases, 34 bases, 35 bases, 36 bases, 37 bases 38 bases, 39 bases, 40 bases, 41 bases, 42 bases, 43 bases, 44 bases, 45 bases, 46 bases, 47 bases, 48 bases, 49 bases, 50 bases, 60 bases, 64 bases, 70 bases, 72 bases, 75 bases, 80 bases, 90 bases, 96 bases, 99 bases, 100 bases, 200 bases, 250 bases, 300 bases, 325 bases, 350 bases, 375 bases, 400 bases, 425 bases, 450 bases, 475 bases, 500 bases, 600 bases, 700 bases, 750 bases, 800 bases, 850 bases, 900 bases, 1 kb, 1.1 kb, 1.2 kb, 1.3 kb, 1.4 kb, 1.5 kb, 1.6 kb, 1.7 kb, 1.8 kb, 1.9 kb, 2 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4 kb, 4.1 kb, 4.2 kb, 4.3 kb, 4.4 kb, 4.5 kb, 4.6 kb, 4.7 kb, 4.8 kb, 4.9 kb, 5 kb, 5.1 kb, 5.2 kb, 5.3 kb, 5.4 kb, 5.5 kb, 5.6 kb, 5.7 kb, 5.8 kb, 5.9 kb, 6 kb, 6.1 kb, 6.2 kb, 6.3 kb, 6.4 kb, 6.5 kb, 6.6 kb, 6.7 kb, 6.8 kb, 6.9 kb, 7 kb, 7.1 kb, 7.2 kb, 7.3 kb, 7.4 kb, 7.5 kb, 7.6 kb, 7.7 kb, 7.8 kb, 7.9 kb, 8 kb, 8.1 kb, 8.2 kb, 8.3 kb, 8.4 kb, 8.5 kb, 8.6 kb, 8.7 kb, 8.8 kb, 8.9 kb, 9 kb, 9.1 kb, 9.2 kb, 9.3 kb, 9.4 kb, 9.5 kb, 9.6 kb, 9.7 kb, 9.8 kb, 9.9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, or 25 kb or greater. In some embodiments, the presently disclosed composition comprises at least one nucleic acid having a length of at least 15 kilobases, at least 20 kilobases, or at least 25 kilobases or more. In some embodiments, at least one nucleic acid includes, but is not limited to, an antisense oligonucleotide, cDNA, genomic DNA, guide RNA, plasmid DNA, vector DNA, mRNA, miRNA, piRNA, shRNA, and siRNA. In some embodiments, at least one nucleic acid is selected from the group consisting of an antisense oligonucleotide, cDNA, genomic DNA, guide RNA, plasmid DNA, vector DNA, mRNA, miRNA, piRNA, shRNA, and siRNA. In some embodiments, the nucleic acid is DNA and the DNA is supercoiled. In some embodiments, the nucleic acid is DNA and the DNA is linear. In some embodiments, the nucleic acid is DNA and the DNA is a minicircle DNA.

The amount of cationic polymer can be calculated with an N/P ratio, where N is the amino groups, or amino group equivalents, in the cationic polymer and P is the number of phosphate groups in the nucleic acid. In some embodiments, the N/P ratio ranges from about 0.1 to about 20. In some embodiments, the N/P ratio ranges from about 1 to about 20. In some embodiments, the N/P ratio is less than 10. In some embodiments, the N/P ratio is less than 9. In some embodiments, the N/P ratio is about 8.

As used herein, a "small interfering RNA" or "siRNA" is defined as an agent which functions to inhibit expression of a target gene, e.g., by RNA interference (RNAi). Other molecules capable of mediating sequence-specific RNAi include, but are not limited to, double-stranded RNA (dsRNA), microRNA (miRNA), short hairpin or small hairpin RNA (shRNA), short interfering oligonucleotide, and post-transcriptional gene silencing RNA (ptgsRNA). An siRNA may be chemically synthesized, may be produced by in vitro transcription, or may be produced within a host cell. In some embodiments, siRNA is a double stranded RNA (dsRNA) molecule of about 15 to about 40 nucleotides in length. siRNA interferes with the expression of specific genes with complementary nucleotide sequences in some cases by causing gene silencing or a reduction in gene expression. This may occur by promoting RNA interference through degradation or specific post-transcriptional gene silencing (PTGS) of the target messenger RNA (mRNA). Piwi-interacting RNAs (piRNAs) form RNA-protein complexes through interactions with piwi proteins. As used herein, "gene silencing" is a general term that refers to the ability to prevent the expression of a certain gene.

In some embodiments, the presently disclosed composition comprises at least one nucleic acid comprising an expression vector encoding at least one reporter gene operably linked to a promoter. In some embodiments, at least one nucleic acid comprises an expression vector encoding at least one antigen epitope operably linked to a promoter. As used herein, the term "antigen epitope" refers to the part of an antigen that is recognized by the immune system, such as by antibodies, B cells, or T cells. In some embodiments, the antigen epitope is a tumor-specific antigen epitope, such as a prostate-specific membrane antigen (PSMA) epitope. In some embodiments, the tumor-specific antigen has epitopes that are recognized by T cells and/or epitopes that are recognized by B cells.

A number of suitable expression vectors are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals. The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter).

A "gene," as used herein, refers to a polynucleotide containing at least one open reading frame that is capable of encoding a particular protein after being transcribed and translated. As used herein, a "gene product" is the biochemical material, either RNA or protein, resulting from expression of a gene. A measurement of the amount of gene product is sometimes used to infer how active a gene is. As used herein, "gene expression" is the process by which information from a gene is used in the synthesis of a functional gene product. As used herein, a "reporter gene" refers to a gene that produces a gene product that is easily detected. Examples of reporter genes include, but are not limited to, bioluminescent, fluorescent, computed tomography (CT), magnetic resonance imaging (MRI), positron emission tomography (PET), single-photon emission computed tomography (SPECT) reporter genes, and the like. In some embodiments, the reporter gene is a bioluminescent reporter gene (e.g., firefly luciferase. In some embodiments, the reporter gene is a fluorescent reporter gene (e.g., green fluorescent protein). In some embodiments, the reporter gene is a PET reporter gene.

In some embodiments, the presently disclosed composition comprises a promoter that is a constitutively active promoter and is usually active. In some embodiments, the promoter is an inducible promoter that is active in response to specific stimuli. In some embodiments, the promoter is a tissue-specific promoter that is active in specific tissues. In some embodiments, the promoter is a tumor-specific promoter that is active specifically in tumor cells.

In some embodiments, the expression vector of the presently disclosed composition further comprises a therapeutic gene. In some embodiments, the therapeutic gene itself can be used to treat a disease or condition, such as by correcting a gene mutation. In some embodiments, the therapeutic gene can be used to express a gene product and the gene product is used to treat a disease or condition. In some embodiments, the therapeutic gene is a cytotoxic gene that directly or indirectly kills a particular cell, such as a cancer cell. In some embodiments, the therapeutic gene is an immunomodulator gene that increases or decreases an immune response. In some embodiments, the therapeutic gene is a suicide gene that causes a cell to kill itself. In some embodiments, the therapeutic gene is a tumor suppressor gene that may reduce uncontrolled cell growth, for example. As used herein, as it relates to a subject, by "disease" or "condition" is meant any dysfunction or disorder that damages or interferes with the normal function of a cell, tissue, or organ.

In some embodiments, the presently disclosed composition further comprises a therapeutic agent. In some embodiments, the composition further comprises a chemotherapeutic agent. As used herein, a 'therapeutic agent" or a "therapeutic gene" is an agent or gene, respectively, that can be used to treat a disease or condition. A "chemotherapeutic agent" is used to connote a compound or composition that is administered in the treatment of cancer. Chemotherapeutic agents useful in methods, compositions, and kits disclosed herein include, but are not limited to, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel and docetaxel; chlorambucil; gemcitabine; 6-thioguanine; mercaptopurine; platinum analogs such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the expression vector of the presently disclosed composition further comprises an antigen gene. In some embodiments, the antigen gene encodes at least one antigen against infectious diseases, allergens, or cancer cells. As used herein, the term "infectious disease" refers to a disease or disorder caused by an organism, such as a bacterium, virus, fungus, or parasite. Examples of infectious diseases include, but are not limited to, respiratory infections, HIV/AIDS, gastrointestinal diseases, tuberculosis, malaria, measles, pertussis, tetanus, meningitis, syphilis, hepatitis A and B, and tropical diseases. As used herein, the term "allergen" refers to a substance that causes an allergic reaction, such as pollen (e.g., microspores of weeds, trees, grasses, etc.), vapor, gas, food, beverage (or a component thereof), drug, toxin, microbial antigen (e.g., viral, viral split antigen, bacterial, parasitic, fungal, and combinations thereof), dander, animal-derived compounds, dust (e.g., dust having LPS or dust mite feces), polypeptide, carbohydrate, nucleic acid, or any other agent capable of eliciting an allergic reaction.

Examples of antigen genes include, but are not limited to, genes encoding for hepatitis B virus surface antigens, *Shigella sonnei* form IO-Ps antigens, prostate-specific membrane antigen (PSMA), $\alpha_v\beta_3$ integrin, melanoma tumor antigens, HER-2/neu gene product, estrogen receptor, milk fat globulin, p53 tumor suppressor protein, mucin antigens; telomerases, nuclear matrix proteins, prostatic acid phosphatase, papilloma virus antigens, and antigens associated with cancers described herein.

In some embodiments, the expression vector of the presently disclosed composition further comprises at least one origin of replication. In some embodiments, the expression vector further comprises a nuclear antigen. In some embodiments, the expression vector further comprises transcriptional amplification machinery.

In some embodiments, the presently disclosed micellar nanoparticle composition targets at least one target cell. In some embodiments, at least one target cell comprises a cancer cell. In some embodiments, the cancer cell comprises a metastatic cancer cell. In some circumstances, cancer cells will be in the form of a tumor; such cells may exist locally within an animal, or circulate in the blood stream as independent cells, for example, leukemic cells. Cancer as used herein includes newly diagnosed or recurrent cancers, including without limitation, blastomas, carcinomas, gliomas, leukemias, lymphomas, melanomas, myeloma, and sarcomas. Cancer as used herein includes, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. In some embodiments, the cancer cell is a breast cancer cell. In some embodiments, the cancer cell is a cervical cancer cell. In some embodiments, the cancer cell is a melanoma cancer cell. In some embodiments, the cancer cell is a prostate cancer cell.

In some embodiments, the presently disclosed micellar nanoparticle composition contacts at least one target cell, the micellar nanoparticle composition is taken up by the at least one target cell and/or transfects the at least one target cell with the at least one nucleic acid. The term "contacting" as used herein refers to any action that results in at least one nanoparticle of the presently disclosed subject matter physically contacting at least one target cell. In some embodiments, the micellar nanoparticle composition exhibits a transfection efficiency of at least one target cell of between 10-fold and 100-fold greater than a micellar nanoparticle composition comprising a PEG polymer having an average molecular weight greater than 1 kDa. In some embodiments, the micellar nanoparticle composition exhibits a transfection efficiency of at least one target cell of at least 100-fold greater than a micellar nanoparticle composition comprising a PEG polymer having an average molecular weight greater than 1 kDa.

II. Methods for Preparing Nucleic Acid-Containing Nanoparticles for In Vivo Delivery In some embodiments, the presently disclosed subject matter provides a method for preparing a polymeric micellar nanoparticle composition of the presently disclosed subject matter, the method comprising: (a) mixing a first solution comprising the block or graft copolymer together with a second solution comprising the at least one nucleic acid to form a third solution comprising the block or graft copolymer and the at least one nucleic acid; and (b) allowing the block or graft copolymer and the at least one nucleic acid to self-assemble into the polymeric micellar nanoparticle.

In some embodiments, the nucleic acid and the cationic polymer can be prepared by dissolving the nucleic acid or the cationic polymer in a liquid, such as water, buffer, or other solution that allows for the stability of the nucleic acid or the cationic polymer. In some embodiments, in order to form nanoparticles, the solution of polymer is mixed with the solution of nucleic acid. In some embodiments, mixing is done by pipetting or vortexing the mixture. In some embodiments, the mixing is performed for less than a minute, such as for about 10 seconds. In some embodiments, after mixing, the solution is allowed to rest. In some embodiments, the solution is allowed to rest for more than about 1 minute, such as for about 5, 10, 15, 20 or longer minutes. In some embodiments, the solution is allowed to rest for about 10 minutes.

III. Methods for Targeting a Cell and Treating a Subject Using the Nucleic Acid-Containing Nanoparticles The presently disclosed micellar nanoparticles can be used to deliver nucleic acids in vitro and in vivo. For example, in some embodiments, cells in culture can be transfected with the nanoparticles. In some embodiments, the presently disclosed subject matter provides a transfection agent for transfecting a cell with at least one nucleic acid, comprising a polymeric micellar nanoparticle according to the presently disclosed subject matter or produced according to the presently disclosed methods.

In some embodiments, the presently disclosed subject matter provides a method of modulating expression of at least one gene in a cell, tissue, or subject, the method comprising administering an effective amount of the transfection agent of the presently disclosed subject matter to the cell, tissue, or subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In some embodiments, the presently disclosed subject matter provides a method for targeting at least one metastatic cancer cell in a subject, the method comprising administering a presently disclosed polymeric micellar nanoparticle composition or a polymeric micellar nanoparticle composition produced according to the presently disclosed methods, to a subject, wherein the polymeric micellar nanoparticle composition comprises a ligand that binds to a tumor-specific antigen on the surface of the at least one metastatic cancer cell, and wherein the ligand binds to the tumor-specific antigen on the surface of the at least one metastatic cancer cell after administration of the polymeric micellar nanoparticle composition to the subject, thereby targeting the at least one metastatic cancer cell in the subject. In some embodiments, targeting at least one metastatic cancer cell comprises treating a metastatic cancer in the subject.

As used herein, the term "treating" can include reversing, alleviating, inhibiting the progression of, preventing or reducing the likelihood of the disease, disorder, or condition to which such term applies, or one or more symptoms or manifestations of such disease, disorder or condition (e.g., cancer).

In some embodiments, the polymeric micellar nanoparticle composition further comprises a chemotherapeutic agent and/or at least one nucleic acid encoding a therapeutic gene that inhibits the growth, proliferation and/or survival of at least one metastatic cancer cell. As used herein, the term "inhibit" or "inhibits" means to decrease, suppress, attenuate, diminish, arrest, or stabilize the development or progression of a disease, disorder, or condition, e.g. cancer, by at least 10%, 20%, 30%, 40%, 50%, 60%, 70%, 80%, 90%, 95%, 98%, 99%, or even 100% compared to an untreated control subject, cell, biological pathway, or biological activity.

In some embodiments, targeting at least one metastatic cancer cell comprises detecting, diagnosing, and/or imaging a metastatic cancer in the subject. In some embodiments, the polymeric micellar nanoparticle composition further comprises an imaging agent and/or at least one nucleic acid encoding a reporter gene operably linked to a tumor-specific promoter. Many appropriate imaging agents are known in the art, such as paramagnetic ions (e.g., chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III)), radioactive isotopes ($^{211}$astatine, $^{14}$carbon, $^{51}$chromium, $^{36}$chlorine, $^{57}$cobalt, $^{58}$cobalt, $^{67}$copper, $^{152}$Eu, $^{67}$gallium, $^{3}$hydrogen, $^{123}$iodine, $^{125}$iodine, $^{131}$iodine, $^{111}$indium, $^{59}$iron, $^{32}$phosphorus, $^{186}$rhenium, $^{188}$rhenium, $^{75}$selenium, $^{35}$sulphur, $^{99m}$technicium, $^{90}$yttrium), fluorochromes (e.g., Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, Texas Red), PET and NMR-detectable substances (e.g., $^{64}$Cu-ATSM, FDG, $^{18}$F-fluoride, FLT, FMISO, gallium, technetium-$^{99}$m, thallium), MRI imaging agents (e.g., gadolinium), X-ray imaging agents (barium, iodide), enzymes (urease, alkaline phosphatase, (horseradish) hydrogen peroxidase and glucose oxidase), secondary binding ligands (e.g., biotin and/or avidin and streptavidin), and azido group molecules (e.g., 2- and 8-azido analogues of purine nucleotides).

In some embodiments, the reporter gene comprises a bioluminescent reporter gene, a fluorescent reporter gene, a CT (computed tomography) reporter gene, an MRI (magnetic resonance imaging) reporter gene, a PET (positron emission tomography) reporter gene, a SPECT (single-photon emission computed tomography) reporter gene, and combinations thereof. In some embodiments, the method further comprises imaging the subject after administering the polymeric micellar composition using an imaging modality selected from the group consisting of bioluminescent imaging, fluorescent imaging, CT, MRI, PET, SPECT, X-ray, and combinations thereof.

In some embodiments, the presently disclosed subject matter provides a method for treating a disease or condition, the method comprising administering to a subject in need of treatment thereof, a presently disclosed polymeric micellar nanoparticle composition, a polymeric micellar nanoparticle composition produced according to the presently disclosed methods, or a pharmaceutical composition thereof, in an amount effective for treating the disease or condition. In some embodiments, the nanoparticles can be delivered using a variety of routes including intravenous injection, intrabiliary infusion to target the liver, subcutaneous injection, intramuscular injection, and the like.

In some embodiments, the presently disclosed subject matter provides a method for preventing a disease or condition, the method comprising administering to a subject in need of prophylactic treatment thereof, a polymeric micellar nanoparticle composition comprising a block or graft copolymer comprising at least one polycationic polymer and at least one polyethylene glycol (PEG) polymer having an average molecular weight less than 1 kDa; and at least one nucleic acid; wherein the graft or block copolymer and the at least one nucleic acid are complexed and condensed into a shaped micellar nanoparticle that is stable in biological media, or a pharmaceutical composition thereof, in an amount effective for preventing the disease or condition. In some embodiments, preventing a disease or condition means generating protective immunity against the disease or condition, such as occurs when administering a vaccine to a subject. As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

The term "administering" as used herein refers to contacting a cell or portion thereof with a dose of the polymeric micellar nanoparticle composition. This term includes administration of the presently disclosed compounds to a subject in which the cell or portion thereof is present, as well as introducing the presently disclosed compounds into a medium in which a cell or portion thereof is cultured.

More particularly, as described herein, the presently disclosed nanoparticle compositions can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration," "administered systemically," "peripheral administration" and "administered peripherally" as used herein mean the administration of the presently disclosed nanoparticle compositions, a compound, drug or other material, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, drageemaking, levitating, emulsifying, encapsulating, entrapping or lyophilizing processes.

Pharmaceutical compositions for oral use can be obtained through a combination of nanoparticle compositions with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures.

Dyestuffs or pigments can be added to the tablets or dragee coatings for product identification or to characterize the quantity of nanoparticle compositions, e.g., dosage, or different combinations of doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, nanoparticle can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A).

Pharmaceutical compositions for parenteral administration include aqueous solutions of nanoparticle compositions. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of nanoparticle compositions or vehicles include fatty oils, such as sesame oil, or synthetic fatty acid esters, such as ethyl oleate or triglycerides, or liposomes. Optionally, the suspension also can contain suitable stabilizers or agents that increase the solubility of the nanoparticle compositions to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

The presently disclosed subject matter also includes the use of the presently disclosed nanoparticle compositions in the manufacture of a medicament for treating a disease or condition, such as cancer.

Regardless of the route of administration selected, the presently disclosed nanoparticle compositions are formulated into pharmaceutically acceptable dosage forms such as described herein or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed vaccine compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular nanoparticle composition employed, the route of administration, the time of administration, the rate of excretion of the particular vaccine being employed, the duration of the treatment, other drugs, vaccines and/or materials used in combination with the particular vaccine employed, the age, sex, weight, condition, general health and prior medical history of the patient being treated, and like factors well known in the medical arts.

A physician having ordinary skill in the art can readily determine and prescribe the effective amount of the nanoparticle composition required. Accordingly, the dosage range for administration will be adjusted by the physician as necessary.

Generally, doses of nanoparticle compositions will range from about 0.0001 to about 1000 mg per kilogram of body weight of the subject. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Synthesis of Linear Polyethylenimine-Graft-Polyethylene Glycol (lPEI-g-PEG) Copolymers lPEI (linear polyethyleneimine, molecular weight 22 kDa, 2.15 mg), sulfo-NHS (N-hydroxysulfosuccinimide, 1.09 mg) and A-PEG-COOH (functional polyethylene glycol acetic acid, molecular weight 500, 600, 750 or 2,000 Da, A-equals to methoxy, hydroxyl or 2-pyridyldithio groups) with different amounts according to the designed grafting density were dissolved in 1 mL of 0.05 mol/L pH 4.75 phosphate buffer. The pH of solution was monitored and kept in the range of 4.5-5 by adding either HCl or NaOH solution. EDC (1-ethyl-3-[3-dimethylaminopropyl] carbodiimide hydrochloride, 2.88 mg) was dissolved in 100 μL of ultrapure water and immediately added to the reaction mixture. Another 4 batches of EDC (same quantity) were added every other hour. The final product was purified by ultracentrifugation using a membrane with a molecular weight cutoff (MWCO) of 3,500 Da.

Preparation of lPEI-g-PEG/DNA Micelles with Different Morphologies

10 μg VR1255 plasmid DNA was dissolved in 100 μl DI water at a concentration of 100 μg/mL. Calculated amounts of lPEI-g-PEG polymer corresponding to different N/P ratios were also dissolved in DI water, followed by mixing with the plasmid DNA solution via pipetting to give a final DNA concentration of 50 μg/mL. As shown in FIG. 1, PEG grafting degree significantly influenced nanoparticle shape, even for small molecular weight PEG. At low grafting degree of 0.5%, particles are predominantly spherical. At 2% PEG grafting degree, rod-shaped particles are evident, further elongating to worm-like shapes at 8% PEG grafting degree.

Salt and Serum Stability of lPEI-g-PEG/DNA Nanoparticles Prepared with Small Molecular Weight PEG Good serum and salt stability of lPEI-g-PEG/DNA micelles prepared with small molecular weight PEG is desired for in vitro and in vivo transfections. If the size or shape of micelles was altered due to dissociation or aggregation upon the challenge of serum proteins or salts at physiological concentration, limited cell uptake, entrapment in capillaries or premature clearance by macrophages may lead to low transfection efficiency and limited biodistribution. To evaluate the serum and salt stability, lPEI-g-PEG/DNA micelles were prepared as described above. The serum stability of the micelles was first examined after the addition of 5% fetal bovine serum (FBS). The particle size of these lPEI-g-PEG/DNA micelles before and after the addition of serum was characterized using a dynamic lighting scattering detector. After incubation with serum for 30 min, nanoparticle size increased slightly, but lPEI/DNA nanoparticles prepared without PEG exhibited a drastic size increase, highlighting the importance of PEG in reducing aggregation (FIG. 2). The salt stability of the lPEI-g-PEG/DNA micelles exhibited reduced swelling in physiological salt conditions compared to lPEI/DNA nanoparticles.

In Vitro Transfection Efficiency of lPEI-g-PEG/DNA Micelles with Different Grafting Degrees and Molecular Weights In vitro gene transfection was performed in HeLa cells. Cells were maintained in Dulbecco's Modified Eagle's Medium supplemented with 10% fetal bovine serum at 37° C. and 5% $CO_2$. HeLa cells were seeded in 48-well plates at a density of $2\times10^4$ cells per well. After 24 h, lPEI-g-PEG/DNA micelles with different grafting degrees were added to each well at a dose of 0.5 µg of plasmid DNA. After 4 h of incubation, the culture media was replaced. Two days later, the culture media were removed, and cells were washed with 0.5 mL of phosphate buffered saline (pH 7.4). Cells were then lysed with a reporter lysis buffer (0.1 ml/well, Promega, Madison, Wis.), and subjected to two freeze-thaw cycles. Twenty µL of cell lysate supernatant was mixed with 100 µL of luciferase substrate (Promega), and the light units were measured on a luminometer (20/20n Single Tube luminometer, Turner BioSystems, Sunnyvale, Calif.). The luciferase activity was converted to the amount of luciferase using recombinant luciferase (Promega) as the standard, and normalized against protein content using the BCA protein assay (Bio-Rad Laboratories, Hercules, Calif.). As shown in FIG. 3, high transfection efficiency in vitro was observed, even at high PEG grafting degrees, when small molecular weight PEG was used. Conversely, when using 2 kDa PEG, transfection levels dropped to background levels even at 2% PEG grafting degree.

In Vivo Transfection Efficiency of lPEI-g-PEG/DNA Micelles with Different Grafting Degrees and Molecular Weights In vivo gene transfection was performed in male, 10 week old Balb/c mice using a luciferase reporter gene. Nanoparticles with a dose equivalent to 40 µg of plasmid DNA suspended in 5% glucose solution were administered via intravenous injection into the lateral tail vein. After 2 days, mice were sacrificed and major organs were collected. Organs were weighed and homogenized in 5 mL PBS (pH 7.4). Twenty µL of homogenate supernatant was mixed with 100 µL of luciferase substrate (Promega), and the light units were measured on a luminometer (20/20n Single Tube luminometer, Turner BioSystems, Sunnyvale, Calif.). The luciferase activity was then normalized against equivalent organ weight of the sample. As shown in FIG. 4, high transfection efficiency in vivo was observed for nanoparticles with PEG molecular weight of 700 Da. Particles prepared with 2 kDa PEG at equivalent PEG grafting degree displayed near background levels of luciferase expression.

Conjugation of Cell Targeting Ligand and In Vitro Transfection Following Ligand Conjugation lPEI-g-PEG/DNA nanoparticles were prepared as described, using a PEG with terminal succinimidyl 3-(2-pyridyldithio)propionate (SPDP) groups. Following nanoparticle formation, a solution containing a thiolated targeting molecule, in this case cyclic RGD peptide, was added to the nanoparticle solution at varying molar ratios of thiol on the ligand to SPDP on PEG. Ligand-containing particles were left to incubate for 4 hours prior to use. For in vitro transfection studies, MDA-MB-231 cells overexpressing αvβ3 integrin (the binding domain for RGD peptide) were used. Cells were maintained in RPMI-1640 media supplemented with 10% fetal bovine serum at 37° C. and 5% $CO_2$. Transfection results were performed as described previously. As shown in FIG. 5, no increase in transfection efficiency was observed for any nanoparticle prepared with 2 kDa PEG, following conjugation of RGD peptide. For particles prepared with 500 Da PEG, however, significant increase in transfection was observed following RGD conjugation, particularly for worm-shaped nanoparticles.

Example 2

Introduction

To fully harness the potential of nanoparticle-mediated drug delivery carriers following intravenous (i.v.) administration, control over their transport properties during circulation, tissue distribution, and cellular uptake must be controlled and improved. Recent reports have highlighted the role of nanoparticle shape during each of these stages of delivery (Geng et al., *Nat. Nanotechnol.* 2007, 2:249; Chauhan et al., *Angew. Chem. Int. Ed.* 2011, 50:11417; Jiang et al., *Adv. Mat.* 2013, 25:227). Previous work has shown the ability to tune and control the shape of polyethylene glycol (PEG)-polycation copolymer/DNA nanoparticle by altering particle assembly conditions and copolymer structure (Jiang et al., *Adv. Mat.* 2013, 25:227). While PEG is necessary for controlling shape and improving particle stability in physiological media, it significantly hinders the nanoparticle uptake and delivery efficiency. In this Example, a molecular design approach is reported to tune the shape of polymer/DNA nanoparticles while maintaining high transfection efficiency both in vitro and in vivo.

Materials and Methods

PEG with molecular weight of 2000 ($PEG_{2000}$) and 600 ($PEG_{600}$) were grafted to linear polyethylenimine (lPEI) at grafting degrees ranging from 0.25% to 8%. Nanoparticles were formed by pipetting equal volumes of copolymer and DNA solution at an N/P ratio of 8, after which the mixture was incubated for 20 min at room temperature before characterization. Particle size, surface charge, and TEM imaging were carried out according to published protocols (Jiang et al., *Adv. Mat.* 2013, 25:227; Jiang X. et al., *Pharm. Res.* 2011, 28:1317). For in vitro transfection experiments, nanoparticles containing 1 µg of luciferase pDNA were incubated with 20,000 HeLa cells per well for 48 h, followed by cell lysis and incubation with luciferase substrate (Jiang et al., *Adv. Mat.* 2013, 25:227; Jiang X. et al., *Pharm. Res.* 2011, 28:1317). For assessing the in vivo transfection efficiency, nanoparticles containing 40 µg luciferase DNA were injected into the tail vein of Balb/c mice; and organs were harvested and homogenized on day 3. The luminescence was measured in a luminometer and was normalized against the tissue weight.

Results and Discussion

Using both $PEG_{2000}$ and $PEG_{600}$, shape control of lPEI-g-PEG/DNA nanoparticles is evident (FIG. 6A, FIG. 6B, FIG. 6C, FIG. 6D, FIG. 6E and FIG. 6F). At the lowest grafting degree of 0.25%, particles adopted a compact, spherical morphology. For intermediate grafting degrees, spherical and rod-like particles dominate; and at the highest grafting degrees, particles assume string-like morphology, although the transition between shapes happened at lower grafting degrees for $PEG_{2000}$. In vitro transfection results showed that, at grafting degrees higher than 0.5%, $PEG_{2000}$ grafts dropped the transfection efficiency by 5 orders of magnitude to the background level. In contrast, $PEG_{600}$ grafts maintained high transfection levels (FIG. 6G). When comparing the in vivo transfection efficiency of nanoparticles prepared with $PEG_{600}$ and $PEG_{2000}$ at 0.5% grafting density, near background levels were observed for $PEG_{2000}$ grafts in all tested organs, whereas PEG$_{600}$ displayed significant levels of luciferase expression (FIG. 6H).

The presently disclosed subject matter shows that the shape of DNA nanoparticles can be controlled by condensing plasmid DNA with lPEI-g-PEG copolymers containing PEG grafts as short as 600 Da. PEG molecular weight was identified as the key parameter determining the transfection efficiency of shaped DNA nanoparticles. With optimized PEG grafts, high levels of transfection efficiencies were achieved in vitro and in vivo. This nanoparticle platform can be used for gene therapy applications.

Example 3

Introduction

In this present study, the physicochemical properties and transfection ability were specifically compared of nanoparticles prepared with lPEI grafted with PEG with molecular weight of 700 Da (PEG$_{7H}$) to those of 2000 Da (PEG$_{2K}$), the minimum PEG length typically recommended to afford the major benefits associated with PEGylation (Klutz et al. (2011) *Molecular Therapy: the Journal of the American Society of Gene Therapy* 19, 676-85; Rodl et al. (2013) *Methods in Molecular Biology* 948, 105-20). Many studies use PEG chain lengths much longer than this, ranging from 3400 Da to 20,000 Da for various DNA delivery applications (Nomoto et al. (2011) *Journal of Controlled Release: Official Journal of the Controlled Release Society* 151, 104-109; Osada, *Polym J* (2014) 46, 469-475; Yang et al. (2013) *Proc. Natl. Acad. Sci. U.S.A.* 110, 14717-14722; Erbacher et al. (1999) *Journal of Gene Medicine* 1, 210-222). Here, an lPEI-g-PEG/DNA nanoparticle system for effective in vivo delivery applications is reported, particularly for the detection of metastiatic prostate cancer. A series of lPEI-g-PEG carriers with different PEG grafting densities and PEG length (PEG7H and PEG2K) were used to assemble with plasmid DNA, forming various shaped micellar nanoparticles. Their shapes, surface characteristics, colloidal stability in salt and serum-containing media were correlated with their transfection efficiency in several cell lines, both in the absence and presence of cell adhesion peptides. Optimized carriers were tested following systemic injection in vivo using both Balb/c mice and metastatic prostate cancer-bearing mice. Using these nanoparticles, the ability of short PEG grafts for successful nanoparticle stabilization and efficient in vivo delivery was demonstrated. This work identified a key parameter for the development of effective non-viral gene carriers with significant potential for cancer detection and therapy.

Materials and Methods

Synthesis and characterization of lPEI-g-PEG copolymers: lPEI (linear polyethyleneimine, molecular weight 22 kDa, 2.15 mg), sulfo-NHS (N-hydroxysulfosuccinimide, 1.09 mg) and X-PEG-COOH (functional polyethylene glycol acetic acid, molecular weight 500, 600, 700 or 2,000 Da, X— represents methoxy, hydroxyl or SPDP terminal group) with different amounts according to the designed grafting density were dissolved in 1 mL of 0.05 mol/L pH4.75 phosphate buffer. The pH of solution was monitored and kept in the range of 4.5-5.0 by adding either 1 M HCl or 1 M NaOH solution. 1-Ethyl-3-[3-dimethylaminopropyl] carbodiimide (EDC) hydrochloride (2.88 mg) was dissolved in 100 µL of ultrapure water and immediately added to the reaction mixture. Another 4 batches of EDC (same quantity) were added every other hour. The final product was purified by ultracentrifugation using a membrane with a molecular weight cutoff (MWCO) of 3,500 Da.

Nanoparticle formation: Plasmid DNA, VR1255C (6400 kb), encoding the gene for firefly luciferase driven by the cytomegalovirus promoter, was kindly provided by Vical (San Diego, Calif.). Plasmid DNA was amplified in DH5α *E. coli* and was purified using an EndoFree Giga Kit (Qiagen, Valencia, Calif.) and dissolved at 1 mg/mL in endotoxin-free TE buffer. For a typical nanoparticle preparation, 10 µg of DNA was diluted in 100 µL of DI water to give a final concentration of 100 µg/mL DNA. A solution of lPEI-g-PEG was diluted to 100 µL in DI water to give a final N/P ratio (ratio of amine in lPEI to phosphate in DNA) of 8 as used in previous studies with PEG-polycation/DNA nanoparticles (Jiang et al. (2013) *Advanced Materials* 25, 227-232; Williford et al. (2014) *Journal of Materials Chemistry* 2, 8106-8109; Wei et al. (2015) *ACS Biomaterials Science & Engineering*). The polymer solution was added to the DNA solution and mixed by rapid pipetting, after which the polymer/DNA mixture was incubated for 10 min prior to further use.

Transmission electron microscopy: TEM imaging of nanoparticles was done by incubating 10 µL of lPEI-g-PEG/DNA nanoparticle solution onto an ionized nickel grid covered with a carbon film. After 10 min, the solution was removed, and a 6-µL drop of 2% uranyl acetate was added to the grid. After 20 s, the staining solution was removed, and the grid was dried at room temperature. The samples were imaged with a Technai FEI-12 electron microscope. Nanoparticle sizes were characterized from TEM images using Image J 1.44. Aspect ratios were determined by dividing the length of the nanoparticle by the diameter. At least 100 nanoparticles were measured from TEM images for each preparation.

Zeta potential measurement: Nanoparticle zeta potential was measured using a Zetasizer Nano ZS90 (Malvern Instruments, Southborough, Mass.). An aliquot of 5 µg DNA nanoparticle solution was diluted to 800 µL with DI water or 150 mM sodium chloride, added to a DTS1070-folded capillary cell, and measured in the automatic mode.

Nanoparticle stability characterization: To test the stability in physiological ionic strength solution, a pre-determined volume of 5 M NaCl solution was added to 5-µg DNA dose nanoparticle solution to give a final NaCl concentration of 150 mM. The mixture solution was incubated for 15 min, and then particle size was measured using dynamic light scattering method with a Zetasizer Nano Z590. To test the stability in serum, an aliquot of nanoparticle solution containing 5 µg of DNA was incubated with fetal bovine serum (FBS) at a final serum concentration of 5% (v/v) for 15 min before measuring the particle size.

DNA release from lPEI-g-PEG/DNA nanoparticles: The release of DNA from lPEI-g-PEG/DNA nanoparticles was assessed in the presence of heparin sulfate as modified from a previously reported protocol (Ren et al. (2010) *Biomacromolecules*, 11, 3432-3439. An aliquot of 20 µL of nanoparticles solution containing 1 µg of DNA was added to each well of a 96-well plate followed by the addition of 80 µL of 1 mg/mL ethidium bromide solution. To this solution, 100 µL of heparin sulfate solution with increasing concentrations in 300 mM NaCl solution was added to each well and mixed thoroughly, giving final heparin sulfate concentrations ranging from 1 µg/mL to 500 µg/mL in 150 mM NaCl. The solutions were incubated at room temperature for 15 min, and the fluorescence intensity ($\lambda_{ex}$=510 nm, $\lambda_{em}$=595 nm) was measured using a fluorescence plate reader (SpectraMax Gemini XPS, Molecular Devices, Sunnyvale, Calif.). The percentage of DNA released was calculated according to a calibration curve of plasmid DNA subjected to the same conditions.

Ligand conjugation to lPEI-g-PEG/DNA nanoparticles: Ligands were conjugated to polymer/DNA nanoparticles prepared with SPDP-PEG grafts through SPDP-thiol coupling chemistry. Cyclic RGD-thiol ligand (PCI-3686-PI, Peptides International, Louisville, Ky.) was dissolved in phosphate buffered saline (PBS) at 1 mg/mL according to the manufacturer's protocol. Peptide 947W (Ac-CCR-RYVVLPRWLC (SEQ ID NO: 1), ChinaPeptides Co., Ltd., Shanghai, China) was dissolved in PBS at 1 mg/mL. Briefly, lPEI-g-PEG(SPDP)/DNA nanoparticles were prepared as described above. Following particle incubation for 10 min, a solution containing the thiolated peptide at a 1:1 thiol: SPDP equivalent molar ratio was added to the nanoparticle solution. The nanoparticles were further incubated for 4 h to allow for peptide conjugation, after which they were used for further testing.

In vitro transfection of lPEI-g-PEG/DNA nanoparticles: The base media for maintaining PC3/ML cells, MDA-MB-231 cells, and HeLa cells were F-12K Nutrient Mixture (Kaighn's Modification, Life Technologies, Carlsbad, Calif.), RPMI-1640 media, and Dulbecco's Modified Eagle's Medium (DMEM), respectively. All media were supplemented with 10% FBS and 100 U/mL penicillin/100 µg/mL streptomycin, and cells were cultured at 37° C. and 5% $CO_2$. At 24 h prior to the transfection experiments, cells were seeded in 48-well plates at a density of $2\times10^4$ cells/well. Various nanoparticle solutions equivalent to 0.5 µg of DNA dose were added to the cells and incubated for 4 h, following which the media were refreshed. After 48 h, media were removed, and cells were washed with 1×PBS (pH 7.4). One hundred µL of reporter lysis buffer (Promega, Madison, Wis.) was added to each well. Cells were then subjected to two freeze-thaw cycles. Twenty µL of cell lysate from each well was assayed using a luciferase assay kit (Promega, Madison, Wis.) on a luminometer (20/20n, Turner BioSystems, Sunnyvale, Calif.). The luciferase activity was converted to the amount of luciferase expressed using a recombinant luciferase protein (Promega) as the standard and normalized against the total protein content in the lysate using a BCA assay (Pierce, Rockford, Ill.).

In vitro cellular uptake of lPEI-g-PEG/DNA nanoparticles: Cellular uptake efficiencies were measured in PC3 cells using tritium-labeled plasmid DNA. To prepare the radiolabeled DNA, plasmid DNA was methylated with CpG methyl transferase (M.SssL) (New England Biolabs, Ipswich, Mass.) and S-adenosyl-L-(methyl-3H) methionine (PerkinElmer, Waltham, Mass.) according to the manufacturer's protocol. Briefly, nuclease-free water, 10×NEB buffer, S-adenosyl-L-(methyl-3H) methionine, plasmid DNA, and M. SssL were mixed in order. The solution was then incubated at 37° C. for 1 h, and the reaction was quenched by heating to 65° C. for 20 min. The radiolabeled DNA was purified using Miniprep Kit (Qiagen, Valencia, Calif.). Radiolabeled lPEI-g-PEG/DNA nanoparticles were prepared as above by mixing radiolabeled DNA with non-radiolabeled DNA at 1/10 DNA weight ratio. At 24 h prior to the transfection experiment, PC3 cells were seeded in 48-well plates at a density of $2\times10^4$ cells/well. Nanoparticles containing 0.5 µg of labeled DNA were added to the cells according to the same protocol as described above in the transfection experiments. After 4 h of incubation, the media in each well was carefully removed, and the cells were washed with 200 µL of PBS. One hundred µL of reporter lysis buffer was added to each well, and cells were subjected to two freeze-thaw cycles. Fifty µL of cell lysate from each well was added to a scintillation vial and mixed with 4 mL of scintillation fluid. The radioactivity of each sample solution was measured on a liquid scintillation counter (TRI-CARB 1900 TR, Packard, Downers Grove, Ill.). Cell uptake percentage was calculated by dividing the radioactivity (in DPM) of each sample with the radioactivity of the total dose of nanoparticles added to each well.

Results and Discussion

Figure 9A:
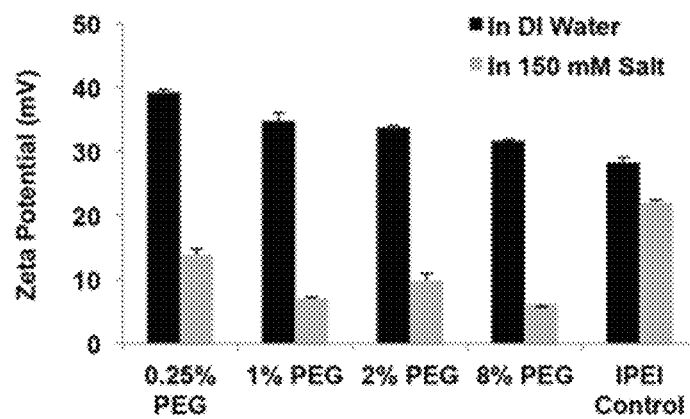
Figure 9B:
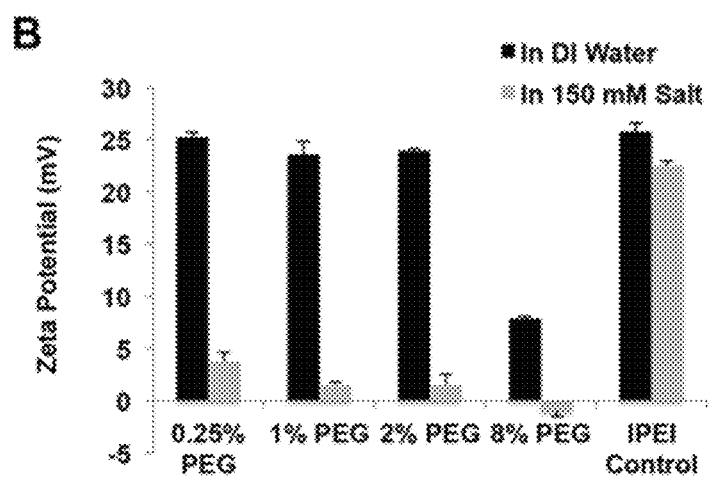

Short PEG grafts allow for shape control while maintaining stability: The presently disclosed subject matter closely examined the ability of short PEG grafts (MW<1 kDa) to confer nanoparticle assembly, shape control, colloidal stability, and transfection activity. Previously, few studies have examined the use of PEG chains with MW less than 1 kDa for nanoparticle surface stabilization, since PEG 2 kDa has been regarded as the minimum length for nanoparticle stabilization. In a report by Petersen et al. on plasmid DNA delivery, a branched polyethylenimine (bPEI)-g-PEG copolymer with 35 of PEG (550 Da) grafts per PEI chain was used to prepare DNA micellar nanoparticles (*Bioconjugate Chemistry*, 2002, 13, 845-54). Compared to higher molecular weight PEG grafts, 550 Da PEG-grafted bPEI showed the best transfection properties in vitro, albeit lower colloidal stability in serum containing medium. There was no further systematic optimization of the nanoparticles prepared with short PEG grafts. In this study, a series of $lPEI_{22K}$-g-PEG/DNA nanoparticles with two different PEG graft lengths—$PEG_{7H}$ and $PEG_{2K}$ and various PEG grafting degrees ranging from 0.25% to 8% (molar percentage of PEG chains compared to total amount of amines on lPEI) was prepared. As the PEG grafting degree increases for both $PEG_{7H}$ and $PEG_{2K}$ grafts, $lPEI_{22K}$-g-PEG/DNA nanoparticles underwent a significant shape variation, with particles adopting a condensed spherical and short rod shapes at 0.25% grafting degree, and extending to longer worm-like shape at higher grafting degrees of 2% and 8%. Nanoparticle shape transition from spherical to rod-like morphology occurred at slightly lower grafting degree (1%) for $PEG_{2K}$ grafts and also led to longer worm-like shapes with higher aspect ratios compared to nanoparticles prepared with $PEG_{7H}$ grafts. These results are consistent with previous results observed for PPA-g-PEG/DNA nanoparticles with varying PEG chain lengths, where longer PEG chains led to more elongated nanoparticle shapes at increasing PEG grafting degrees of 2% and 4% (Wei et al. (2015) *ACS Biomaterials Science & Engineering*). Aspect ratio quantification from the TEM images confirmed these trends with nanoparticles prepared with both PEG grafts displayed aspect ratios of ~1.5 at 0.25% grafting degree, transitioning to aspect ratios of 20 and 36 at 8% grafting degree for $PEG_{7H}$ and $PEG_{2K}$, respectively (FIG. 8). Next, the surface charge of lPEI-g-PEG/DNA nanoparticles in both water and 150 mM salt was measured. Nanoparticles prepared with $PEG_{7H}$ grafts maintained a positive surface charge greater than +30 mV in water; after incubation in salt, however, surface charges dropped significantly to +13 mV for 0.25% grafting degree. Similar drops were observed for all $PEG_{7H}$-grafted polymers, whereas lPEI control particles maintained a positive charge of +22 mV in salt (FIG. 9A). These results indicate that short PEG grafts can still mask the positive surface charge even at low grafting degrees. It is important to note that the surface charge of lPEI control particles is lower in water compared to $PEG_{7H}$-grafted nanoparticles, likely due to the fact that N/P 5 was used for lPEI control particles whereas N/P 8 was used for PEG-grafted nanoparticles. Similar results were observed for particles prepared with PEG$_{2K}$ grafts, although the drops in surface charge for these particles were greater after incubation in salt (FIG. 9B). This observation can be attributed to stronger charge screening effect of the longer PEG grafts.

Figure 9C:
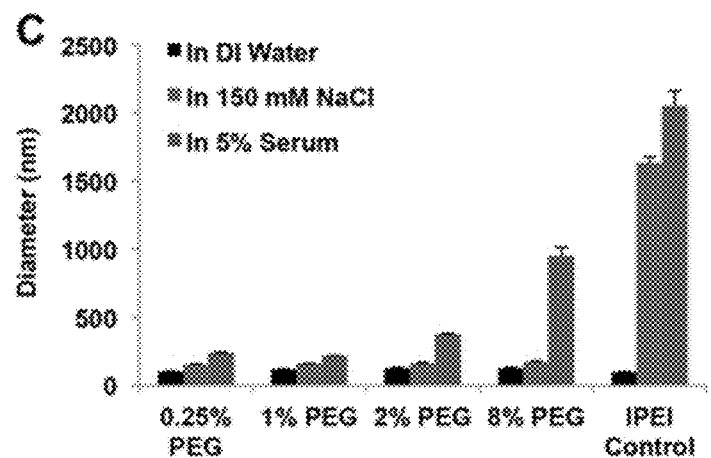
Figure 9D:
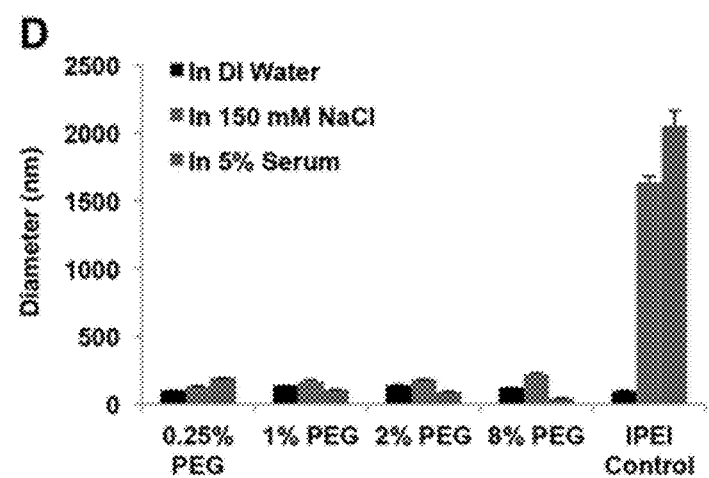

To confirm that the short, PEG$_{7H}$ grafts could improve the stability of lPEI-g-PEG/DNA nanoparticles, each series of particles was incubated in 5% serum and 150 mM NaCl solution for 15 min. Particles prepared with both PEG lengths showed significant improvements in nanoparticle stability compared to lPEI control particles, which rapidly aggregated from 100 nm in water to 1.6 µm in 0.15 M NaCl solution and 2 µm in 5% serum after the 15 min incubation period (FIG. 9C and FIG. 9D). PEG$_{7H}$-grafted particles showed slight increases in 5% serum, although size generally remained below 400 nm. Only 8% PEG$_{7H}$ grafts showed significant aggregation in serum, although it is possible that this is due to limitations with dynamic light scattering measurements of non-spherical particles since particles with lower PEG density showed no aggregation. All particles prepared with PEG$_{2K}$ grafts showed no detectable aggregation in salt or serum-containing media.

PEG chain length significantly influences in vitro transfection efficiency: The series of nanoparticles prepared with either PEG$_{7H}$ or PEG$_{2K}$ grafts were evaluated for their transfection efficiency in vitro using a luciferase reporter plasmid DNA in three separate cell lines: PC3 prostate cancer cells, MDA-MB-231 breast cancer cells, and HeLa cells. In all cell lines, PEG$_{7H}$-grafted particles displayed higher transfection efficiency compared to PEG$_{2K}$-grafted particles at similar grafting degrees (FIG. 10A and FIG. 11). For example, in PC3 cells, particles prepared with 0.25% PEG$_{7H}$ grafts showed nearly 100-fold higher transfection efficiency compared to PEG$_{2K}$-grafted particles. As the shape of these two particles is identical, it is likely that PEG chain length is a major determining factor in the differences in gene expression. At grafting degrees of 1% or higher, PEG$_{2K}$-grafted particles mediated near-background levels of gene expression, whereas efficiency of PEG$_{7H}$-grafted particles was significantly higher. While PEG$_{2K}$-grafted nanoparticles had higher aspect ratios, the overall shape of micelles prepared with both PEG grafts was similar, highlighting the importance of short PEG grafts in maintaining high transfection efficiency. Similar trends were observed in both MDA-MB-231 cells and HeLa cells (FIG. 11), although the absolute level of gene expression varied between cell lines. More importantly, even the worm-shaped nanoparticles prepared with 8% PEG$_{7H}$ grafts, suggesting sufficiently high particle surface PEG graft density in order to confer the elongated morphology, maintained high transfection efficiency in HeLa cells.

To understand the differences in transfection observed when varying PEG graft length, the cellular uptake efficiency of each series of nanoparticles in PC3 cells was evaluated using tritium-labeled DNA (FIG. 10B). At 0.25% grafting degree, both PEG$_{7H}$ and PEG$_{2K}$-grafted nanoparticles exhibited high cellular uptake efficiency. At all other grafting degrees, PEG$_{7H}$ maintained high cellular uptake efficiency, whereas PEG$_{2K}$ decreased cellular uptake to near-background levels. Uptake levels do not correlate exactly with the observed PC3 transfection results, which may be due to other barriers in the delivery process such as endosomal escape, nuclear translocation, and intracellular release of plasmid DNA. For example, 0.25% PEG$_{2K}$-grafted nanoparticles showed higher cell uptake but lower gene expression compared to PEG$_{7H}$-grafted nanoparticles, possibly due to incomplete cellular internalization or poor endosomal escape, two limitations previously associated with longer PEG grafts (Li et al. (2014) *Biomaterials* 35, 8467-8478; Mishra et al. (2004) *Eur J Cell Biol* 83, 97-111). On the other hand, PEG$_{7H}$-grafted nanoparticles exhibited similarly high cellular uptake but reduced transfection efficiency at grafting degrees higher than 1%. In these cases, the worm-shaped nanoparticles may also suffer from poor or incomplete cellular internalization due to their high aspect ratio. An additional possibility for the differences observed in transfection efficiency between PEG$_{7H}$- and PEG$_{2K}$-grafted nanoparticles is on intracellular DNA release. However, as shown in FIG. 12, following challenge from varying concentrations of heparin sulfate, nanoparticles at all PEG grafting degrees showed similar DNA release characteristics, regardless of PEG chain length. At higher PEG grafting degrees, PEG$_{2K}$-grafted particles released DNA at slightly lower concentrations of heparin sulfate, indicating higher propensity to release the condensed DNA. As all densities of PEG$_{2K}$-grafted particles demonstrated lower transfection efficiency compared to PEG$_{7H}$, it is not likely that DNA release rate represents a major factor affecting transfection ability of these nanoparticles.

In addition to PEG$_{7H}$-grafted nanoparticles, a series of PEG$_{6H}$ (600-Da PEG chain)-grafted particles with similar grafting degrees was prepared; the PEG$_{6H}$ grafts, however, were terminated with hydroxyl groups whereas the PEG$_{7H}$ grafts were terminated with methoxy groups. For all grafting degrees tested, hydroxyl-terminated lPEI-g-PEG$_{6H}$/DNA nanoparticles exhibited markedly higher transgene expression levels in PC3 cells (FIG. 13). These results suggest that the PEG terminal end group, and hence nanoparticle surface chemistry, significantly influence gene delivery efficiency. Combining a short PEG chain with hydroxyl terminal groups may prove beneficial for future gene therapy applications.

PEG spacer length significantly influences transfection efficiency of ligand-conjugated nanoparticles: Ligand conjugation to the terminal end of PEG chains is a popular strategy to overcome the reduction in nanoparticle delivery efficiency following PEGylation strategies designed to improve nanoparticle stability (Zhong et al. (2014) *Biomacromolecules* 15, 1955-69. To evaluate the effect of PEG chain length on transfection improvement following ligand conjugation, a series of lPEI-g-PEG/DNA nanoparticles comprised of PEG$_{5H}$ and PEG$_{2K}$ grafts was prepared, containing a terminal 2-pyridyldithio (SPDP) group. SPDP chemistry is useful for ligand conjugation, as sulfhydryl-containing molecules react with high efficiency to the SPDP groups (Carlsson et al. (1978) *The Biochemical Journal* 173, 723-37; Hermanson (2013) *Bioconjugate Techniques, 3rd Edition*, 1-1146). Furthermore, ligand conjugation can be performed following nanoparticle formation, increasing the likelihood that the ligand is effectively presented on the nanoparticle surface as opposed to being embedded in the corona or core of the nanoparticles.

As a proof-of-principle, a laminin-derived peptide, RYVVLPR (SEQ ID NO: 2) (full sequence Ac-CCR-RYVVLPRWLC (SEQ ID NO: 1)) was conjugated to the SPDP terminal groups following nanoparticle formation at a 1:1 molar ratio of thiol in the peptide to SPDP on the nanoparticle surface. This peptide has been used previously to promote neural stem cell adhesion on various substrates (Li et al. (2014) *Stem Cells Translational Medicine* 3, 662-70). While it has not previously been reported to enhance nanoparticle delivery efficiency, certain cancer cells, including metastatic prostate cancer cells, up-regulate expression of integrins that bind to laminin (Dedhar et al. (1993) *Clin Exp Metastas* 11, 391-400; King et al. (2008)

Plos One 3; Nagle et al. (1995) *Am J Pathol* 146, 1498-1507). Therefore, RYVVLPR (SEQ ID NO: 2) peptides may be a unique ligand to enhance lPEI-g-PEG/DNA nanoparticle binding to these cancer cells.

Following transfection of PC3 cells in vitro, $PEG_{5H}$-grafted nanoparticles terminated with RYVVLPR (SEQ ID NO: 2) peptides mediated significantly higher transfection efficiency than those without ligands (FIG. 14A). The largest increases were observed for 2% and 8% PEG grafting degrees, which correlates to nanoparticles with elongated rod-like and worm like shapes. These results are consistent with reports in the literature showing the importance of elongated shapes for cellular binding when conjugated with specific antibodies targeting breast cancer cells in vitro and lung and tumor tissue in vivo (Barua et al. (2013) *Proc. Natl. Acad. Sci. U.S.A.* 110, 3270-5; Kolhar et al. (2013) *Proc. Natl. Acad. Sci. U.S.A.* 110, 10753-8). In contrast, when RYVVLPR (SEQ ID NO: 2) peptide was conjugated to $PEG_{2K}$-grafted nanoparticles, no improvement in transfection efficiency was observed for all PEG grafting degrees tested (FIG. 14B). All tested conditions displayed near-background levels of transfection efficiency in PC3 cells. While the effect of PEG chain length on cellular uptake differences following ligand conjugation has not been systemically studied in polymeric nanoparticles, a recent study using liposomes reported ligand conjugation to short, 350-Da PEG linkers led to the greatest increase in cell uptake efficiency (Stefanick et al. (2013) *ACS Nano*, 7, 2935-47.

To confirm that this result was specific to this particular ligand or cell type, cyclic RGD-thiol peptide (cRGD) was conjugated to the SPDP terminals and the transfection efficiency was evaluated in MDA-MB-231 cells overexpressing integrin $\alpha_v\beta_3$, the specific receptor associated with RGD binding (Shallal et al. (2014) *Bioconjugate Chemistry* 25, 393-405. Results from this study, shown in (FIG. 15), confirmed the observations in PC3 cells. Transfection efficiency increases were only observed when cRGD was conjugated to $PEG_{5H}$ grafts, particularly at 8% grafting degree. No significant transgene expression was observed when cRGD peptide was conjugated to nanoparticles with $PEG_{2K}$ grafts.

In this study, the importance of short PEG grafts (MW<1 kDa) has been demonstrated for achieving balanced colloidal stability, shape control, and gene transfection efficiency when engineering DNA compacting micellar nanoparticles for cancer imaging and therapy. The PEG grafts with MW as low as 500-700 Da (equivalent to an average degree of polymerization of 11.4-16) was effective in conferring shape control ability by varying PEG grafting degree and increasing nanoparticle stability in salt and serum-containing media, displaying reduced surface charges and significantly reduced aggregation, compared to lPEI/DNA control particles. Importantly, short PEG grafts yielded high transfection efficiency for these lPEI-g-PEG/DNA micellar nanoparticles. Moreover, hydroxyl terminal group of PEG grafts, as opposed to methoxyl groups, further increased transfection efficiency for nanoparticles with short PEG grafts. Finally, the short PEG grafts were also crucial to realizing the ligand-enhanced transfection activity for these micellar nanoparticles. Taken together, the presently disclosed subject matter provides PEG graft length and terminal groups for lPEI-g-PEG/DNA micellar nanoparticles to achieve shape control, high colloidal stability and high transfection efficiency for in vivo gene delivery applications.

Example 4

The presently disclosed subject matter provides polymer/DNA micelles via optimizing PEG graft length to achieve shape control and micelle stability in physiological media, as well as improved transfection efficiency in vitro and gene delivery efficiency in vivo.

FIG. 16A shows a schematic illustration of the critical factors for shape control in lPEI-g-PEG/DNA micelle assembly. In this study, molecular weight (MW) of lPEI was fixed at 22 KDa and PEG graft was chosen with MW of 2000 and 700 Da. By varying the grafting degree of PEG, copolymer/DNA micelles were generated with shapes ranging from more condensed spherical to more relaxed rod-like and worm-like morphologies. TEM images show the shape variations at 0.5% PEG grafting degree (FIG. 16B and FIG. 16E), 2% PEG grafting degree (FIG. 16C and FIG. 16F), and 8% PEG grafting degree (FIG. 16D and FIG. 16G) for $PEG_{2000}$ and $PEG_{700}$, respectively. The surface charge of lPEI-g-$PEG_{700}$/DNA micelles prepared with different PEG grafting degrees (FIG. 17A) and colloidal stability of lPEI-g-$PEG_{700}$/DNA nanoparticles as measured by dynamic light scattering (FIG. 17B) are shown.

Transgene expression in PC3 prostate cancer cells following transfection with lPEI-g-PEG/DNA micelles prepared with $PEG_{700}$ and $PEG_{2000}$ at different grafting degrees (FIG. 18A) and in vivo transfection in different organs of Balb/c mice following i.v. injection of spherical lPEI-g-PEG/DNA micelles (FIG. 18B) showed that in vitro and in vivo transfection efficiency is dependent on PEG molecular weight. In addition, RGD peptides were conjugated to copolymer/DNA micelles to facilitate cell binding and uptake (FIG. 19). It was found that in vitro transfection efficiency of the lPEI-g-PEG/DNA micelles in MDA-MB-231-$\alpha_v\beta_3$ cells was also dependent on PEG molecular weight.

In vivo bioluminescence images were taken of PC3 metastatic prostate cancer (PCa)-bearing mice following i.v. injection of jetPEI/DNA and lPEI-g-$PEG_{600}$/DNA micelles containing firefly luciferase-expressing plasmid under the control of tumor-specific promoter and showed increased bioluminescence signal with the PEG grafting degree at 0.5% and 1% (Bhang, *Nat. Med.* 2011; 17: 123) (FIG. 20A). Quantitative comparison of the bioluminescence signal in liver and lung for lPEI-g-$PEG_{600}$/DNA micelles and jetPEI/DNA nanoparticles (FIG. 20B) showed a significant increase in the liver/lung luminescence ratio with the lPEI-g-$PEG_{600}$/DNA micelles. In vitro transfection of PC3 cells following treatment with lPEI-g-$PEG_{500}$/DNA micelles conjugated with cell adhesion peptides RGD, RYVVLPR (SEQ ID NO: 2), and YIGSR (SEQ ID NO: 3) showed increased luciferase expression relative to cells treated with micelles without ligands (FIG. 20C). Bioluminescence imaging of PCa-bearing mice following i.v. injection of jetPEI/DNA nanoparticles and peptide-conjugated lPEI-g-$PEG_{500}$/DNA micelles under the control of tumor-specific promoter is shown in FIG. 20D. FIG. 21 shows the relative metabolic activity in PC3 cells comparing peptide-conjugated lPEI-g-$PEG_{500}$/DNA micelles, lPEI-g-$PEG_{600}$/DNA micelles, and jetPEI/DNA nanoparticles.

This study identifies a set of key polymer structure parameters necessary for shape control of lPEI-g-PEG/DNA micelles, PEG MW and grafting degree, and demonstrates that shape control is feasible even with short PEG grafts. Short PEG grafts can effectively improve particle stability in physiological media, facilitate ligand-mediated transfection for micelles conjugated with cell binding peptides, and most importantly, lead to significant improvements in gene delivery efficiency both in vitro and in vivo. Using a mouse model of human metastatic prostate cancer, successful intravenous delivery of tumor-specific promoter driven plasmid DNA with high delivery efficiency and reduced cytotoxicity has been demonstrated. The conditions identified here are also applicable to other DNA micelle systems. This study leads to improved nonviral nanocarriers for gene therapy applications.

Example 5

Challenges Associated with Systemic Delivery of Imaging and Therapeutic Nanoparticles Mortality from most malignancies derives from the presence of widespread metastases. Therefore, imaging and therapeutic strategies that can diagnose and treat both localized and metastatic tumors would provide the best coverage and treatment outcome. For this, systemic delivery is required to achieve greatest access to the localized and metastatic tumors, particularly for smaller tumor nodules, i.e., micro-metastases. The biggest challenge for systemic delivery of nanotherapeutics is the low colloidal stability and poor control of transport properties following intravenous injection. Numerous nanoparticle systems for therapeutic delivery applications have been developed over the past decades (Peer et al. (2007) Nature Nanotechnology 2, 751-760; Pack et al. (2005) Nature Reviews Drug Discovery (2005) 4, 581-593; Davis (2009) Molecular Pharmaceutics 6, 659-668; Davis et al. (2010) Nature 464, 1067-1140; Love et al. (2010) Proc. Natl. Acad. Sci. USA 107, 1864-1869; Wei et al. (2013) Angewandte Chemie-International Edition 52, 5377-5381). However, of particular concern for nanoparticles in gene delivery is the limited tissue distribution of the nanoparticles. Common gene carriers, such as polyethyleneimine (PEI), are highly cationic, which often leads to expression of the DNA payload solely in the lungs (Navarro et al. (2010) Journal of Controlled Release 146, 99-105). Aside from tissue physiology, the main barrier remains the lack of control and poor understanding of nanoparticle transport properties in physiological media. This knowledge gap represents a critical challenge faced by nanotherapeutics following systemic administration. This study specifically addresses this challenge for DNA polyplex delivery systems.

Murine Models of Human Metastatic Cancers and Detection by Bioluminescence Imaging (BLI) and SPECT/CT Imaging (Bhang, Nat. Med. 2011; 17:123-129 and Unpublished Results)

Previous studies have resulted in the development of metastatic tumor models using human melanoma (Bhang, Nat. Med. 2011; 17:123-129), breast cancer (Bhang, Nat. Med. 2011; 17:123-129), and prostate cancer cell lines. Following i.v. injection of MDA-MB-231 breast cancer cells or PC3/ML prostate cancer cells in NOD/SCID/IL2r$\gamma^{null}$ (NSG) mice, metastatic lesions develop in the lung, liver, kidney and bone. These studies have shown that systemically delivered jet-PEI™/DNA nanoparticles containing a plasmid vector encoding the firefly luciferase (fLuc) reporter driven by a tumor specific prompter can effectively detect metastatic tumor nodules in different tissues using both in vivo BLI and SPECT/CT techniques (FIG. 22; Bhang, Nat. Med. 2011; 17:123-129). H&E, human pan-cytokeratin, and anti-luciferase staining (FIG. 22A, FIG. 22B, FIG. 22C, FIG. 22D, FIG. 22E and FIG. 22F) on the consecutive sections of tissues that exhibited BLI signals in live-animal imaging, confirmed that the in vivo BLI offers sufficient sensitivity to track metastatic lesions in these mouse models. To further validate this, another reporter plasmid encoding herpes simplex virus 1 thymidine kinase (HSV1-TK) with the same expression construct was delivered similarly, and mice were imaged by a clinical molecular imaging modality, single-photon emission computed tomography (SPECT)/CT technique following injection of 2'-fluoro-2'-deoxy-β-d-5-[$^{125}$I]iodouracil-arabinofuranoside ([$^{125}$I]FIAU). Both malignant lung lesions and extrathoracic micro-metastases showed on average about 30-fold higher accumulation of [$^{125}$I]FIAU than controls (FIG. 22G, FIG. 22H, FIG. 22I, FIG. 22J, FIG. 22K, FIG. 22L, FIG. 22M and FIG. 22N; Bhang, Nat. Med. 2011; 17:123-129). Recently, a prostate cancer metastasis model using a PC3-ML prostate cancer cell line has been developed using a similar protocol described in FIG. 22A, FIG. 22B, FIG. 22C, FIG. 22D, FIG. 22E, FIG. 22F, 22G, FIG. 22H, FIG. 22I, FIG. 22J, FIG. 22K, FIG. 22L, FIG. 22M and FIG. 22N. Through systemic, jet-PEI polyplex-based delivery of similar imaging constructs of fLuc and HSV1-tk, lesions can also be identified through BLI and SPECT/CT techniques with high sensitivity (data not shown). The method compares favorably to accepted and emerging clinical PET standards. In the proposed study, these metastatic tumor models and imaging techniques can be used to demonstrate the shape-dependent delivery efficiency with the optimized DNA micelles.

Evaluate Shape-Dependent Micelle Delivery of a Theranostic Gene and Subsequent Imaging/Therapy Using Murine Models of Human Metastatic Cancers To demonstrate the shape-dependent delivery efficiency of DNA micelles in a clinically relevant model, metastatic tumor models and the molecular-genetic imaging method developed previously (Bhang, Nat. Med. 2011; 17:123-129) can be adopted. NOD/SCID/IL2r$\gamma^{null}$ (NSG) mice and two different cell lines can be used to cover several types of metastases. The MDA-MB-231 breast cancer cells (two million per mouse, i.v.) have a stronger bias in generating large lung malignancies, whereas PC3/ML prostate cancer cells (2 million per mouse, i.v.) primarily generate robust liver, kidney, and bone metastatic lesions. Use of these two models can cover a wide range of metastasis targets. These mice start to develop palpable metastatic legions three weeks after injection and die by about six weeks due to the metastatic diseases. These murine models can be used to test imaging and treatment tumors in the lung, liver, kidney and bone using a theranostic vector expressing firefly luciferase (fLuc) as an imaging reporter, and herpes simplex virus 1 thymidine kinase (HSV1-tk) as both a SPECT/CT imaging reporter and as a therapeutic approach following the injection of Gancyclovir.

For the proposed studies, a theranostic vector with both fLuc and HSV1-tk gene driven by a constitutively active SV40 promoter can be used, rather than one with a tumor-specific promoter, to compare the intrinsic delivery and targeting ability of the shaped micelles. It has been shown that SV40 and the cancer specific promoter have similar promoter activities (Bhang, Nat. Med. 2011; 17:123-129). In this plasmid vector, an EBV origin of replication (OriP) and Epstein-Barr nuclear antigen (EBNA-1) were inserted before the fLuc gene and HSV1-tk gene to enable prolonged transgene expression without random genomic insertion (Young and Murray (2003) Oncogene 22, 5108-5121) as well as a transcriptional amplification (TA) machinery for elevated expression of the dual genes (Kishimoto et al. (2006) *Nature Medicine* 12, 1213-1219). This construct has been confirmed to enhance transgene expression by more than 10-fold than that without TA element (data not shown). Conjugate the Cyclic RGD Peptide or the Prostate-Specific Membrane Antigen (PSMA)-Binding Ligand to Shaped Micelles and Demonstrate their Effect on Transfection Efficiency To prompt cellular binding and uptake of DNA micelles, a cyclic RGD peptide has been conjugated onto the surface of a set of shaped micelles using a scheme similar to that for DOTA conjugation, and it has been shown that ligand-conjugated micelles exhibited higher transfection efficiency; in particular it drastically increased efficiency for worm-like micelles. Besides testing these peptide-conjugated micelles, the PSMA-binding ligand can be conjugated to the shaped micelles and tested in tumor models generated from PSMA$^+$-PC3/ML cells. The densities of surface-decorated ligands can be further modulated to maximize cell binding and uptake, which can be measured using micelles prepared with $^3$H-labeled DNA. These measurements can be correlated with their transfection efficiencies in PSMA$^+$ and PSMA$^-$ cancer cells.

Tumors are heterogeneous and do not always express what can be considered reliable, tumor-selective markers, suggesting the need to incorporate multiple moieties enabling concurrent targeting to different putative receptors. Previous studies have reported an imaging agent targeting both PSMA and $\alpha_v\beta_3$ integrin, each overexpressed in primary tumors, neovasculature, and metastatic lesions, which can identify two structurally and functionally different cancer-selective surface proteins (Shallal et al. (2014) *Bioconjugate Chemistry* 25, 393-405). Both PSMA ligand (Cho et al. (2012) *Journal of Nuclear Medicine* 53, 1883-1891) and cyclic RGD peptide (Oe et al. (2014) *Biomaterials* 35, 7887-7895) can be conjugated onto shaped micelles to target metastatic tumors generated with cells overexpressing PSMA and/or integrin-$\alpha_v\beta_3$.

Compare Delivery Efficiency of the Theranostic Vector by Shaped Micelles for their Ability to Image Metastatic Lesions at Lung, Liver, Kidney and Bone; Evaluate Efficacy of Evaluate Efficacy of the Therapy Via Delivered Therapeutic Gene DNA micelles can be selected with optimal cellular uptake and transfection efficiency and favorable transport properties, as well as a set of micelles with other shapes as controls, to investigate their transgene expression efficiency in vivo using the metastatic models of human cancers. Once the metastatic tumor establish, the following experiments can be performed for each model with selected micelles. Two weeks after the cell injection, mice can be culled into groups. The experimental groups can receive (i.v.) shaped micelles formulated with the theranostic vector, such as an amount of 40 µg. Control groups can receive DNA/jet-PEI polyplexes with the same theranostic vector as a benchmark, micelles with an imaging vector containing fLuc gene only (control for the treatment groups), plasmid only, and PBS only. By following fLuc expression, the peak transgene expression has been identified at 48 h after the injection of spherical I-PEI-g-PEG/DNA micelles and jet-PEI control (FIG. 23). This capability helps to determine the best treatment time points. The expression level outside thoracic regions was much higher for a spherical l-PEI-g-PEG micelle formulation than jet-PEI group, corroborated with less aggregation and higher colloidal stability of the DNA micelles in contrast with 1-PEI/DNA complexes in serum containing medium.

Starting 48 h after the injection of micelles, mice can receive Gancyclovir i.p., twice a day for 5 days (150 mg/kg in 200 µL in 0.9% NaCl) for therapy. Metastatic tumor growth can be monitored by BLI before treatment and weekly after the treatment. At each time point (weeks 3, 4, and 5 post cell injection), animals can be imaged with $^{125}$I-FIAU SPECT/CT to confirm tumor growth (offers enhanced tissue penetration of signals than BLI) (Bhang, *Nat. Med.* 2011; 17:123-129), and subsequently sacrificed for histological analyses of the tumor development and PCR-based analysis of gene expression. The histological data can be co-registered with images to assess the ability of imaging to detect all metastatic lesions identified by histological examination as described previously (Bhang, *Nat. Med.* 2011; 17:123-129). Tumor size can be recorded at each time point to score the efficacy of the therapies. The remaining mice from each group can be monitored for survival study to evaluate Gancyclovir-mediated therapeutic efficacy. The endpoint of monitoring can be the death of animal. The total time taken to reach the endpoint and the status of metastatic development for each week can be recorded.

In parallel, the shape-dependent biodistribution and tumor-specific uptake can be probed after i.v. injecting micelles prepared with tritium-labeled plasmid DNA at 2 h and 1 day (n=5). The differences in transport properties of shaped micelles between normal and tumor-bearing mice can be compared. Also, levels of tissue damage and toxicity associated with different shaped micelles can be compared by tissue histochemical analysis in vital organs and by blood chemistry for alanine aminotransferase (ALT), aspartate aminotransferase (AST), and alkaline phosphatase (ALP) assays (Jiang et al. (2010) *Journal of Controlled Release* 122, 297-304). Previous studies have shown that DNA micelles prepared with PEG corona resulted in minimal hepatic toxicity following i.v. and site-specific intrabiliary infusion (Jiang et al. (2007) *Journal of Controlled Release* 122, 297-304).

It is hypothesized that BLI signal intensity, which represents fLuc expression, will be higher in mice with untreated cancer control than in the treated experimental group. 7-fold and 20-fold higher bioluminescence imaging intensity in breast cancer and melanoma models, respectively, have previously been observed (Bhang, *Nat. Med.* 2011; 17:123-129), and this advanced theranostic vector is expected to have similar or enhanced activity in other cancer models.

Example 6

In Vivo Transfection Efficiency of lPEI-g-PEG/DNA Micelles with Different Molecular Weights Following Ligand Conjugation In vivo gene transfection was performed in male, 10 week old Balb/c mice using a luciferase reporter gene. Nanoparticles with a dose equivalent to 40 µg of plasmid DNA suspended in 5% glucose solution were administered via intravenous injection into the lateral tail vein. After 2 days, mice were injected with 100 uL of 25 mg/mL of D-luciferin potassium salt (Gold Biotechnologies) and imaged via IVIS Spectrum under anesthesia administered with isoflurane. As shown in FIG. 24, increased transfection efficiency due to cell binding ligand conjugation was only observed with PEG molecular weight of 500 Da (p<0.05). Particles prepared with 2 kDa PEG at equivalent PEG grafting degree displayed near background levels of luciferase expression. As shown in FIG. 25A, FIG. 25B, FIG. 25C, and FIG. 25D, ligand-conjugated DNA nanoparticles with short PEG5H grafts effectively detected metastatic prostate cancer lesions in vivo.

In Vivo Hepatotoxicity of lPEI-g-PEG/DNA Micelles with Different Molecular Weights Following Ligand Conjugation In prostate cancer-bearing mice, RYVVLPR-conjugated lPEI-g-PEG$_{5H}$/DNA nanoparticles at 0.2% grafting degree displayed the highest levels of gene expression in organs with high tumor burden: liver, kidney, and lung, in comparison with lPEI-g-PEG5H/DNA and in vivo jetPEI control (FIG. 6A, FIG. 6B, FIG. 6C, FIG. 6D, FIG. 6E, FIG. 6F, FIG. 6G, and FIG. 6H). To quantify the level of gene expression, major organs were collected and homogenized, and firefly luciferase activity was quantified using a luciferase assay. Compared to nanoparticles without ligands, RYVVLPR-conjugation improved gene expression levels by 3.7-fold, 3.9-fold, and 2.8-fold in the lung, liver, and kidney, respectively (FIG. 6B, FIG. 6C and FIG. 6D). Additionally, compared to in vivo jetPEI control nanoparticles, RYVVLPR-conjugated nanoparticles increased expression levels by 2.3-fold, 2.3-fold, and 2.7-fold in the lung, liver, and kidney, respectively. It is important to note that due to the presence of the tumor-specific promoter driving the expression of luciferase marker gene, all detected gene expressions are localized to the PC3-ML prostate cancer cells.

Nanoparticles with a dose equivalent to 40 µg of plasmid DNA suspended in 5% glucose solution were administered via intravenous injection into the lateral tail vein. After 2 days, 400 uL of blood was collected via facial bleeding and plasma separator tubes (BD Microtainer) were used to separate plasma by centrifuging at 5000 rpm for 10 minutes. The concentrations of Aspartate transaminase (AST) and Alanine transaminase (AST) were measured as an indication of cell toxicity in liver. As shown in FIG. 26A and FIG. 26B, while jetPEI causes a high level of hepatotoxicity, the liver enzyme levels in blood did not significantly rise above the normal range for the particles prepared with PEG molecular weight of 500 Da at 0.5% and 2000 Da at 2% PEG, showing that the role of PEG in reducing the toxicity of particles is preserved with lower molecular weight.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A polymeric micellar nanoparticle composition, comprising:
   (a) a graft copolymer comprising at least one polycationic polymer and at least one polyethylene glycol (PEG) polymer having an average molecular weight ranging from about 500 Da to about 700 Da, wherein the at least one PEG polymer is terminated with a hydroxyl group; and
   (b) at least one nucleic acid;
   wherein the graft copolymer has a PEG graft density ranging from about 0.25 mol % to about 10 mol % and the at least one nucleic acid are complexed and condensed into a shaped micellar nanoparticle that is stable in biological media.

2. The composition of claim 1, wherein the shaped micellar nanoparticle is selected from the group consisting of a spherically-shaped micellar nanoparticle, a rod-shaped micellar nanoparticle, and a worm-shaped micellar nanoparticle.

3. The composition of claim 1, further comprising a ligand conjugated to the at least one PEG polymer and/or the terminal hydroxyl group.

4. The composition of claim 3, wherein:
   (i) the ligand is selected from the group consisting of a diagnostic agent, an imaging agent, a targeting agent, a theranostic agent, a therapeutic agent, and combinations thereof; or
   (ii) the ligand is selected from the group consisting of a DNA, RNA, polypeptide, antibody, antibody fragment, antigen, carbohydrate, protein, peptide, enzyme, amino acid, hormone, steroid, vitamin, drug, virus, polysaccharide, lipid, lipopolysaccharide, glycoprotein, lipoprotein, nucleoprotein, oligonucleotide, immunoglobulin, albumin, hemoglobin, coagulation factor, peptide hormone, protein hormone, non-peptide hormone, interleukin, interferon, cytokine, peptides comprising a tumor-specific epitope, cell, cell-surface molecule, cell adhesion peptide, cell-binding peptide, cell receptor ligand, small organic molecule, small organometallic molecule, nucleic acid, and transferrin; or
   (iii) the ligand is detectable using an imaging modality selected from the group consisting of bioluminescence imaging, fluorescence imaging, magnetic resonance imaging (MRI), positron emission tomography (PET), x-ray computed tomography (CT), single-photon emission computed tomography (SPECT), and combinations thereof; or
   (iv) the ligand comprises a peptide comprising the amino acid sequence Ac-CCRRYVVLPRWLC (SEQ ID NO: 1), cyclic RGD-thiol peptide (cRGD), or a peptide comprising the amino acid sequence YIGSR (SEQ ID NO: 3); or
   (v) the ligand comprises a moiety that binds to a tumor-specific antigen; or
   (vi) the ligand comprises a prostate-specific membrane antigen (PSMA)-binding moiety.

5. The composition of claim 1, wherein:
   (i) the at least one polycationic polymer is selected from the group consisting of linear polyethylenimine (LPEI), poly-lysine, poly-arginine, poly-histidine, chitosan, branched PEI, a poly (beta-aminoester), a polyphosphoester (PPE), and polyphosphoramidate (PPA); or
   (ii) the at least one polycationic polymer is LPEI; or
   (iii) the at least one polycationic polymer is not branched PEI; or
   (iv) the graft copolymer is not a branched PEI(25 kDa)-g-linear PEG(550 Da)$_n$ copolymer, wherein n is the average number of PEG blocks per one PEI macromolecule and n is equal to 35.

6. The composition of claim 5, wherein:
   (i) the LPEI has a molecular weight ranging from about 2 kDa to about 50 kDa; or
   (ii) the LPEI has a molecular weight of about 22 kDa.

7. The composition of claim 1, wherein:
   (i) the at least one nucleic acid has a length ranging from about 10 bases to about 10 kilobases (kb); or
   (ii) the at least one nucleic acid is selected from the group consisting of an antisense oligonucleotide, cDNA, genomic DNA, guide RNA, plasmid DNA, vector DNA, mRNA, miRNA, piRNA, shRNA, and siRNA; or
   (iii) the at least one nucleic acid comprises an expression vector encoding at least one reporter gene operably linked to a promoter; or
   (iv) the at least one nucleic acid comprises an expression vector encoding at least one antigen epitope operably linked to a promoter.

8. The composition of claim 7, wherein:
   (i) the reporter gene is selected from the group consisting of a bioluminescent reporter gene, a fluorescent reporter gene, a PET reporter gene, and combinations thereof; or
   (ii) the promoter is selected from the group consisting of a constitutively active promoter, an inducible promoter, a tissue-specific promoter, and a tumor-specific promoter; or
   (iii) the expression vector further comprises a therapeutic gene; or
   (iv) the expression vector further comprises an antigen gene.

9. The composition of claim 8, wherein:
   (i) the therapeutic gene is selected from the group consisting of a cytotoxic gene, an immunomodulator gene, a suicide gene, and a tumor suppressor gene; or
   (ii) the antigen gene encodes at least one antigen against infectious diseases, allergens, or cancer cells.

10. The composition of claim 1, further comprising a therapeutic agent or a chemotherapeutic agent.

11. The composition of claim 1, wherein the micellar nanoparticle composition targets at least one target cancer cell.

12. The composition of claim 11, wherein:
(i) the cancer cell comprises a metastatic cancer cell; or
(ii) the cancer cell is selected from the group consisting of a breast cancer cell, a cervical cancer cell, a melanoma cancer cell, and a prostate cancer cell.

13. The composition of claim 1, wherein the micellar nanoparticle composition exhibits a transfection efficiency of the at least one target cancer cell of between 10-fold and 100-fold greater than a micellar nanoparticle composition comprising a PEG polymer having an average molecular weight greater than 1 kDa.

14. A transfection agent for transfecting a cell with at least one nucleic acid, the transfection agent comprising the polymeric micellar nanoparticle composition of claim 1.

15. The transfection agent of claim 14, wherein the transfection agent modulates expression of at least one gene in a cell, tissue, or subject.

16. A method for targeting at least one metastatic cancer cell in a subject, the method comprising administering the transfection agent of claim 14 to a subject, wherein the polymeric micellar nanoparticle composition comprises a ligand that binds to a tumor-specific antigen on the surface of the at least one metastatic cancer cell, and wherein the ligand binds to the tumor-specific antigen on the surface of the at least one metastatic cancer cell after administration of the transfection agent to the subject, thereby targeting the at least one metastatic cancer cell in the subject.

17. The method of claim 16, wherein the polymeric micellar nanoparticle composition further comprises a chemotherapeutic agent and/or at least one nucleic acid encoding a therapeutic gene that inhibits the growth, proliferation and/or survival of the at least one metastatic cancer cell.

18. The method of claim 17, wherein targeting the at least one metastatic cancer cell comprises treating a metastatic cancer in the subject.

19. The method of claim 16, wherein the polymeric micellar nanoparticle composition further comprises an imaging agent and/or at least one nucleic acid encoding a reporter gene operably linked to a tumor-specific promoter.

20. The method of claim 19, wherein the reporter gene is selected from the group consisting of a bioluminescent reporter gene, a fluorescent reporter gene, a CT reporter gene, an MM reporter gene, a PET reporter gene, a SPECT reporter gene, and combinations thereof.

21. The method of claim 19, wherein targeting the at least one metastatic cancer cell comprises detecting, diagnosing, and/or imaging a metastatic cancer in the subject.

22. The method of claim 16, further comprising imaging the subject after administering the transfection agent using an imaging modality selected from the group consisting of bioluminescent imaging, fluorescent imaging, CT, MRI, PET, SPECT, X-ray, and combinations thereof.

23. A method for treating a disease or condition, the method comprising administering to a subject in need of treatment thereof, the polymeric micellar nanoparticle composition of claim 1, wherein the at least one nucleic acid comprises an expression vector encoding at least one therapeutic gene.

24. A method for preventing a disease or condition, the method comprising administering to a subject in need of prophylactic treatment thereof, the polymeric micellar nanoparticle composition of claim 1, wherein the at least one nucleic acid comprises an expression vector encoding at least one antigen gene.

* * * * *